(12) United States Patent
Hatakeyama et al.

(10) Patent No.: US 9,632,415 B2
(45) Date of Patent: *Apr. 25, 2017

(54) PATTERN FORMING PROCESS AND SHRINK AGENT

(71) Applicant: Shin-Etsu Chemical Co., Ltd., Tokyo (JP)

(72) Inventors: Jun Hatakeyama, Joetsu (JP); Kazuhiro Katayama, Joetsu (JP); Koji Hasegawa, Joetsu (JP); Masayoshi Sagehashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/918,859

(22) Filed: Oct. 21, 2015

(65) Prior Publication Data

US 2016/0139512 A1    May 19, 2016

(30) Foreign Application Priority Data

Oct. 30, 2014    (JP) .................................. 2014-221399

(51) Int. Cl.
*G03F 7/11*    (2006.01)
*G03F 7/40*    (2006.01)
(Continued)

(52) U.S. Cl.
CPC ............... *G03F 7/40* (2013.01); *C07C 381/12* (2013.01); *C08F 220/14* (2013.01);
(Continued)

(58) Field of Classification Search
CPC ...... G03F 7/004; G03F 7/0045; G03F 7/0046; G03F 7/11; G03F 7/32; G03F 7/40;
(Continued)

(56) References Cited

U.S. PATENT DOCUMENTS 6,579,657 B1    6/2003  Ishibashi et al.
7,390,616 B2 *  6/2008  Brodsky .................. G03F 7/40
                                            430/311
(Continued)

FOREIGN PATENT DOCUMENTS

JP    10-73927 A     3/1998
JP    2008-275995 A  11/2008

OTHER PUBLICATIONS

Yi et al., "Contact Hole Patterning for Random Logic Circuits using Block Copolymer Directed Self-Assembly", Proc. of SPIE, 2012, vol. 8323, pp. 83230W-1-83230W-6.

*Primary Examiner* — Amanda C Walke
(74) *Attorney, Agent, or Firm* — Westerman, Hattori, Daniels & Adrian, LLP

(57) ABSTRACT

A negative pattern is formed by applying a resist composition onto a substrate, exposing the resist film, and developing the exposed resist film in an organic solvent developer. The process further involves coating the negative pattern with a shrink agent solution of a polymer comprising recurring units capable of forming lactone under the action of acid in a $C_7$-$C_{16}$ ester or $C_8$-$C_{16}$ ketone solvent, baking the coating, and removing the excessive shrink agent via organic solvent development for thereby shrinking the size of spaces in the pattern.

10 Claims, 2 Drawing Sheets

(51) Int. Cl.
*C07C 381/12* (2006.01)
*C08F 220/28* (2006.01)
*G03F 7/004* (2006.01)
*C08F 220/14* (2006.01)
*H01L 21/027* (2006.01)
*C08F 220/24* (2006.01)
*C09D 133/06* (2006.01)
*G03F 7/039* (2006.01)
*G03F 7/32* (2006.01)

(52) U.S. Cl.
CPC .......... *C08F 220/24* (2013.01); *C08F 220/28* (2013.01); *C09D 133/06* (2013.01); *G03F 7/004* (2013.01); *G03F 7/0045* (2013.01); *G03F 7/0392* (2013.01); *G03F 7/0397* (2013.01); *G03F 7/325* (2013.01); *G03F 7/405* (2013.01); *H01L 21/0274* (2013.01)

(58) Field of Classification Search
CPC .... C08F 220/14; C08F 220/28; C08F 220/24; H01L 21/0274; C07C 381/12
USPC ......... 430/434, 435, 270.1, 271.1, 322, 325, 430/329, 330, 331, 913; 526/309, 318, 526/318.43, 319, 321, 326
See application file for complete search history.

(56) References Cited

U.S. PATENT DOCUMENTS

| | | | |
|---|---|---|---|
| 8,101,333 B2* | 1/2012 | Noya | G03F 7/40 430/270.1 |
| 9,081,290 B2* | 7/2015 | Hatakeyama | G03F 7/004 |
| 2010/0119717 A1 | 5/2010 | Hong et al. | |
| 2012/0034558 A1* | 2/2012 | Chang | G03F 7/0046 430/270.1 |
| 2013/0071788 A1* | 3/2013 | Hatakeyama | G03F 1/00 430/285.1 |
| 2013/0171825 A1* | 7/2013 | Xu | H01L 21/0274 438/694 |
| 2014/0186772 A1* | 7/2014 | Pohlers | G03F 7/405 430/311 |
| 2014/0199632 A1* | 7/2014 | Hasegawa | G03F 7/0045 430/285.1 |
| 2014/0212808 A1* | 7/2014 | Funatsu | G03F 7/038 430/270.1 |
| 2014/0308614 A1* | 10/2014 | Hasegawa | G03F 7/038 430/281.1 |
| 2015/0086929 A1* | 3/2015 | Hatakeyama | G03F 7/40 430/324 |
| 2015/0338744 A1* | 11/2015 | Hatakeyama | G03F 7/40 430/331 |

* cited by examiner

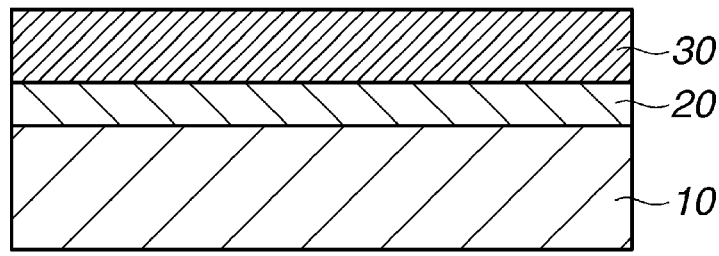
FIG.1A COATING OF RESIST
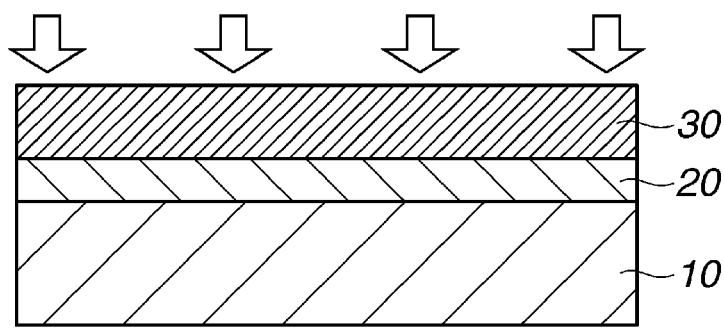
FIG.1B EXPOSURE OF RESIST
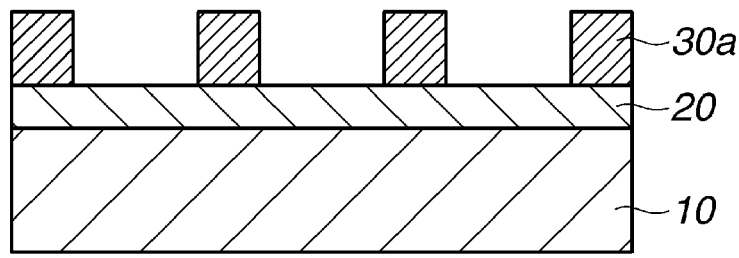
FIG.1C PEB AND ORGANIC SOLVENT DEVELOPMENT OF RESIST TO FORM NEGATIVE PATTERN

PATTERN FORMING PROCESS AND SHRINK AGENT

CROSS-REFERENCE TO RELATED APPLICATION

This non-provisional application claims priority under 35 U.S.C. §119(a) on Patent Application No. 2014-221399 filed in Japan on Oct. 30, 2014, the entire contents of which are hereby incorporated by reference.

TECHNICAL FIELD

This invention relates to a shrink agent and a pattern forming process comprising forming a resist pattern via resist coating, exposure and development, coating the resist pattern with a shrink agent, baking, and developing the shrink agent for shrinking the size of spaces in the resist pattern.

BACKGROUND ART

While the effort to reduce the pattern rule is in rapid progress to meet the recent demand for higher integration level and operating speed of LSIs, the photolithography is on widespread use. The photolithography has the essential limit of resolution determined by the wavelength of a light source. One micropatterning approach to go beyond the limit of resolution is by combining ArF excimer laser immersion lithography with double patterning. One typical version of double patterning is litho-etch-litho-etch (LELE) process involving forming a pattern via exposure, transferring the pattern to a hard mask on a substrate by etching, effecting second exposure at a half-pitch shifted position, and etching the hard mask. This process has the problem of misalignment between two exposures or overlay error. Another version of double patterning is self-aligned double patterning (SADP) process involving the steps of transferring a resist pattern to a hard mask, growing a film on opposite sides of hard mask features, and leaving sidewalls of film for thereby doubling pattern size. The SADP process needs exposure only once and mitigates the problem of overlay error. To simplify the process, a modified version of the SADP process of forming a silicon oxide film on sidewalls of resist pattern features as developed rather than sidewalls of hard mask features for thereby doubling pattern size is also proposed. Since the SADP process is successful in reducing the pitch of line pattern to half, the pitch can be reduced to ¼ by repeating the SADP process twice.

Not only shrinking of line patterns, but also shrinking of hole patterns is necessary. Unless the hole pattern is shrunk, shrinkage over the entire chip is incomplete. One known method of shrinking a hole pattern is RELACS® method described in JP-A H10-73927. This method intends to reduce the size of a hole pattern by coating a resist pattern as developed with a water-soluble material containing a crosslinker, and baking the coating to form a crosslinked layer on the resist surface for causing the resist pattern to be thickened. JP-A 2008-275995 describes a water-soluble shrink material comprising an amino-containing polymer or polyamine, which bonds to the resist surface via neutralization reaction with carboxyl groups on the resist surface, for thereby thickening the resist film. It is also proposed in Proc. SPIE Vol. 8323 p83230W-1 (2012) to shrink a hole pattern by utilizing the direct self-assembly (DSA) of a block copolymer.

Shrinkage by the RELACS® method has the problem that since a crosslinker becomes active with an acid catalyst within resist, the size of holes is non-uniform after shrinkage if acid diffusion is non-uniform. In the shrink method based on neutralization and bonding of water-soluble amino polymer, the pattern is thickened as direct reflection of irregularities on the resist surface so that dimensional variations of the resist pattern as developed and dimensional variations after shrinkage are identical. The shrink method utilizing the DSA function of a block copolymer has advantages including an increased amount of shrinkage and a minimal dimensional variation after shrinkage, but some problems. Namely, if the DSA is applied to holes of different size, shrinkage cannot be induced for those holes of the size that causes a contradictory assembly of block copolymer. If the DSA is applied to a trench pattern, shape deformation becomes a problem, for example, a plurality of hole patterns are formed.

There is a need for a shrink agent which can shrink a trench pattern without changing the shape of the resist pattern, and improve the dimensional variation and edge roughness (LWR) of the resist pattern after development.

CITATION LIST

Patent Document 1: JP-A H10-73927 (U.S. Pat. No. 6,579,657)

Patent Document 2: JP-A 2008-275995 (US 20100119717)

Non-Patent Document 1: Proc. SPIE Vol. 8323 p83230W-1 (2012)

SUMMARY OF INVENTION

As discussed above, the method of applying a RELACS® material of crosslink type or neutralizing reaction-mediated bond type onto a resist pattern causes no pattern deformation, but fails to reduce the dimensional variation of the resist pattern. The DSA method can reduce the dimensional variation of a hole pattern as developed, but invites pattern deformation when applied to a trench pattern as developed.

An object of the invention is to provide a shrink agent which when coated onto a resist pattern as developed, can reduce the dimensional variation of the resist pattern, and when applied to a trench pattern, can shrink the trench size without causing pattern deformation; and a pattern forming process using the same.

In one aspect, the invention provides a pattern forming process comprising the steps of applying a resist composition comprising a polymer comprising recurring units having an acid labile group-substituted carboxyl group, an acid generator and an organic solvent, onto a substrate; prebaking to form a resist film; exposing the resist film to high-energy radiation; baking the film; developing the exposed resist film in an organic solvent-based developer to form a negative pattern; applying a shrink agent onto the negative pattern; baking; and removing the excessive shrink agent with the organic solvent-based developer for thereby shrinking the size of spaces in the pattern. The shrink agent used herein is a solution of a polymer comprising recurring units (a1) and/or (a2) having the general formula (1) in a solvent selected from the group consisting of ester solvents of 7 to 16 carbon atoms and ketone solvents of 8 to 16 carbon atoms.

(1)

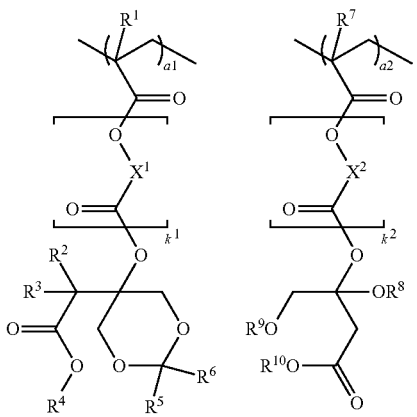

Herein $R^1$ and $R^7$ each are hydrogen or methyl; $R^2$ and $R^3$ are each independently hydrogen, fluorine, or a straight, branched or cyclic, $C_1$-$C_8$ monovalent hydrocarbon group; $R^4$, $R^8$ and $R^{10}$ are each independently hydrogen or a straight, branched or cyclic, $C_1$-$C_{20}$ monovalent hydrocarbon group in which any constituent —$CH_2$— moiety may be replaced by —O— or —C(=O)—, or which may be substituted with halogen; $R^5$ and $R^6$ are each independently hydrogen or a straight, branched or cyclic, $C_1$-$C_8$ monovalent hydrocarbon group, or $R^5$ and $R^6$ may bond together to form a $C_3$-$C_{17}$ non-aromatic ring with the carbon atom to which they are attached; $R^5$ is an acid labile group; $X^1$ and $X^2$ are each independently a straight, branched or cyclic, $C_1$-$C_{20}$ divalent hydrocarbon group in which any constituent —$CH_2$— moiety may be replaced by —O— or —C(=O)—; $k^1$ and $k^2$ each are 0 or 1, $0 \leq a1 \leq 1.0$, $0 \leq a2 \leq 1.0$, and $0 < a1 + a2 \leq 1.0$.

In a preferred embodiment, the polymer comprising recurring units (a1) and/or (a2) in the shrink agent further comprises recurring units (a4) and/or (a5) having the general formula (4).

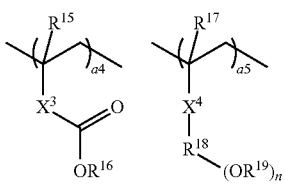

(4)

Herein $R^{15}$ and $R^{17}$ each are hydrogen or methyl; $R^{16}$ and $R^{19}$ each are an acid labile group; $X^3$ is a single bond, a phenylene or naphthylene group, or —C(=O)—O—$R^{20}$—, $R^{20}$ is a straight, branched or cyclic $C_1$-$C_{10}$ alkylene group which may contain ether, ester, lactone ring or hydroxyl, or a phenylene or naphthylene group; $X^4$ is a single bond, a phenylene or naphthylene group which may contain nitro, cyano or halogen, or —C(=O)—O—$R^{21}$—, —C(=O)—NH—$R^{21}$—, —O—$R^{21}$—, or —S—$R^{21}$—, $R^{21}$ is a straight, branched or cyclic $C_1$-$C_{10}$ alkylene group which may contain ether, ester, lactone ring or hydroxyl, or a phenylene or naphthylene group which may contain a straight, branched or cyclic $C_1$-$C_6$ alkyl, alkoxy, acyl, acyloxy, $C_2$-$C_6$ alkenyl, alkoxycarbonyl, $C_6$-$C_{10}$ aryl, nitro, cyano, or halogen; $R^{18}$ is a single bond, a di to penta-valent, straight, branched or cyclic $C_1$-$C_{16}$ aliphatic hydrocarbon group, or phenylene group, which may contain ether or ester; $0 \leq a4 < 1.0$, $0 \leq a5 < 1.0$, $0 \leq a4 + a5 < 1.0$, and n is 1 to 4.

In a preferred embodiment, the polymer comprising recurring units (a1) and/or (a2) in the shrink agent further comprises recurring units (b) having a hydroxyl, carboxyl, lactone ring, lactam ring, sultone ring, sulfone, sulfonic acid ester, sulfonamide, carboxylic acid amide, nitro, cyano, thienyl, furyl, pyrrole, acid anhydride, imide, —NH—(C=O)—O—, —S—(C=O)—O—, or —ON(=O_2)—, recurring units (d) having an oxirane or oxetane ring, and/or recurring units (e) having an amino group.

In a preferred embodiment, the solvent in the shrink agent is at least one solvent selected from the group consisting of ester solvents of 7 to 16 carbon atoms including amyl acetate, isoamyl acetate, 2-methylbutyl acetate, hexyl acetate, 2-ethylhexyl acetate, cyclohexyl acetate, methylcyclohexyl acetate, hexyl formate, ethyl valerate, propyl valerate, isopropyl valerate, butyl valerate, isobutyl valerate, tert-butyl valerate, amyl valerate, isoamyl valerate, ethyl isovalerate, propyl isovalerate, isopropyl isovalerate, butyl isovalerate, isobutyl isovalerate, tert-butyl isovalerate, isoamyl isovalerate, ethyl 2-methylvalerate, butyl 2-methylvalerate, ethyl pivalate, propyl pivalate, isopropyl pivalate, butyl pivalate, tert-butyl pivalate, ethyl pentenoate, propyl pentenoate, isopropyl pentenoate, butyl pentenoate, tert-butyl pentenoate, propyl crotonate, isopropyl crotonate, butyl crotonate, tert-butyl crotonate, butyl propionate, isobutyl propionate, tert-butyl propionate, benzyl propionate, ethyl hexanoate, allyl hexanoate, propyl butyrate, butyl butyrate, isobutyl butyrate, 3-methylbutyl butyrate, tert-butyl butyrate, ethyl 2-methylbutyrate, isopropyl 2-methylbutyrate, methyl benzoate, ethyl benzoate, propyl benzoate, butyl benzoate, phenyl acetate, benzyl acetate, methyl phenylacetate, benzyl formate, phenylethyl formate, methyl 3-phenylpropionate, ethyl phenylacetate, and 2-phenylethyl acetate, and ketone solvents of 8 to 16 carbon atoms including 2-octanone, 3-octanone, 4-octanone, 2-nonanone, 3-nonanone, 4-nonanone, 5-nonanone, ethylcyclohexanone, ethylacetophenone, ethyl n-butyl ketone, di-n-butyl ketone, and diisobutyl ketone.

In a preferred embodiment, the shrink agent further comprises a salt compound having the general formula (3)-1 or (3)-2 defined below.

In a preferred embodiment, the polymer in the resist composition comprises recurring units (a3) having the general formula (2):

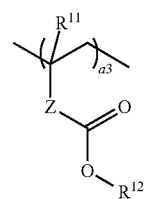

(2)

wherein $R^{11}$ is hydrogen or methyl, $R^{12}$ is an acid labile group, Z is a single bond or —C(=O)—O—$R^{13}$—, $R^{13}$ is a straight, branched or cyclic $C_1$-$C_{10}$ alkylene group which may contain ether or ester, or naphthylene group, and $0 < a3 < 1.0$.

In a preferred embodiment, the developer comprises at least one organic solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

Typically, the high-energy radiation in the exposure step is i-line of wavelength 364 nm, KrF excimer laser of wavelength 248 nm, ArF excimer laser of wavelength 193 nm, EUV of wavelength 13.5 nm, or EB.

In another aspect, the invention provides a shrink agent comprising a polymer comprising recurring units (a1) and/or (a2) having formula (1), defined above, and at least one solvent selected from ester solvents of 7 to 16 carbon atoms and ketone solvents of 8 to 16 carbon atoms.

The shrink agent may further comprise a salt compound having the general formula (3)-1 or (3)-2:

$$R^{14}-CO_2^-M^+ \quad (3)\text{-}1$$

$$R^{14}-SO_3^-M^+ \quad (3)\text{-}2$$

wherein $R^{14}$ is a straight, branched or cyclic $C_1$-$C_{20}$ alkyl group, $C_2$-$C_{20}$ alkenyl group or $C_6$-$C_{20}$ aryl group which may contain fluorine, ether, ester, lactone ring, lactam ring, carbonyl or hydroxyl, and M is sulfonium, iodonium or ammonium.

Advantageous Effects of Invention

The process of the invention involves forming a resist film of a photoresist composition comprising a polymer having an acid labile group-substituted carboxyl group and an acid generator, forming a negative tone pattern from the resist film via exposure and organic solvent development, coating the resist pattern with a shrink agent, i.e., a solution of a polymer comprising recurring units capable of forming lactone under the action of acid as represented by formula (1) in an ester solvent of 7 to 16 carbon atoms or ketone solvent of 8 to 16 carbon atoms which does not dissolve the resist pattern, baking, and removing the excessive shrink agent via organic solvent development again. The size of spaces in the resist pattern can be shrunk in a precisely size-controlled manner.

BRIEF DESCRIPTION OF DRAWINGS

FIGS. 1(A), 1(B) and 1(C) illustrate, in cross-sectional view, early steps of a pattern forming or shrinking process according to the invention; FIG. 1(A) showing a photoresist film formed on a substrate; FIG. 1(B) showing the photoresist film during exposure; and FIG. 1(C) showing pattern formation after PEB and development of the photoresist film.

FIG. 2(D) showing a shrink agent coated on the resist pattern; FIG. 2(E) showing the resist pattern whose spaces have been shrunk by baking and removal of the excessive shrink agent; and FIG. 2(F) showing dry etching of the substrate through the shrunk space pattern as a mask.

DESCRIPTION OF PREFERRED EMBODIMENTS

Figure 2D:
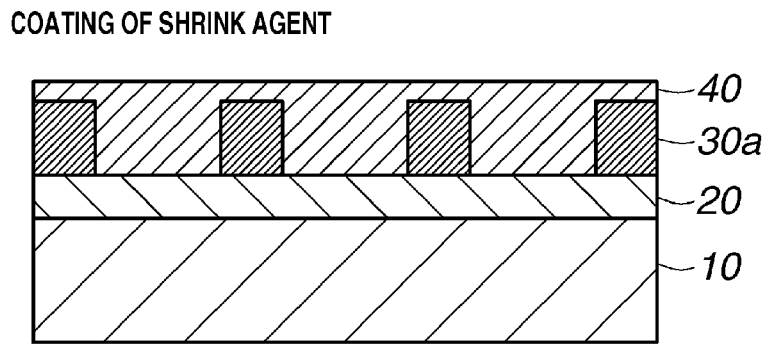
FIGS. 2(D), 2(E) and 2(F) illustrate, later steps of the pattern forming or shrinking process according to the invention.

The terms "a" and "an" herein do not denote a limitation of quantity, but rather denote the presence of at least one of the referenced item. "Optional" or "optionally" means that the subsequently described event or circumstances may or may not occur, and that description includes instances where the event or circumstance occurs and instances where it does not. As used herein, the notation ($C_n$-$C_m$) means a group containing from n to m carbon atoms per group. As used herein, the term "film" is used interchangeably with "coating" or "layer."

The abbreviations and acronyms have the following meaning.
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
LER: line edge roughness Searching for a shrink material capable of effectively shrinking a resist pattern as developed and a shrink process using the same, the inventors have found the following. A photoresist composition comprising a polymer having an acid labile group-substituted carboxyl group and an acid generator is coated to form a resist film. The resist film is processed via exposure and organic solvent development to form a negative tone resist pattern. Thereafter, the size of spaces in the resist pattern can be shrunk in a precisely size-controlled manner by coating the resist pattern with a shrink agent, i.e., a solution of a polymer comprising recurring units capable of forming lactone under the action of acid as represented by formula (1) in an ester solvent of 7 to 16 carbon atoms or ketone solvent of 8 to 16 carbon atoms, baking, and removing the excessive shrink agent via organic solvent development.

The shrink agent used in the pattern forming process of the invention is a solution of a polymer in a solvent. The polymer is defined as comprising recurring units capable of forming lactone under the action of acid, represented by the general formula (1).

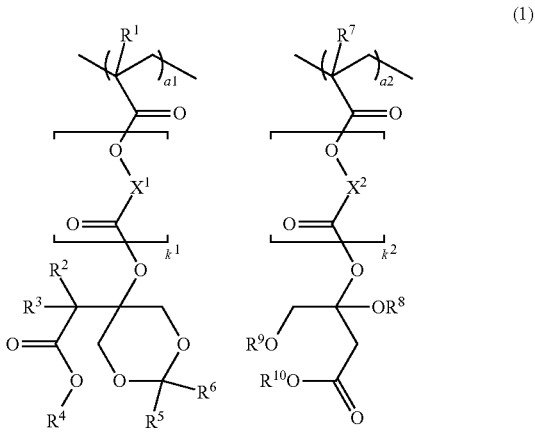

(1)

Herein $R^1$ and $R^7$ each are hydrogen or methyl. $R^2$ and $R^3$ are each independently hydrogen, fluorine, or a straight, branched or cyclic, $C_1$-$C_8$ monovalent hydrocarbon group.

$R^4$, $R^8$ and $R^{10}$ are each independently hydrogen or a straight, branched or cyclic, $C_1$-$C_{20}$ monovalent hydrocarbon group in which any constituent —$CH_2$— moiety may be replaced by —O— or —C(=O)—, or whose hydrogen may be replaced by halogen. $R^5$ and $R^6$ are each independently hydrogen or a straight, branched or cyclic, $C_1$-$C_8$ monovalent hydrocarbon group, or $R^5$ and $R^6$ may bond together to form a $C_3$-$C_{17}$ non-aromatic ring with the carbon atom to which they are attached. $R^9$ is an acid labile group. $X^1$ and $X^2$ are each independently a straight, branched or cyclic, $C_1$-$C_{20}$ divalent hydrocarbon group in which any constituent —$CH_2$— moiety may be replaced by —O— or —C(=O)—. The subscripts $k^1$ and $k^2$ each are 0 or 1, a1 and a2 are numbers in the range: $0 \le a1 \le 1.0$, $0 \le a2 \le 1.0$, and $0 < a1+a2 \le 1.0$.

Under the action of acid, the recurring unit (a1) in formula (1) forms a lactone ring according to the following scheme.

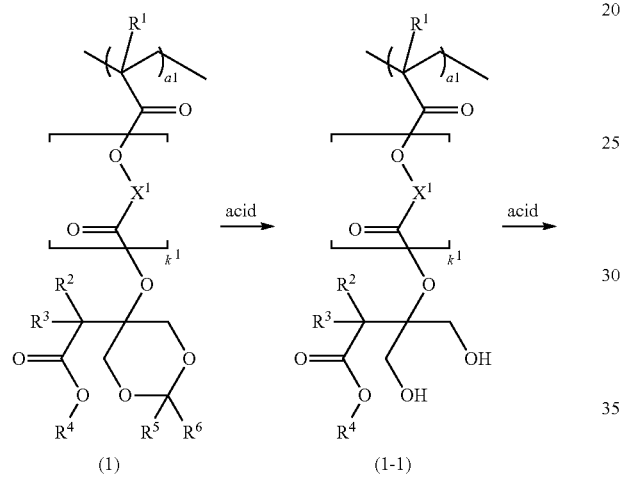

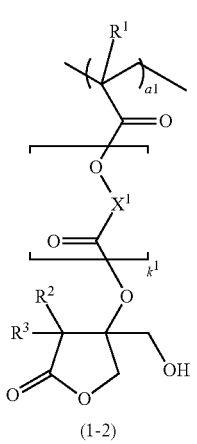

Under the action of acid, the recurring unit (a2) in formula (1) forms a lactone ring according to the following scheme.

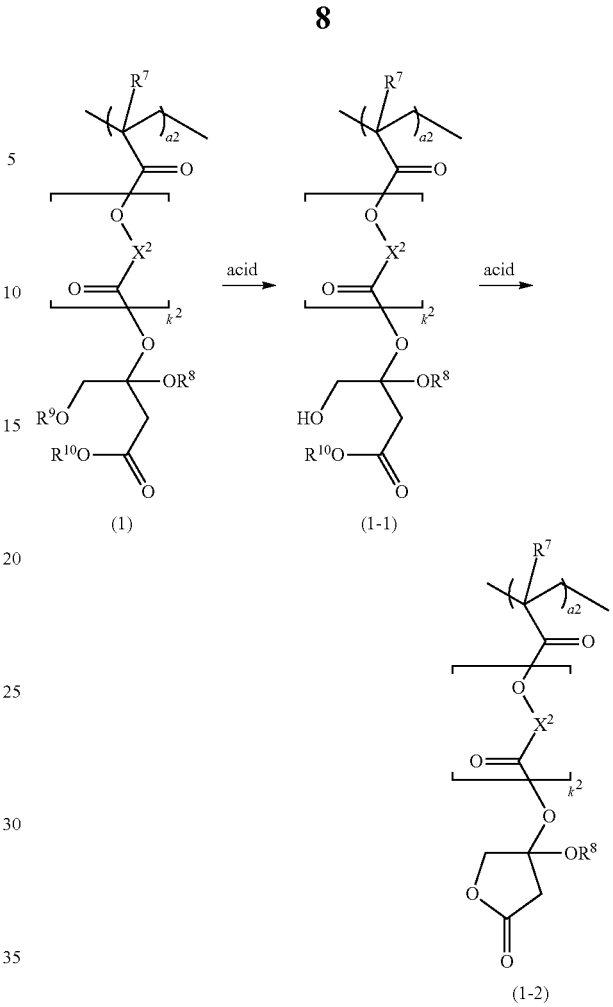

In the above schemes, $R^1$ to $R^{10}$, $X^1$, $X^2$, $k^1$ and $k^2$ are as defined above, $0 \le a1 \le 1.0$, $0 \le a2 \le 1.0$, and $0 < a1+a2 \le 1.0$.

It should be avoided that when the shrink agent solution is applied onto a resist pattern, the resist pattern is dissolved in the solvent of the shrink agent. To this end, the solvent of the shrink agent must be selected from those solvents that do not dissolve the resist film. The solvents that do not dissolve the resist film include ether solvents of 6 to 12 carbon atoms, alcohol solvents of 4 to 10 carbon atoms, hydrocarbon solvents of 6 to 12 carbon atoms, ester solvents of 7 to 16 carbon atoms, ketone solvents of 8 to 16 carbon atoms, and water. Although a number of water-based shrink agents are already proposed as alluded to previously, they are difficult to quickly apply to large-diameter wafers because of the high surface tension of water. A problem arises particularly in the case of a fine hole pattern formed via negative development. When holes are filled with the shrink agent by spin coating, the water solvent having a high surface tension prevents the shrink agent from burying in the holes to the bottom. In contrast, when a shrink agent dissolved in an organic solvent having a lower surface tension than water is applied, the ability to fill or bury to the hole bottom is improved. Also the organic solvent used in the shrink agent must dissolve the base polymer of the shrink agent. As the solvent capable of dissolving a polymer comprising recurring units having formula (1), ester solvents of 7 to 16 carbon atoms and ketone solvents of 8 to 16 carbon atoms must be selected among the aforementioned organic solvents.

Monomers Ma1 and Ma2 from which recurring units (a1) and (a2) are derived have the following formulae.
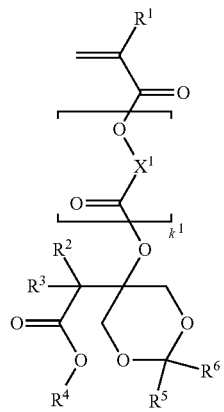
Ma1
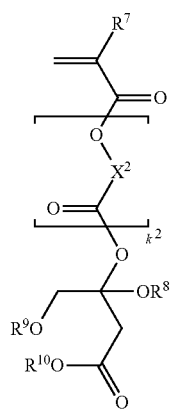
Ma2
Herein $R^1$ to $R^{10}$, $X^1$, $X^2$, $k^1$ and $k^2$ are as defined above.
Examples of monomer Ma1 are shown below. Herein $R^1$ is as defined above.
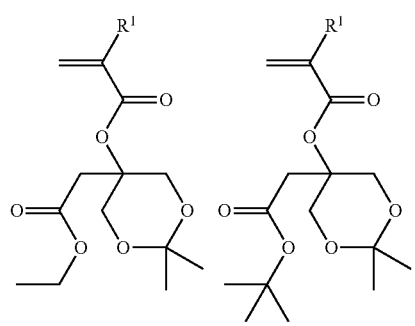
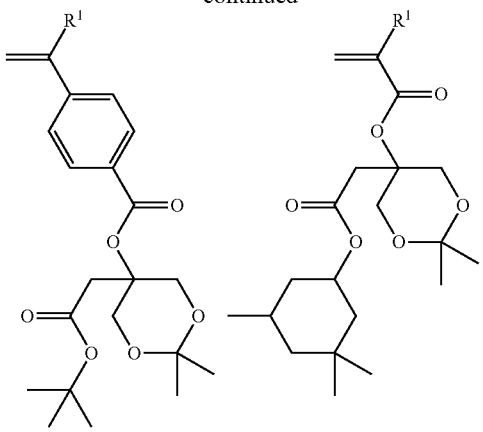
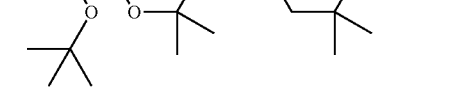
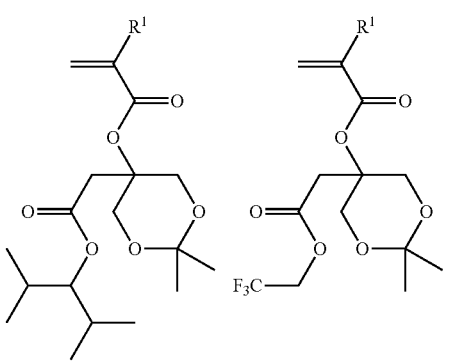
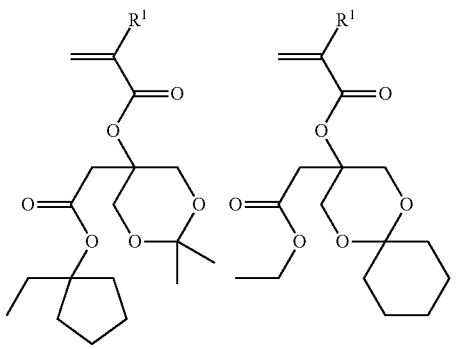
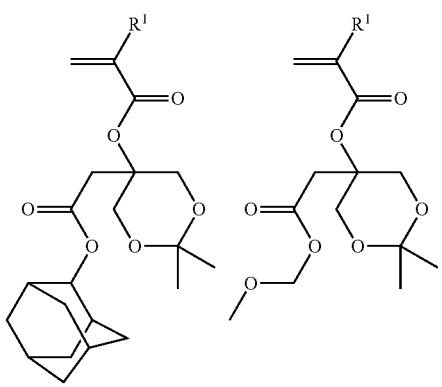

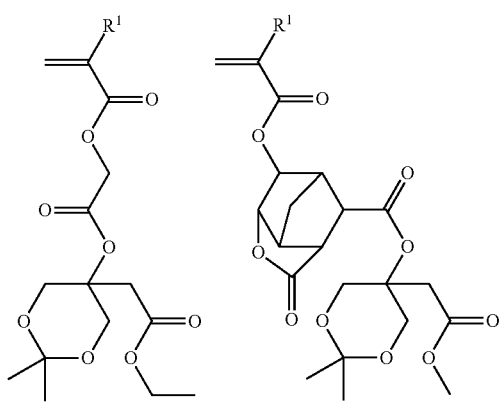
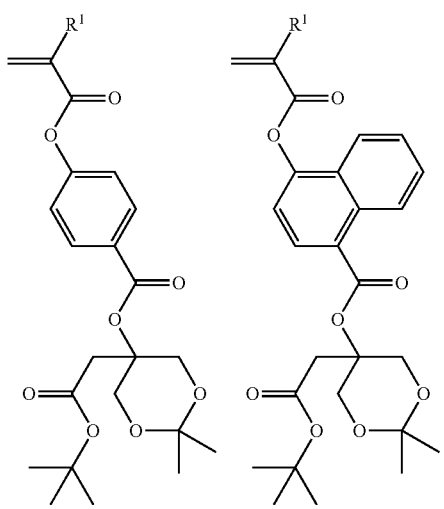
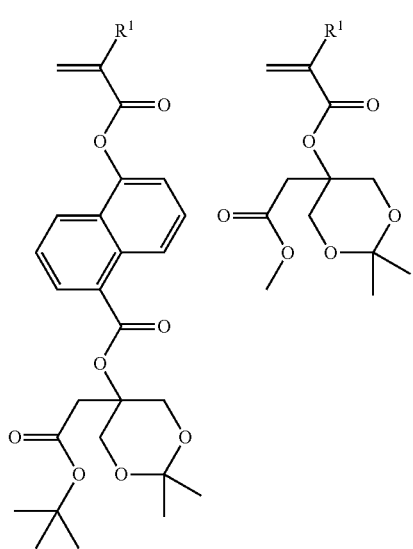
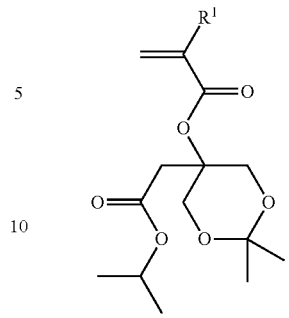
Examples of monomer Ma2 are shown below. Herein $R^7$ is as defined above.
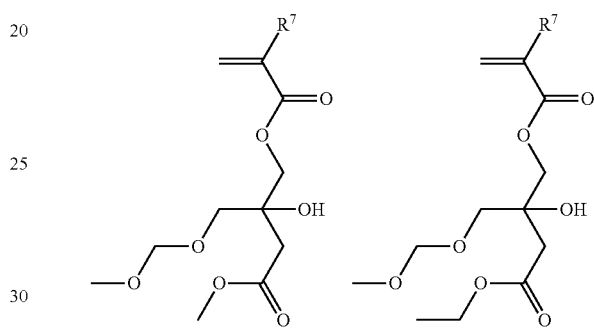
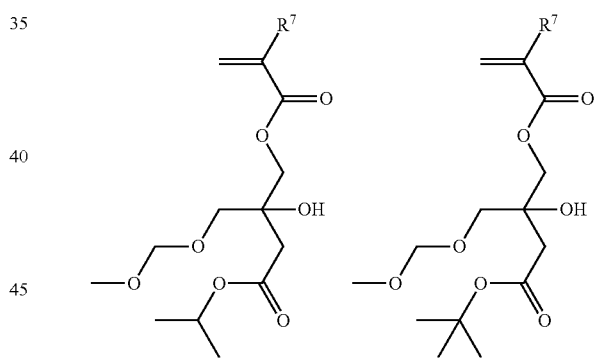
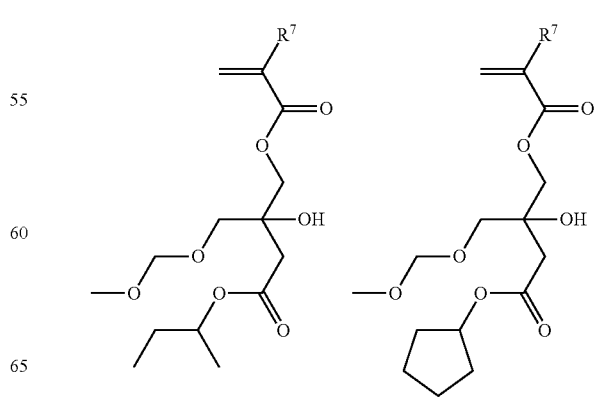

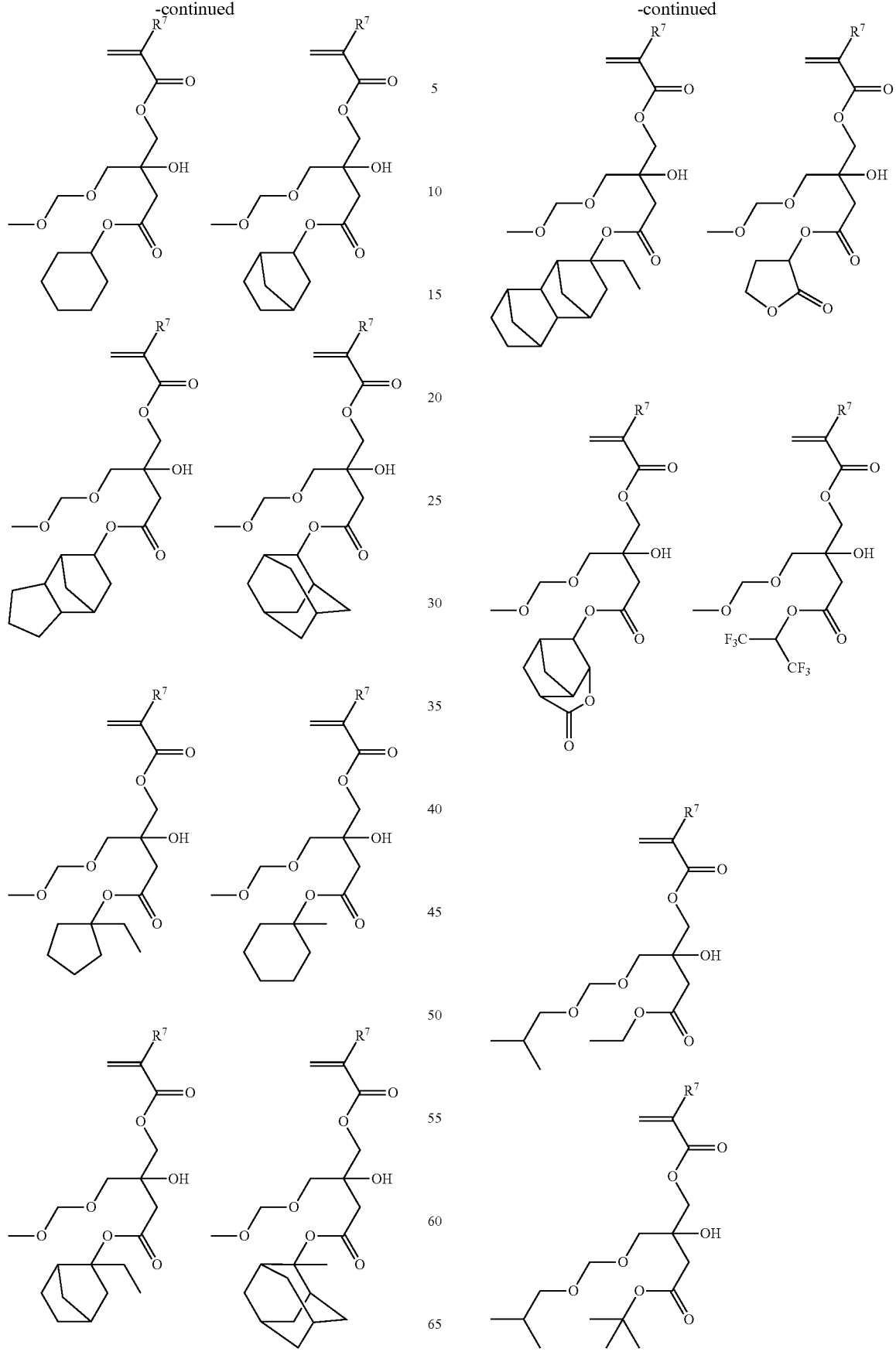

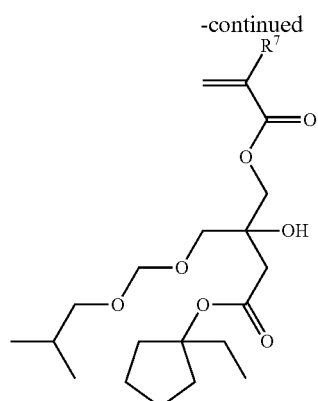
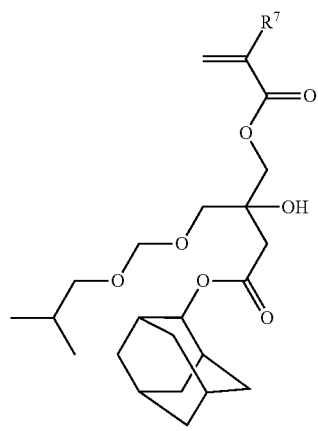
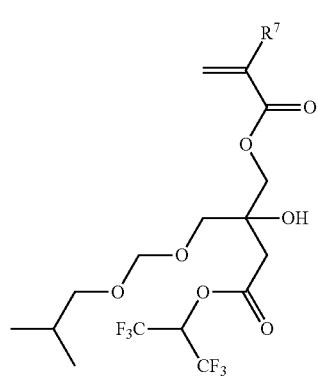
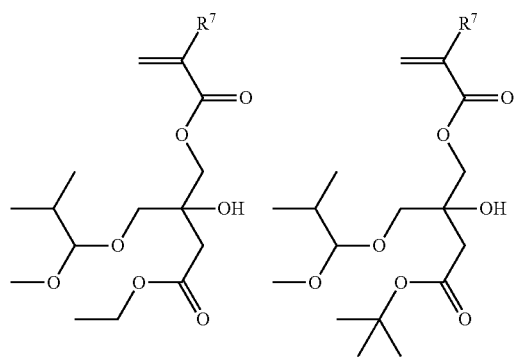
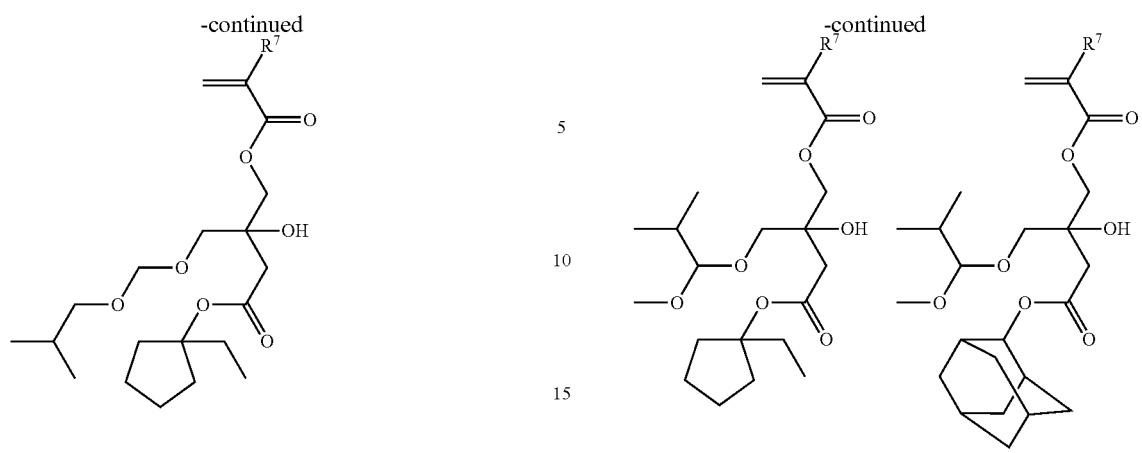
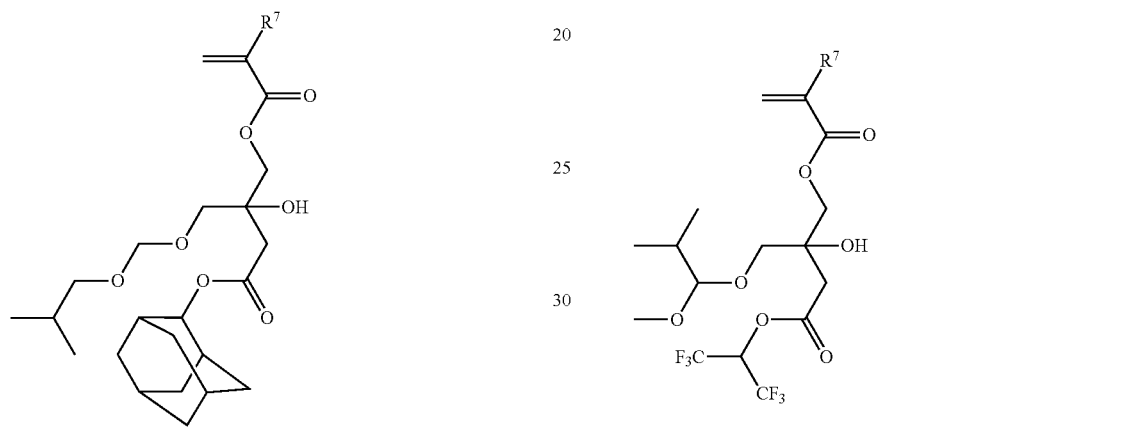
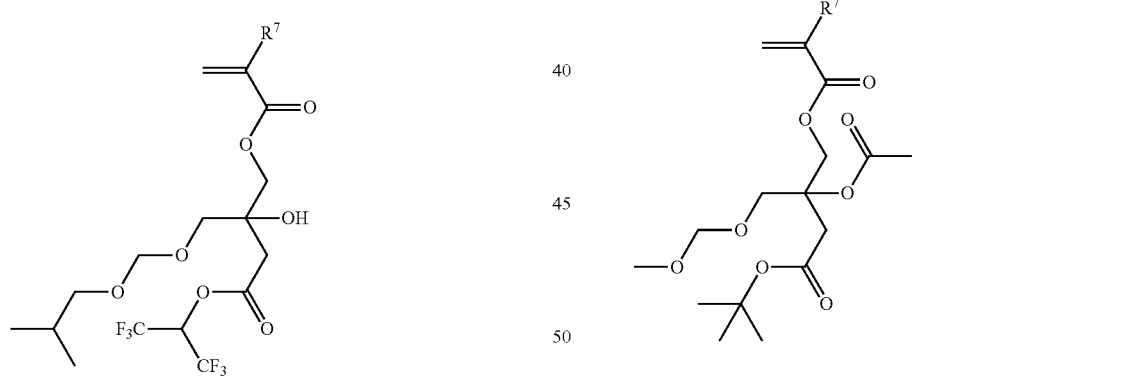
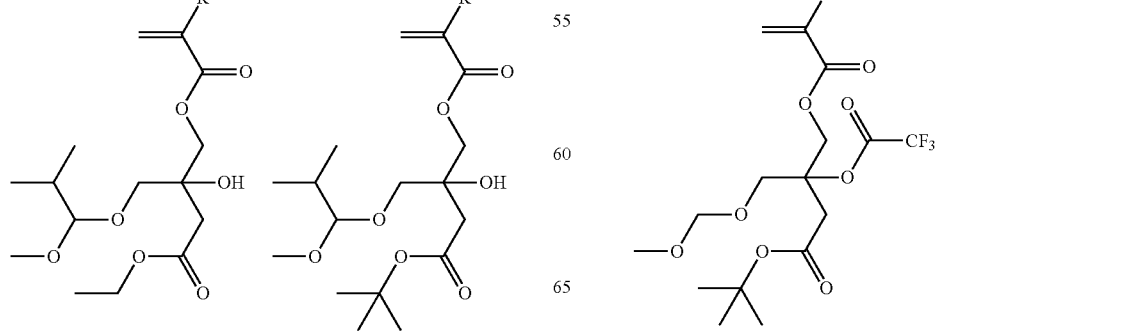

-continued
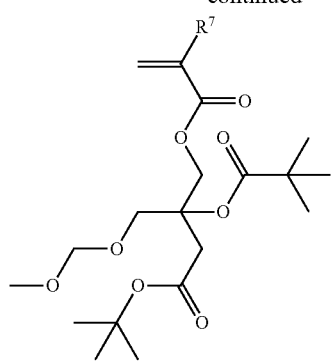
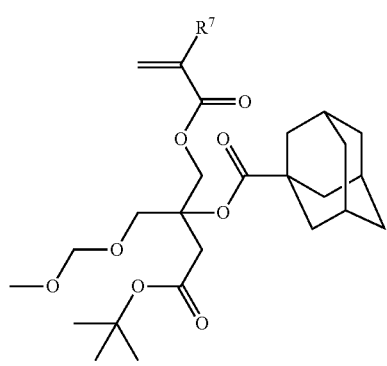
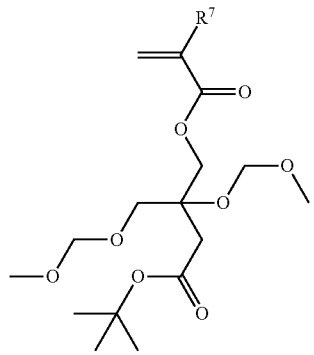
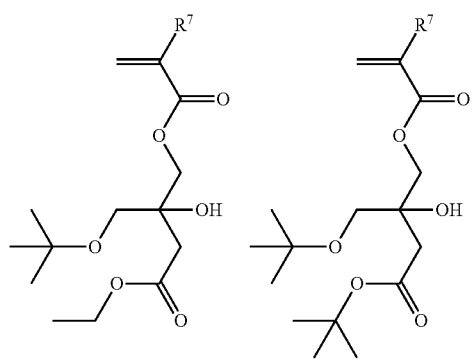
-continued
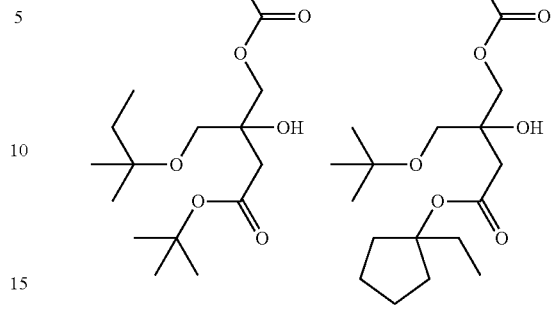
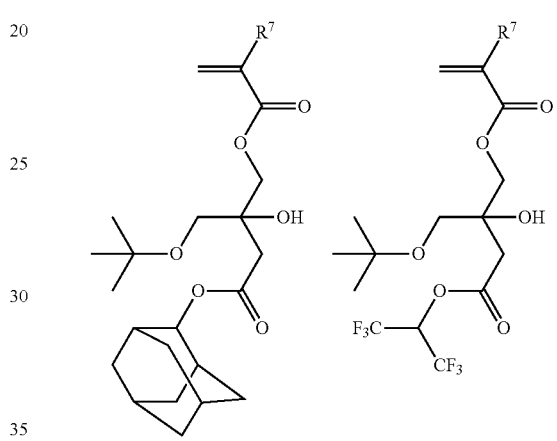
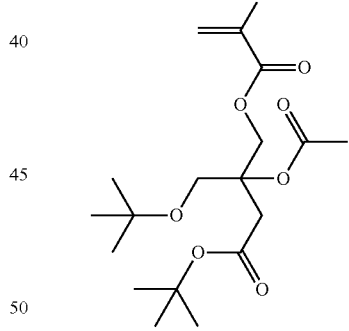
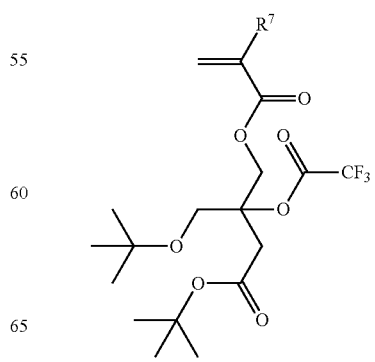

-continued
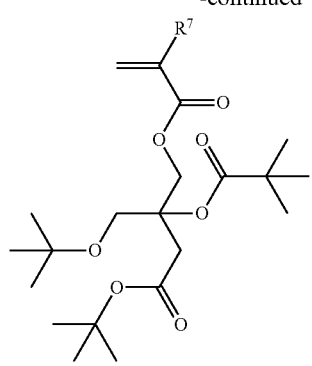
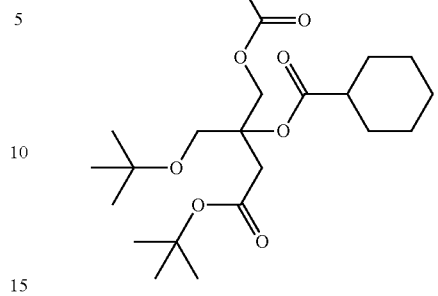
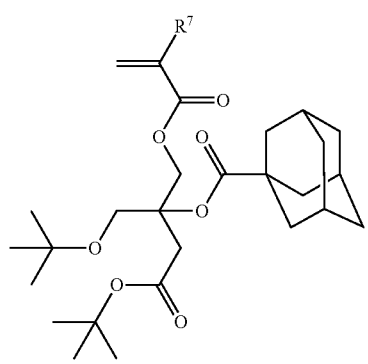
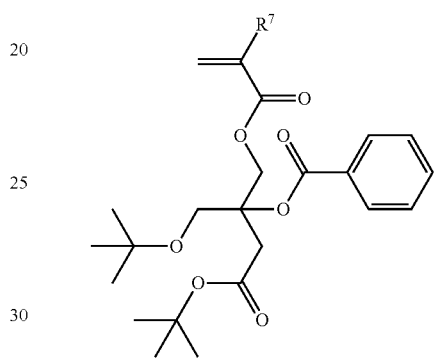
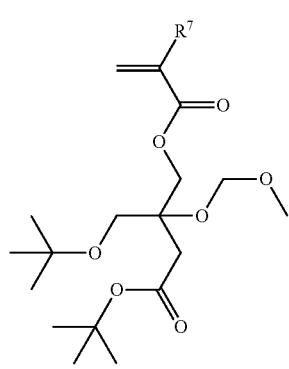
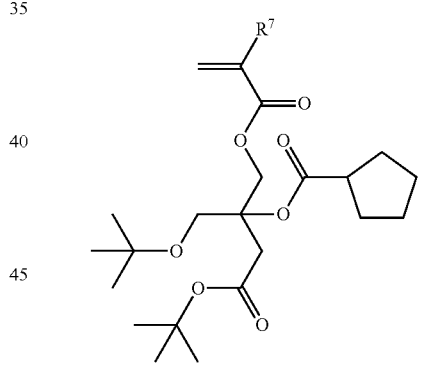
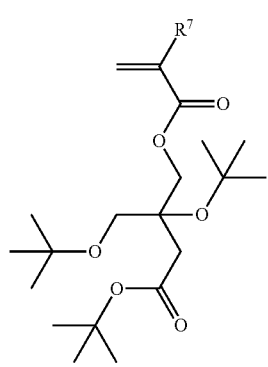
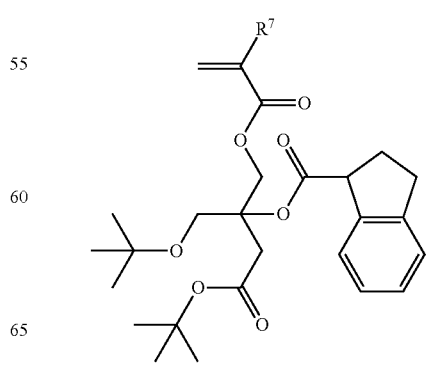

-continued
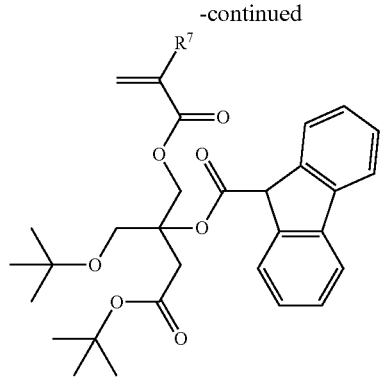
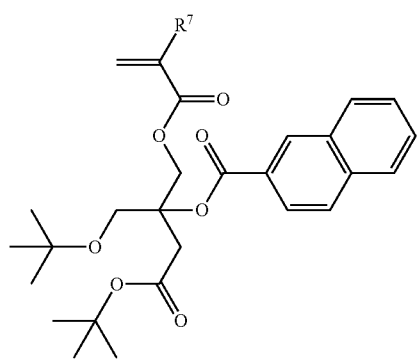
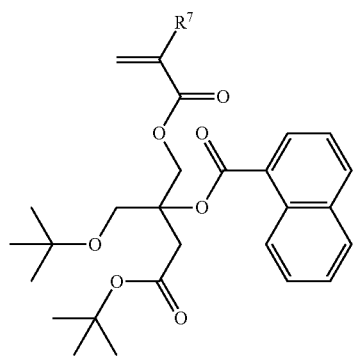
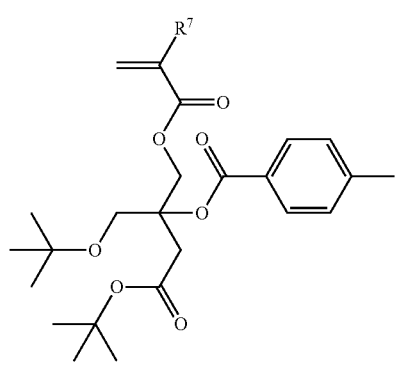
-continued
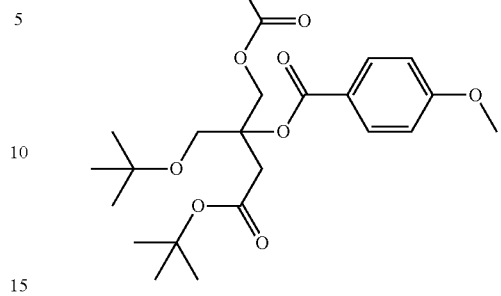
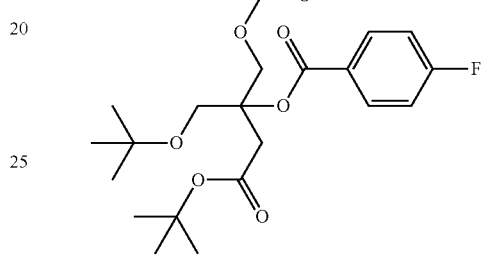
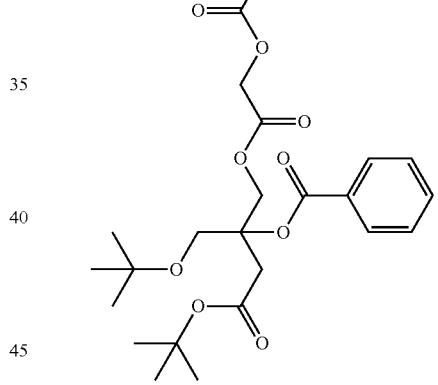
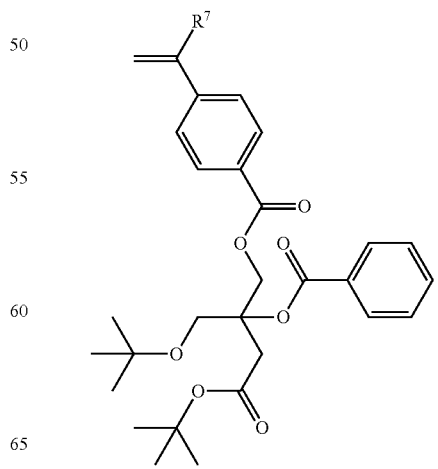

-continued

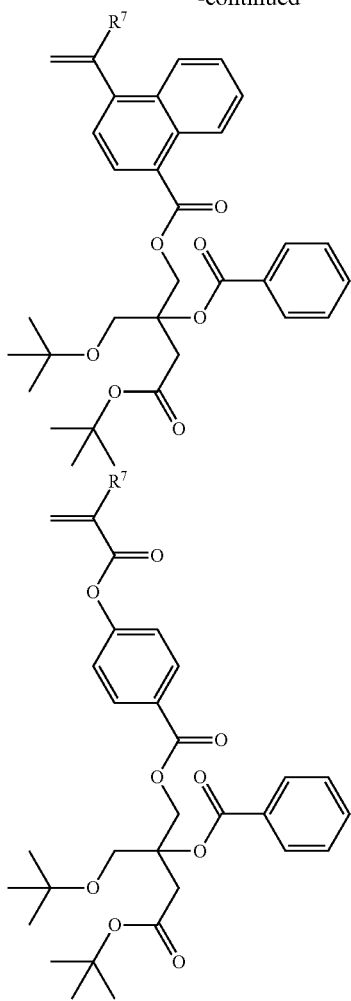

In addition to recurring units (a1) and/or (a2) represented by formula (1), the polymer for the shrink agent may further comprise recurring units (a4) and/or (a5) having a substituted carboxyl and/or hydroxyl group, represented by the general formula (4).

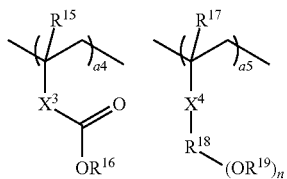

(4)

Herein $R^{15}$ and $R^{17}$ each are hydrogen or methyl. $R^{16}$ and $R^{19}$ each are an acid labile group. $X^3$ is a single bond, a phenylene or naphthylene group, or —C(=O)—O—$R^{20}$—, wherein $R^{20}$ is a straight, branched or cyclic $C_1$-$C_{10}$ alkylene group which may contain ether, ester, lactone ring or hydroxyl, or a phenylene or naphthylene group. $X^4$ is a single bond, a phenylene or naphthylene group which may contain nitro, cyano or halogen, or —C(=O)—O—$R^{21}$—, —C(=O)—NH—$R^{21}$—, —O—$R^{21}$—, or —S—$R^{21}$—, wherein $R^{21}$ is a straight, branched or cyclic $C_1$-$C_{10}$ alkylene group which may contain ether, ester, lactone ring or hydroxyl, or a phenylene or naphthylene group which may contain a straight, branched or cyclic $C_1$-$C_6$ alkyl, alkoxy, acyl, acyloxy, $C_2$-$C_6$ alkenyl, alkoxycarbonyl, $C_6$-$C_{10}$ aryl, nitro, cyano, or halogen. $R^{18}$ is a single bond, a di to penta-valent, straight, branched or cyclic $C_1$-$C_{16}$ aliphatic hydrocarbon group, or phenylene group, which may contain an ether or ester moiety. The subscripts a4 and a5 are numbers in the range: $0 \le a4 < 1.0$, $0 \le a5 < 1.0$, $0 \le a4+a5 < 1.0$, and n is 1 to 4.

In addition to the recurring units having formulae (1) and (4), the polymer may further comprise recurring units (b) having a hydroxyl, carboxyl, lactone ring, lactam ring, sultone ring, sulfone, sulfonic acid ester, sulfonamide, carboxylic acid amide, nitro, cyano, thienyl, furyl, pyrrole, acid anhydride, imide, —NH—(C=O)—O—, —S—(C=O)—O, or —ON(=O$_2$)—. Examples of the monomer from which recurring units (b) are derived are shown below.

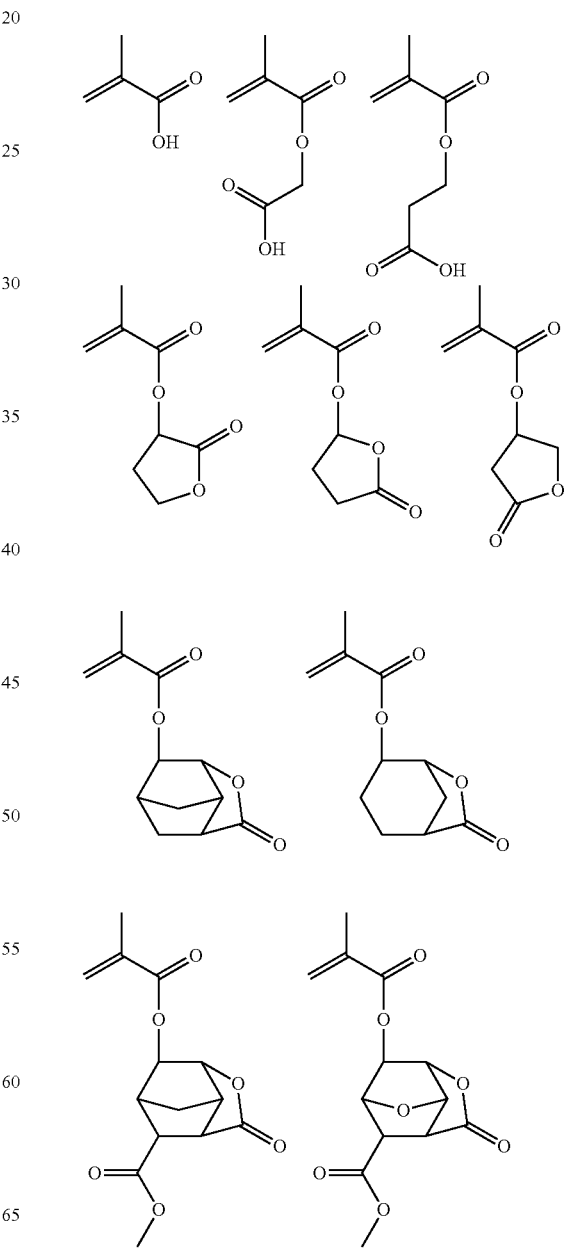

25
-continued
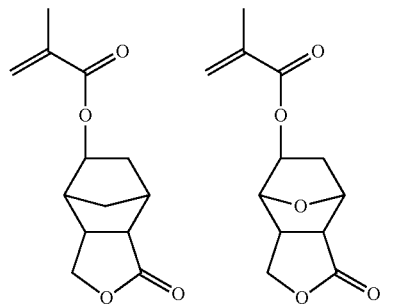
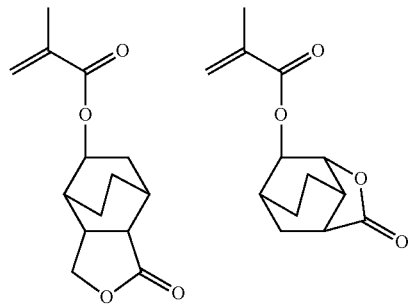
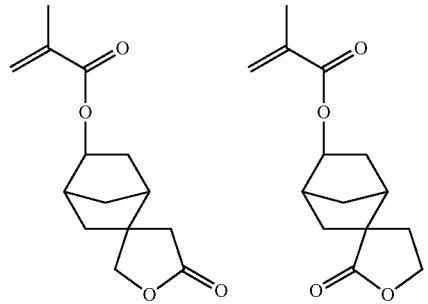
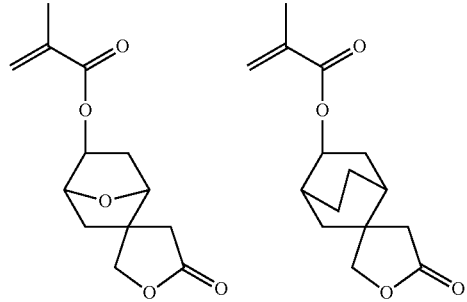
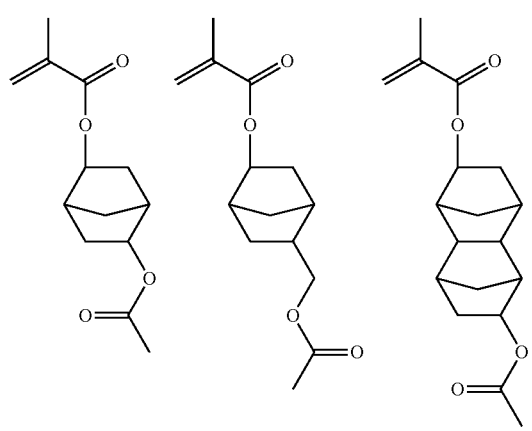
26
-continued
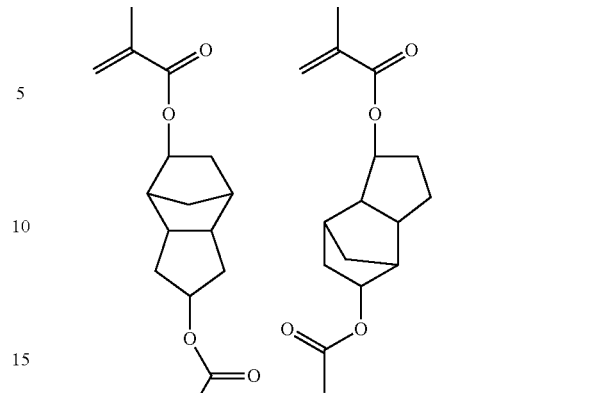
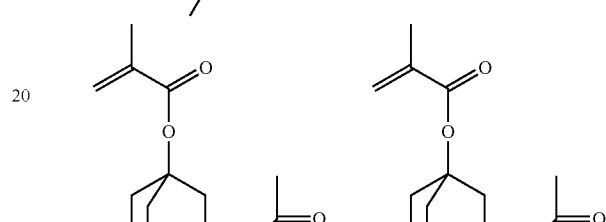
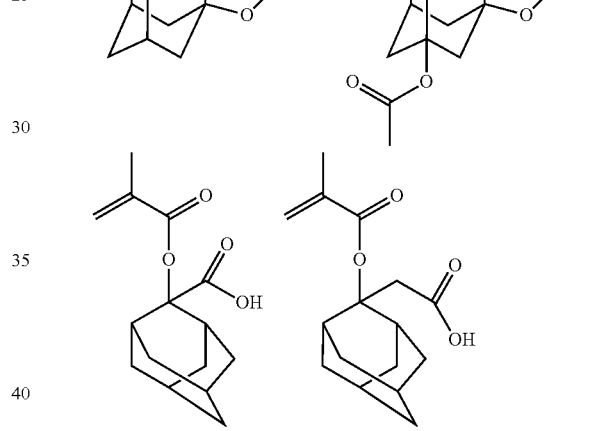
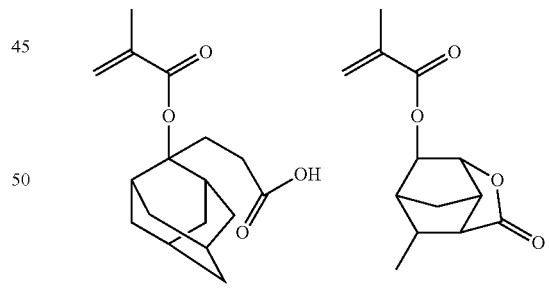
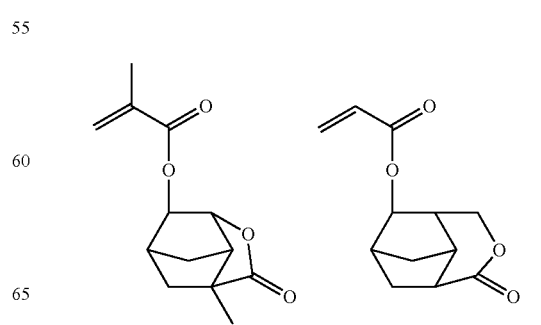

27
-continued
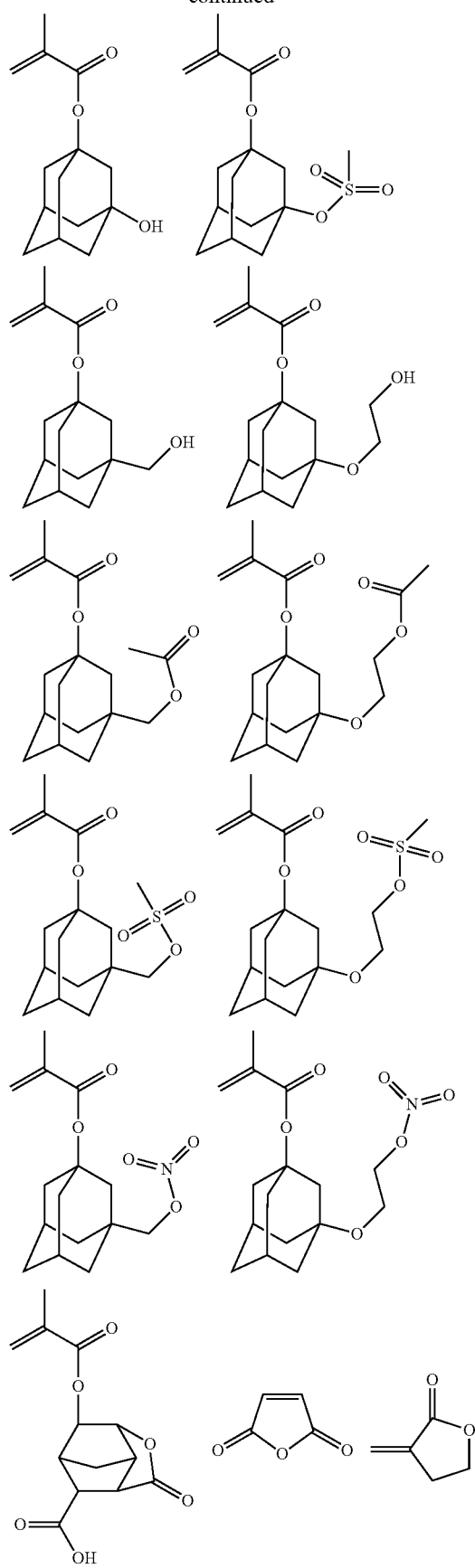
28
-continued
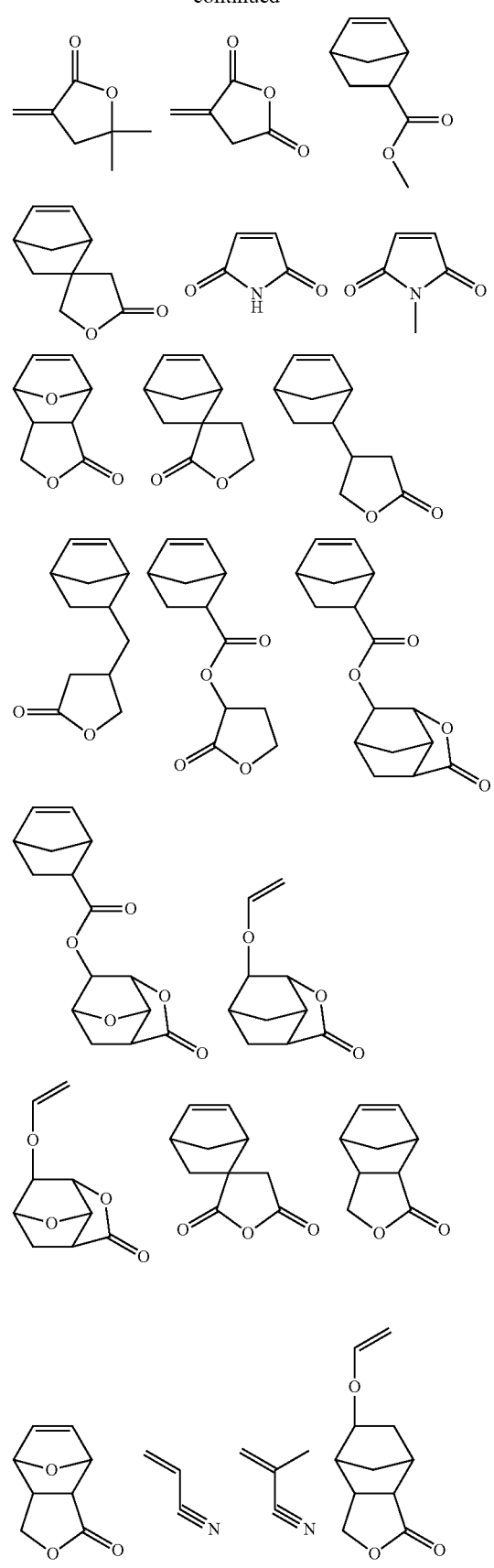

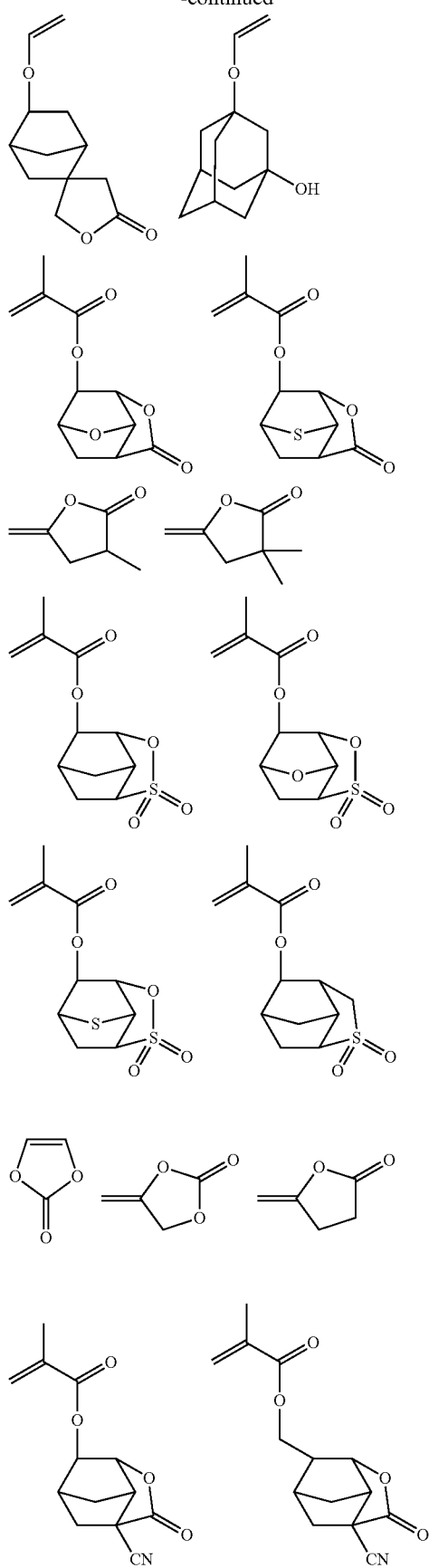
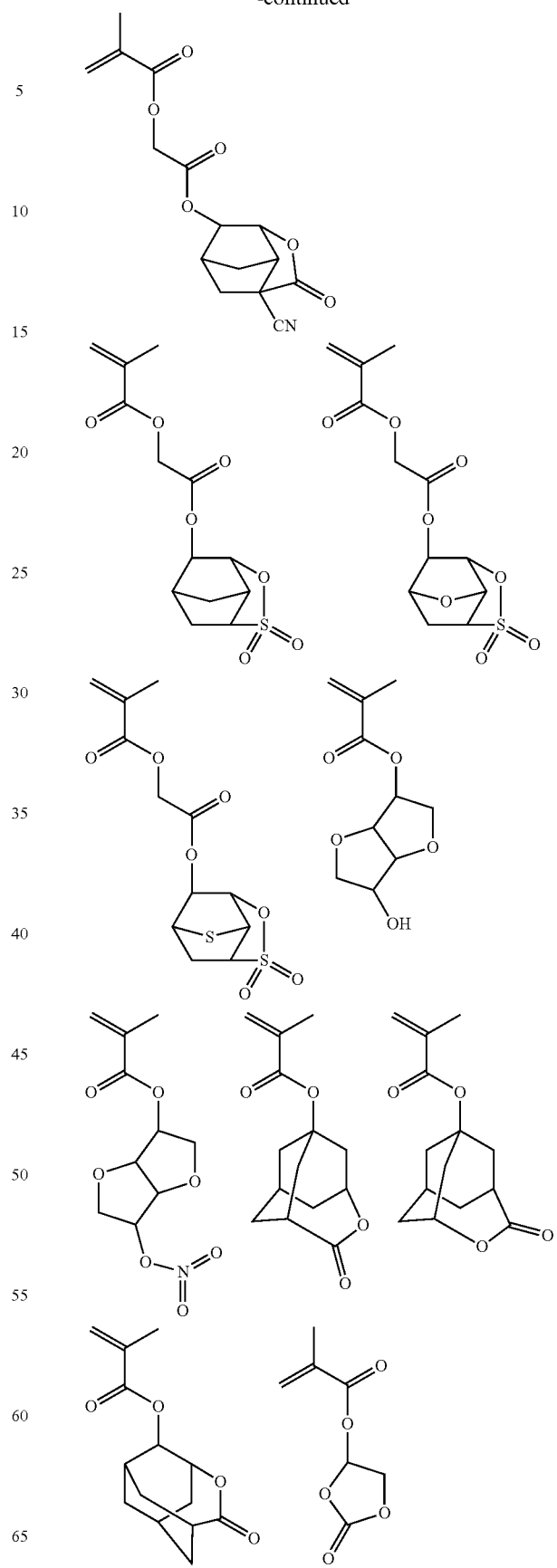

31
-continued
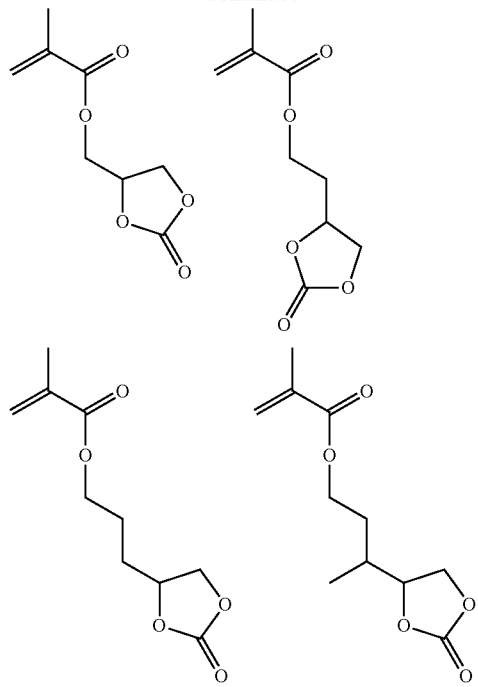
32
-continued
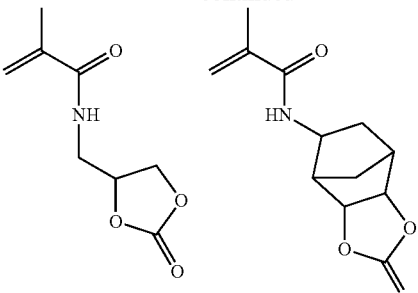
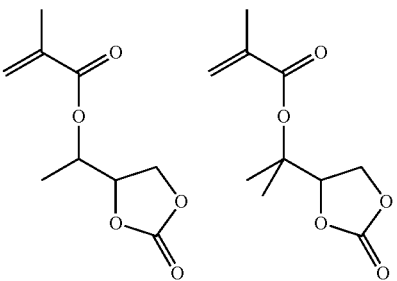
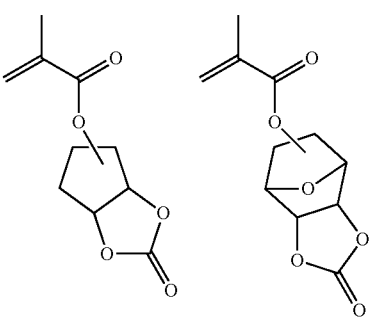
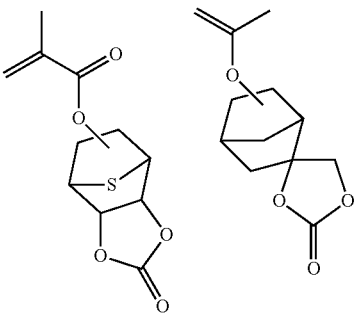
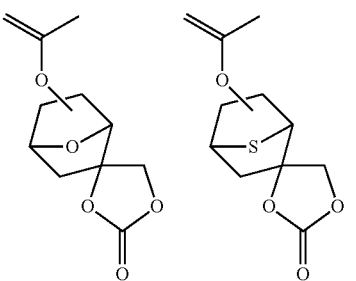

-continued
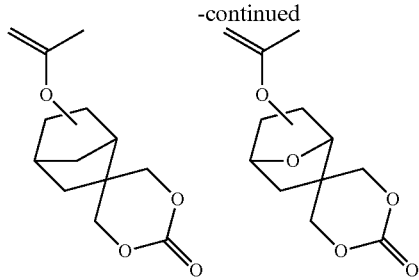
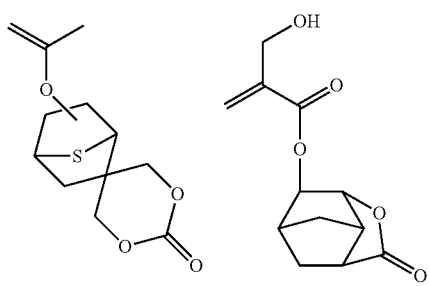
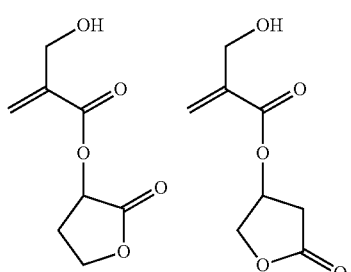
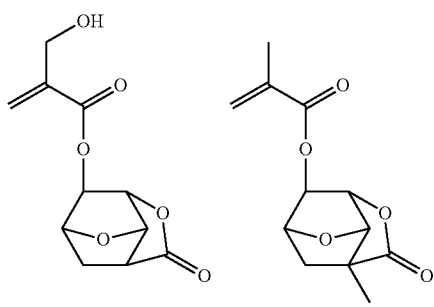
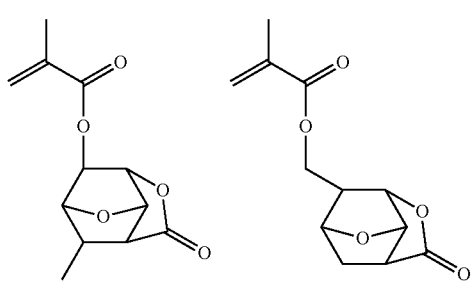
-continued
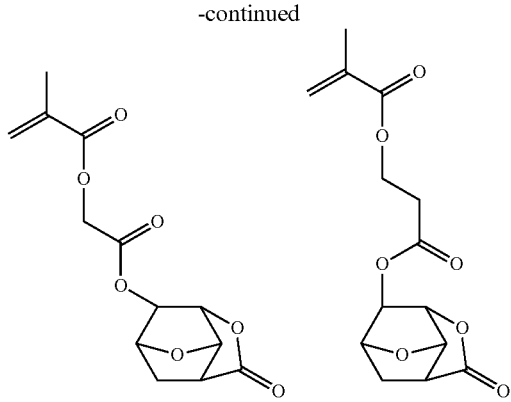
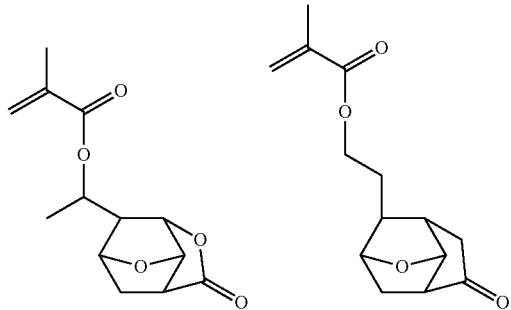
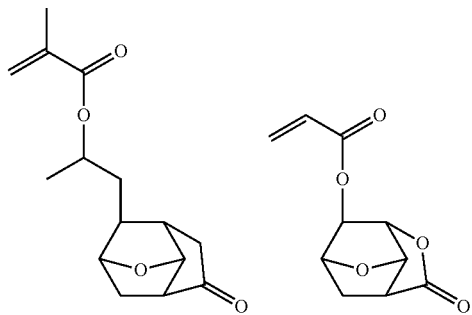
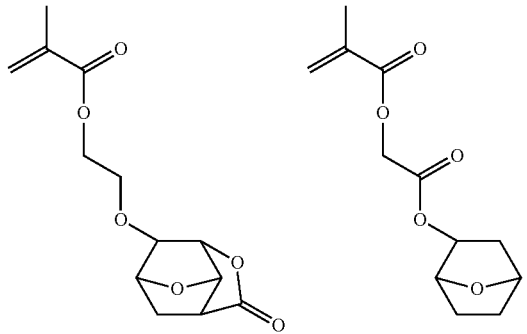
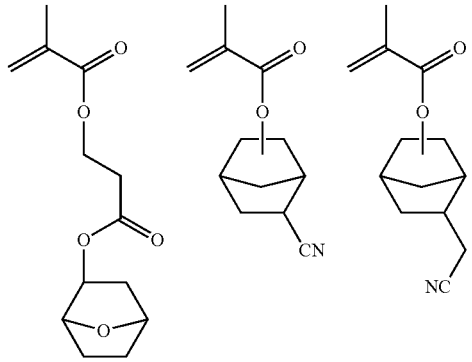

35
-continued
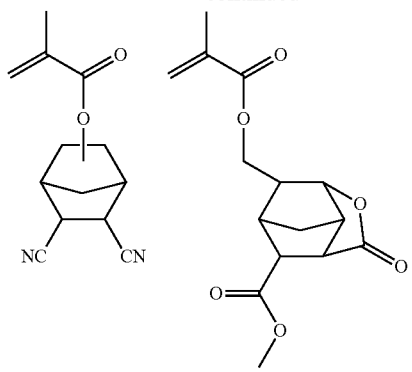
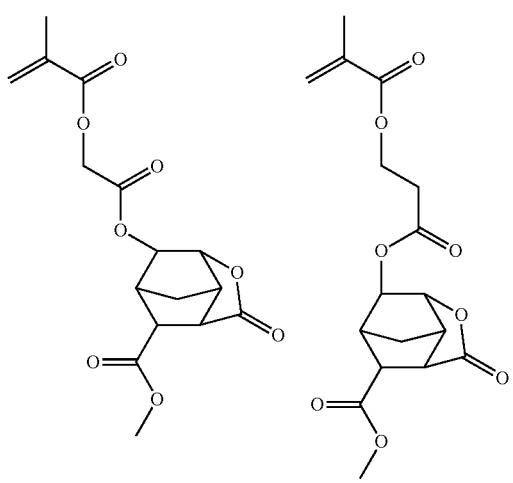
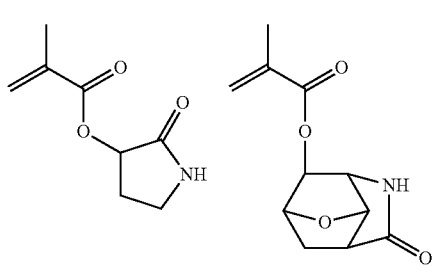
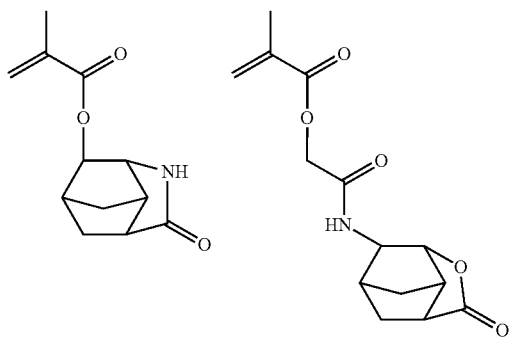
36
-continued
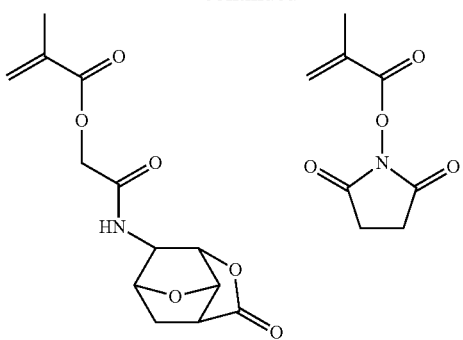
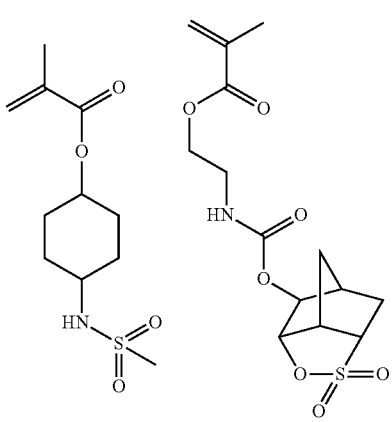
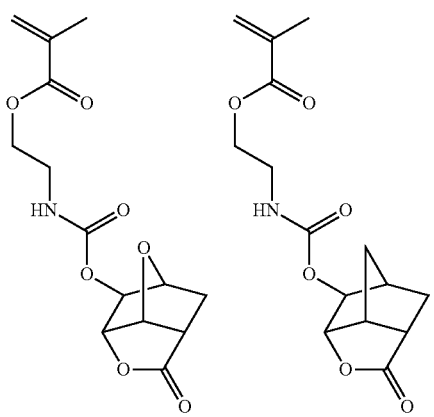
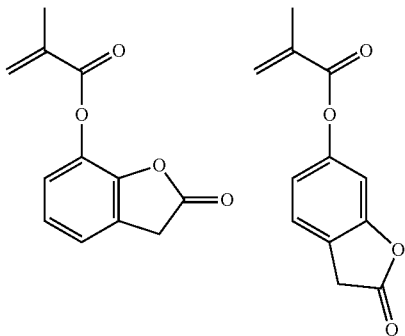

37
-continued
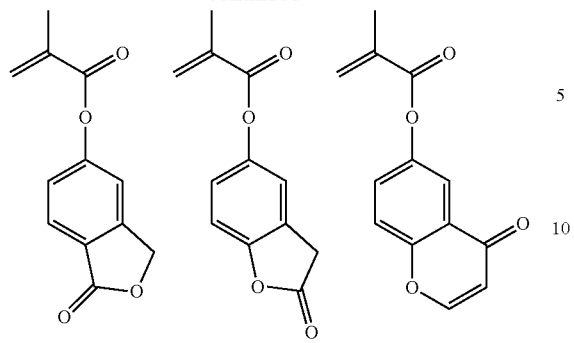
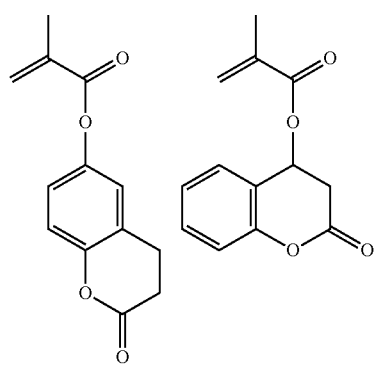
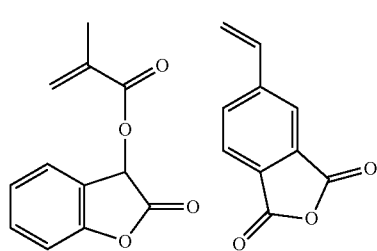
38
-continued
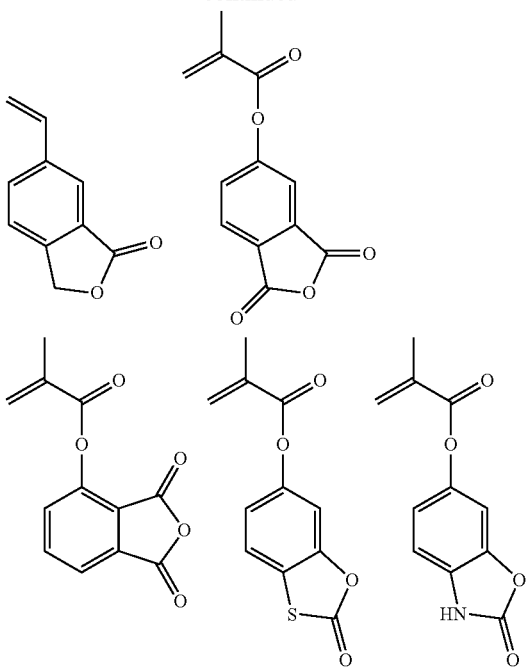
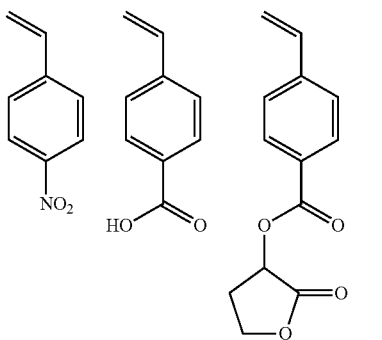
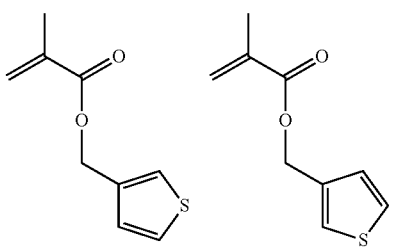
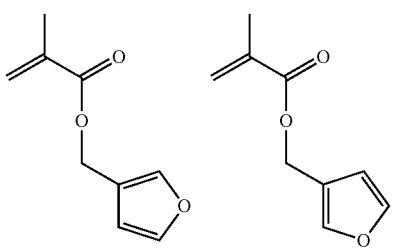
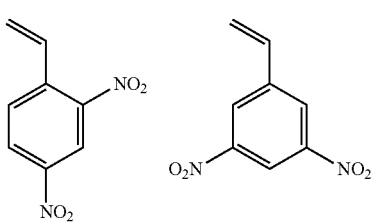

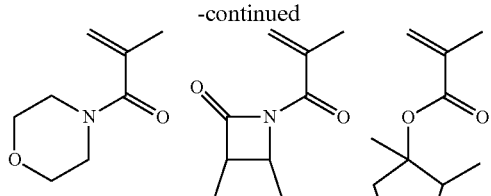
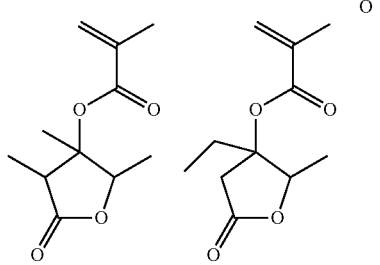
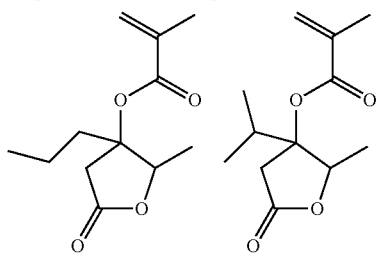
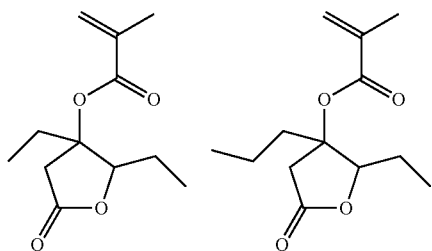
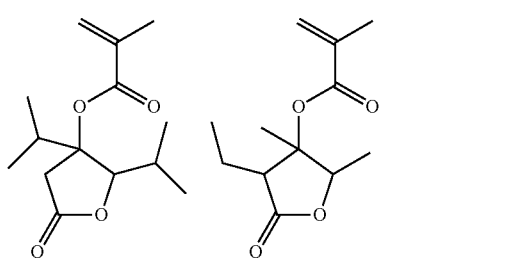
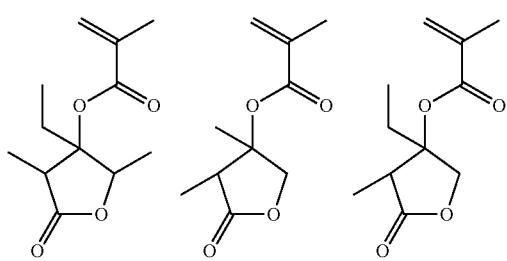
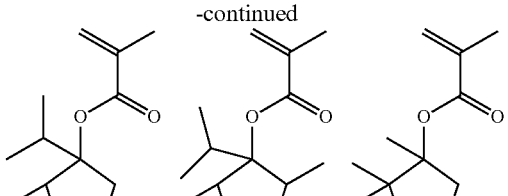
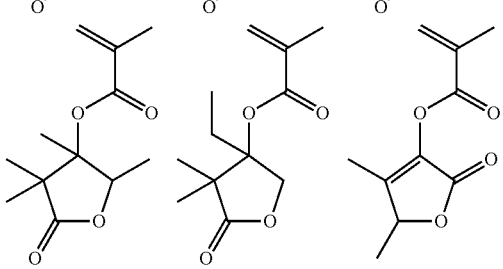
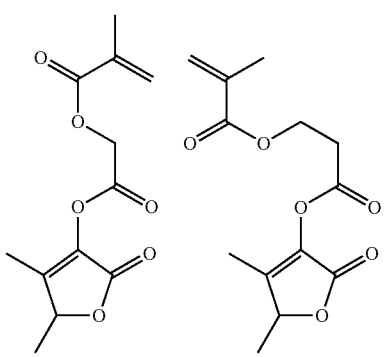
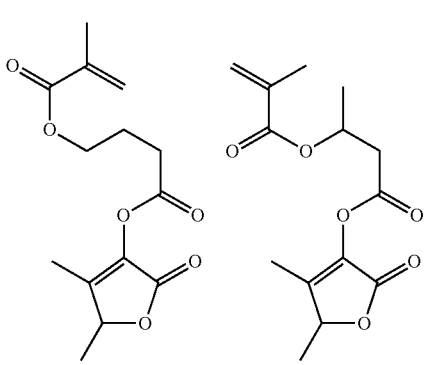
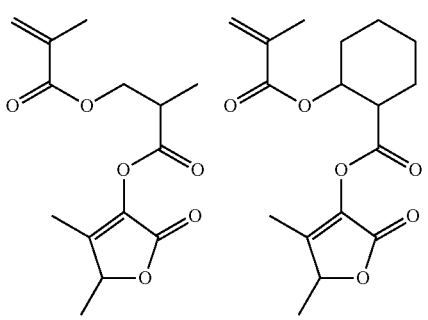

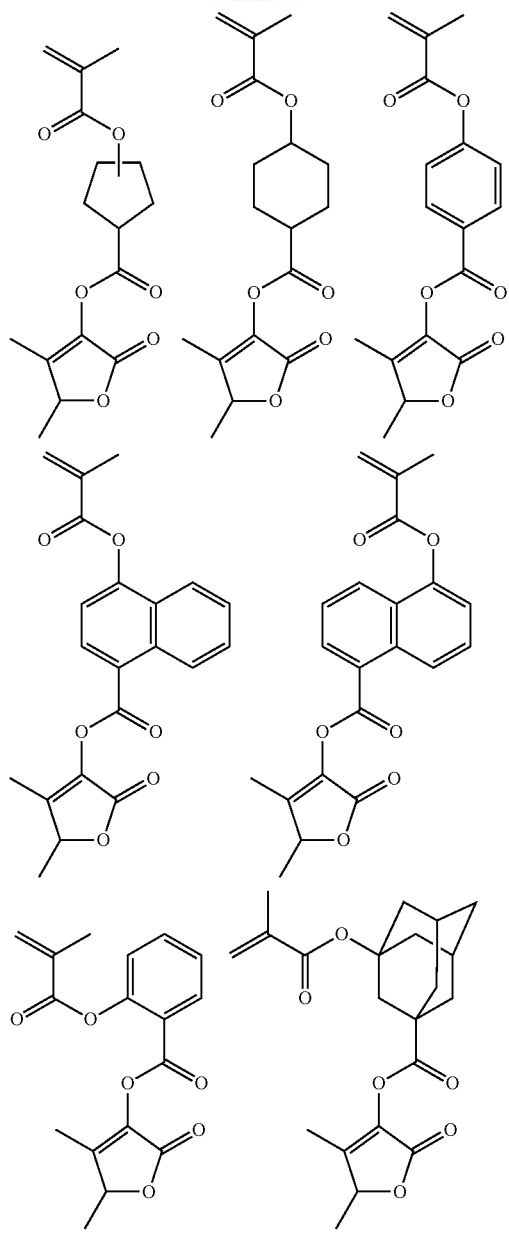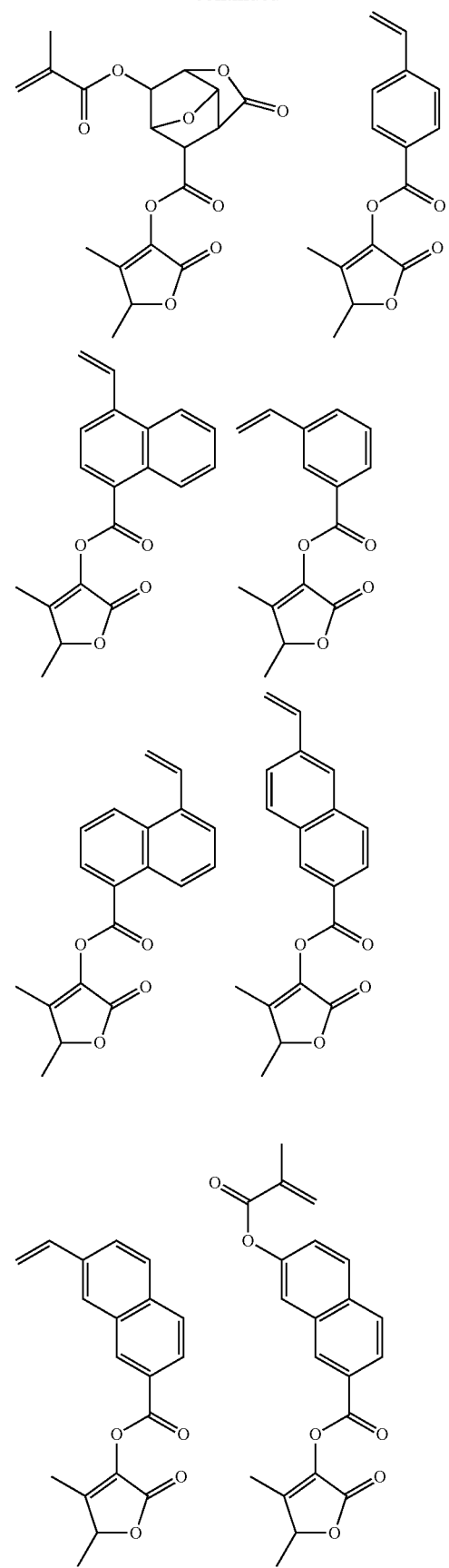

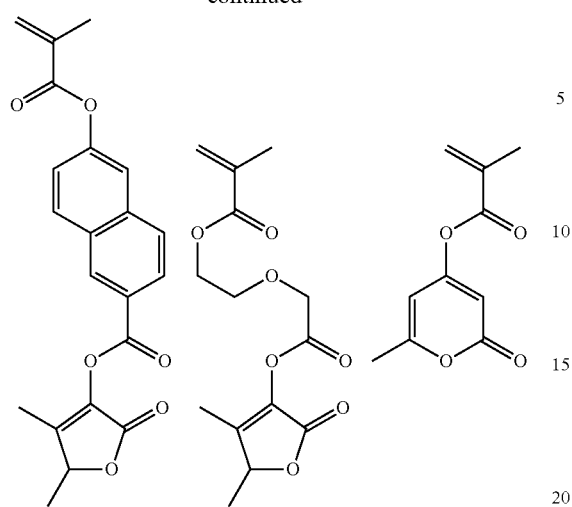
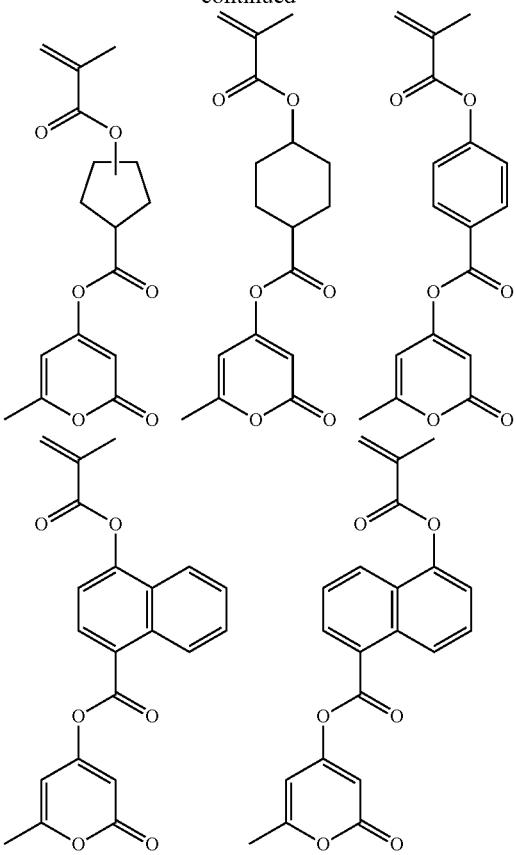
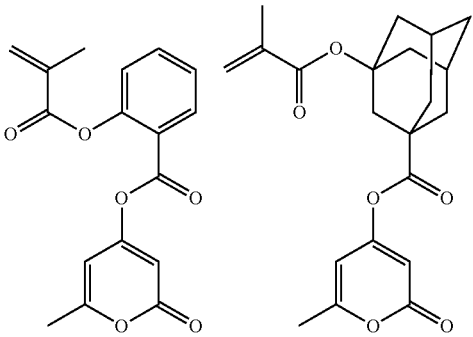
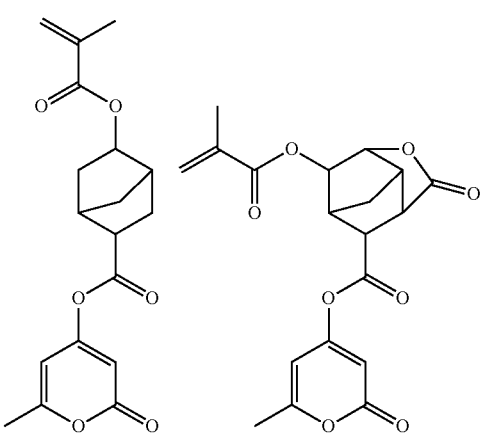

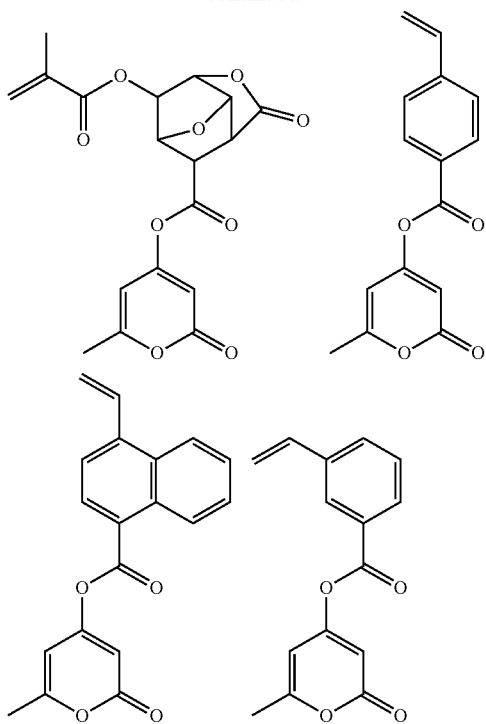
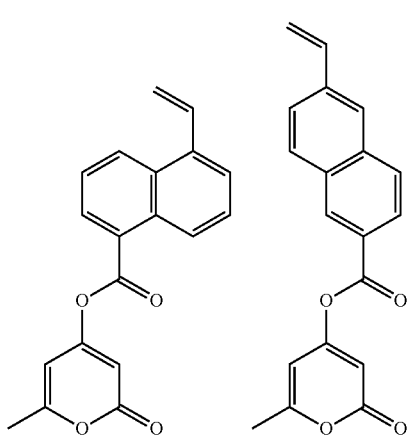
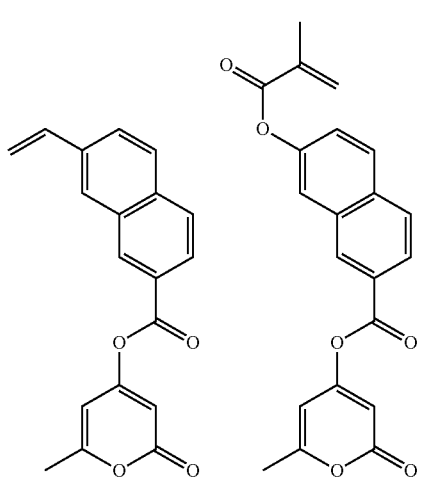
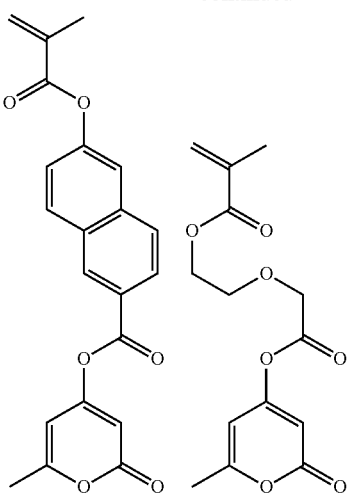

In the polymer comprising the aforementioned recurring units (a1), (a2), (a4), (a5) and (b), additional recurring units may be copolymerized. Exemplary are recurring units (c) having a non-leaving hydrocarbon group as described in JP-A 2008-281980. Suitable non-leaving hydrocarbon groups include those described in JP-A 2008-281980, and indenes, acenaphthylenes, and norbornadienes. By copolymerizing recurring units (c) having a non-leaving hydrocarbon group, the polymer is improved in solubility in the $C_7$-$C_{15}$ ester and $C_8$-$C_{16}$ ketone solvents, and also improved in dry etching resistance when the substrate is etched through the pattern after shrinkage.

Further, recurring units (d) having an oxirane or oxetane ring may be copolymerized. Once recurring units (d) having an oxirane or oxetane ring are copolymerized, crosslinking can take place at the interface between the shrink agent and the resist film, leading to an increase of shrinkage. Examples of the monomers from which recurring units (d) having an oxirane or oxetane ring are derived are shown below. Note that $R^{41}$ is hydrogen or methyl.

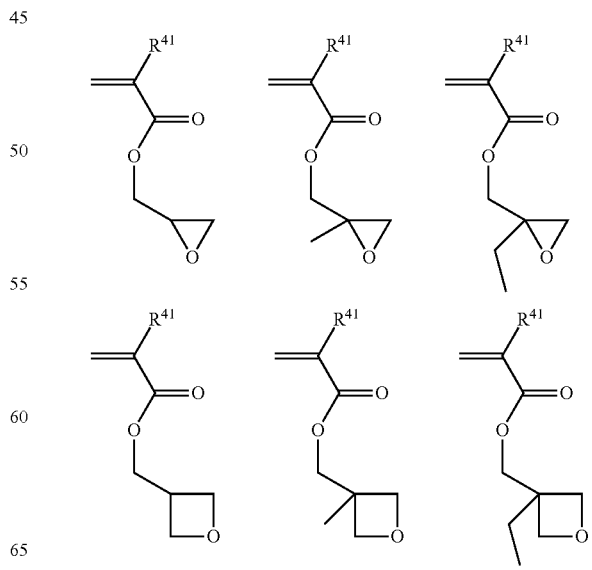

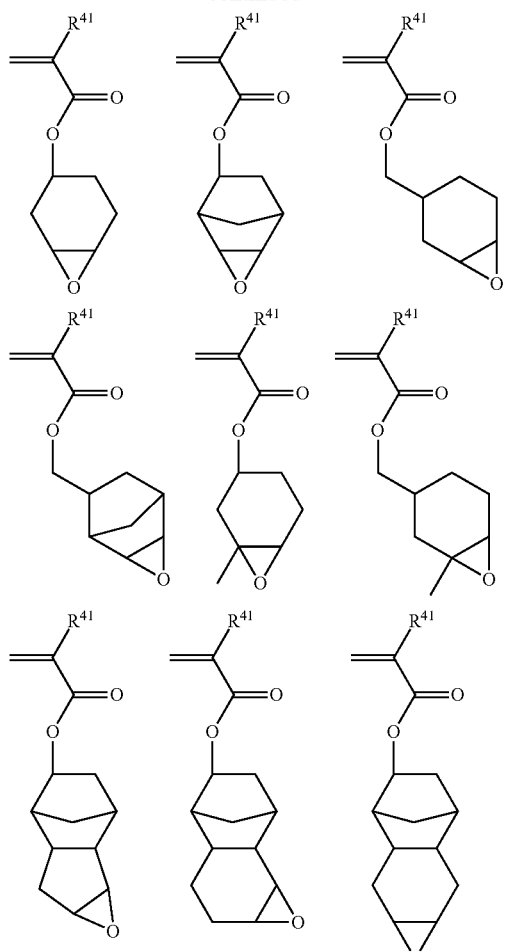
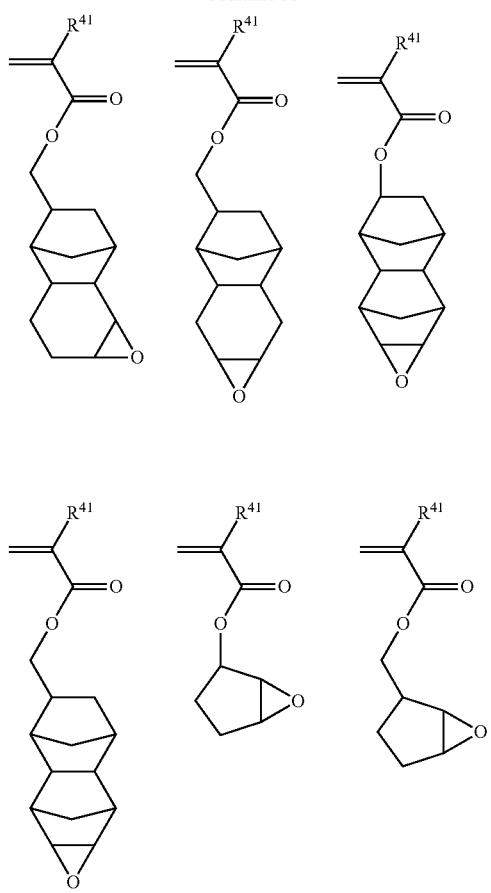
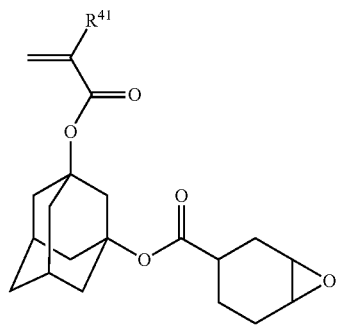
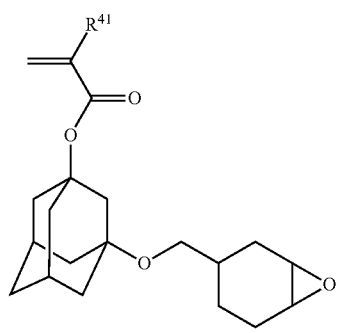

49
-continued
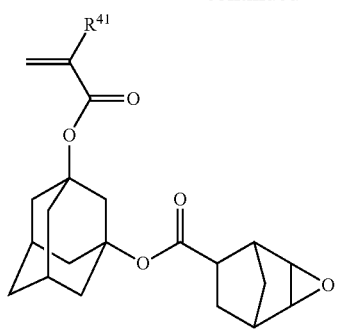
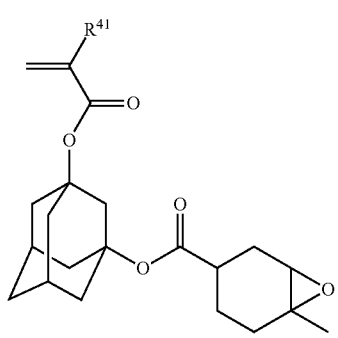
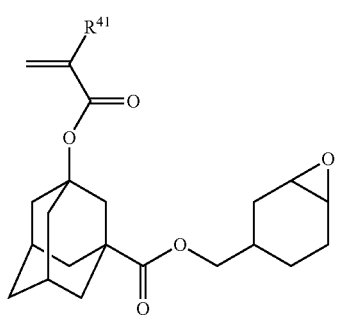
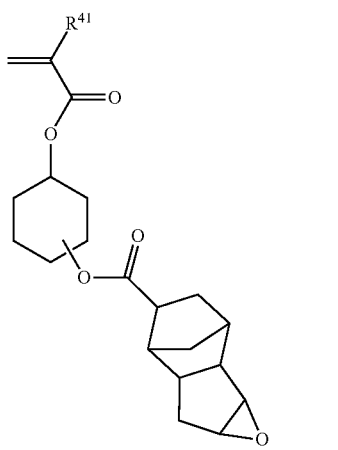
50
-continued
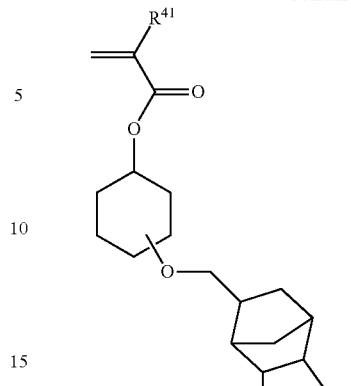
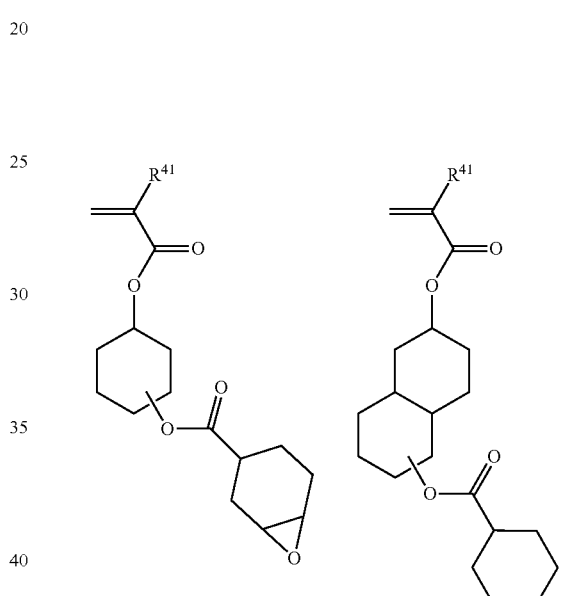
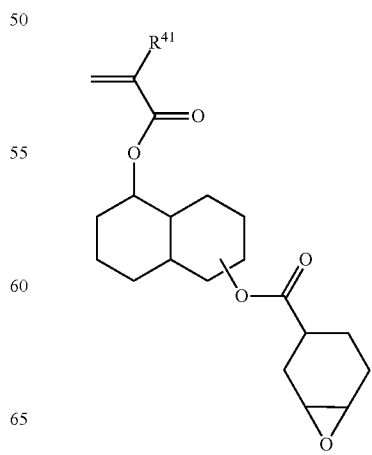

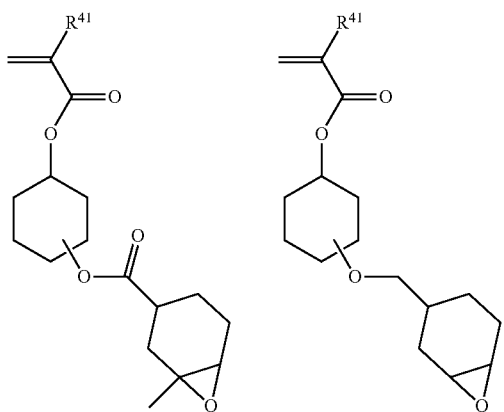
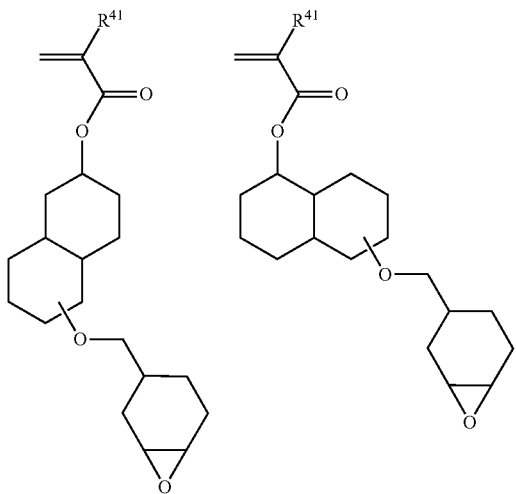
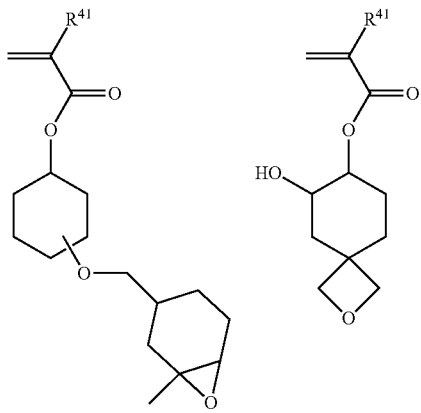
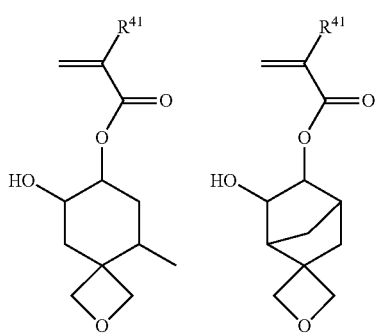
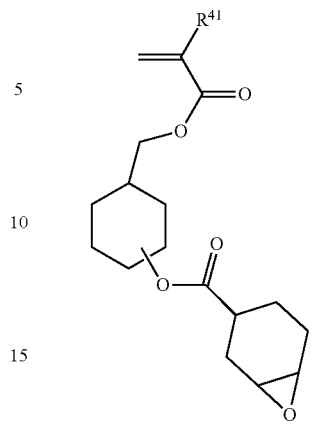

Still further, recurring units (e) having an amino group may be copolymerized. The recurring units (e) having an amino group may have the general formula (5).

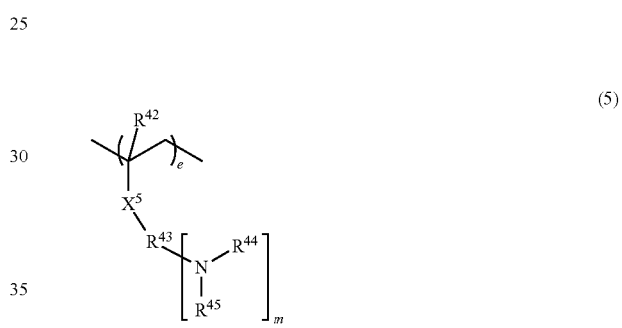

(5)

Herein $R^{42}$ is hydrogen or methyl. $X^5$ is a single bond, phenylene group or —C(=O)—O—. $R^{43}$ is a single bond, a straight, branched or cyclic $C_1$-$C_{10}$ alkylene group which may contain an ether moiety, ester moiety, —N= or —S—, or a phenylene or naphthylene group. $R^{44}$ and $R^{45}$ each are a straight or branched $C_1$-$C_4$ alkyl group, $R^{44}$ and $R^{45}$ may bond together to form a ring which may contain an ether bond, or either one of $R^{44}$ and $R^{45}$ may bond with $R^{43}$ to form a ring; m is 1 or 2, and e is a number of 0≤e≤0.8.

Examples of the monomer from which recurring units (e) having an amino group are derived are shown below. $R^{42}$, $R^{44}$ and $R^{45}$ are as defined above.

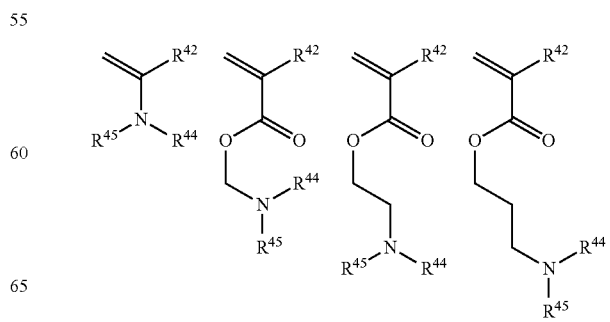

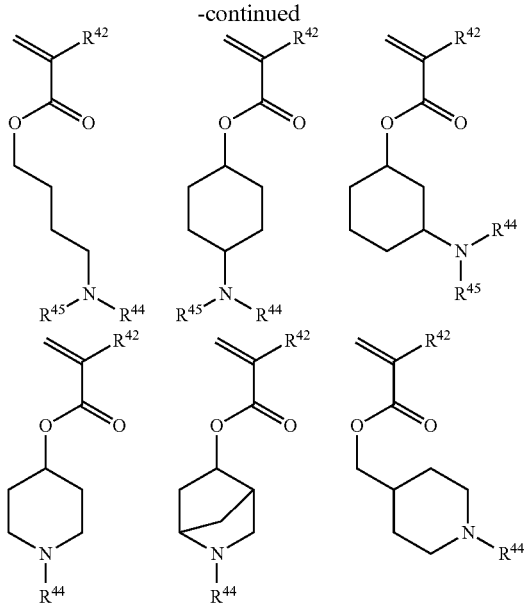
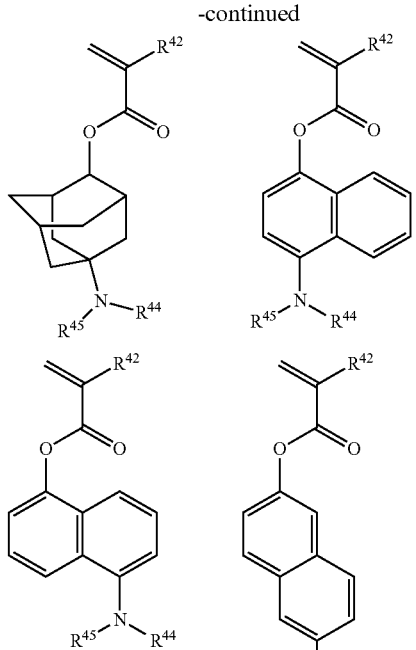
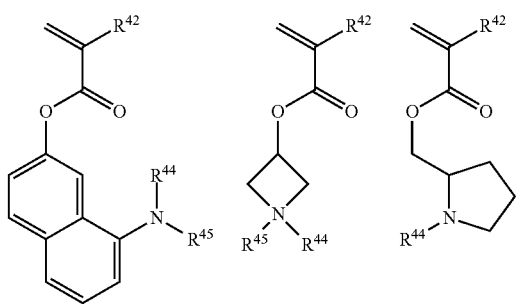
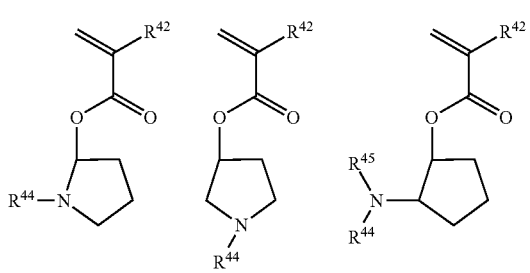
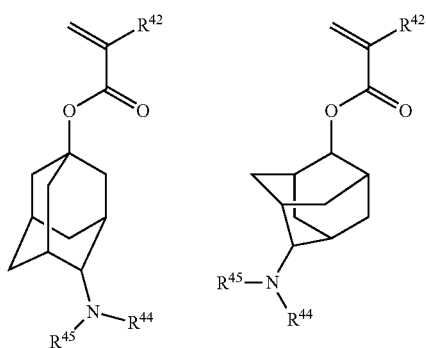

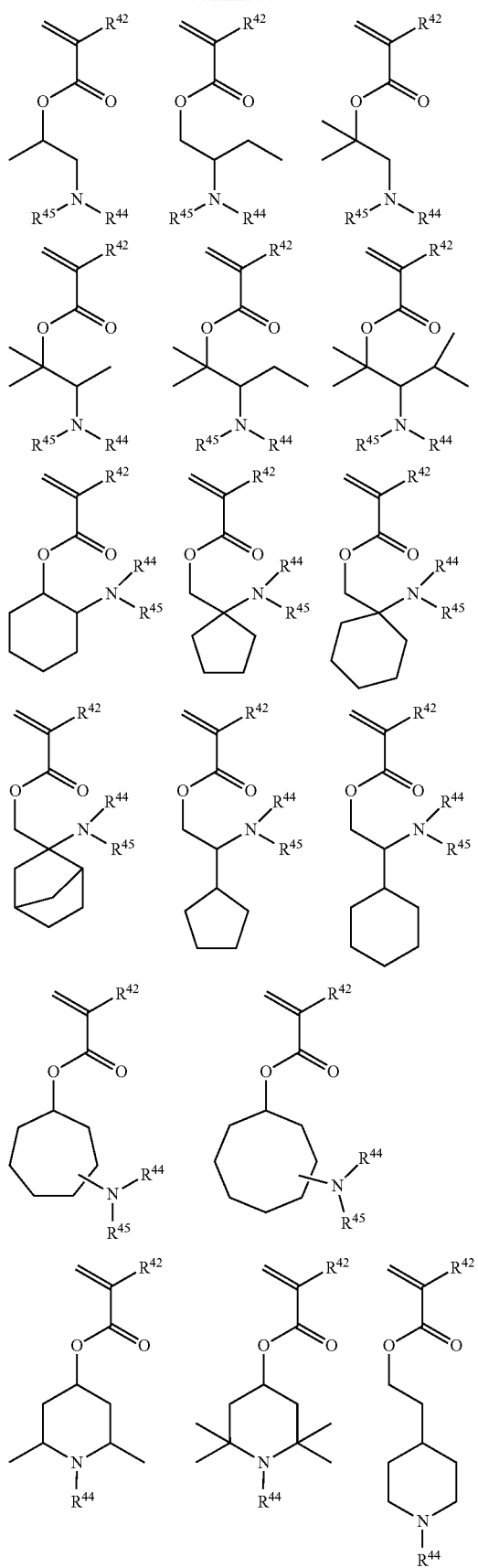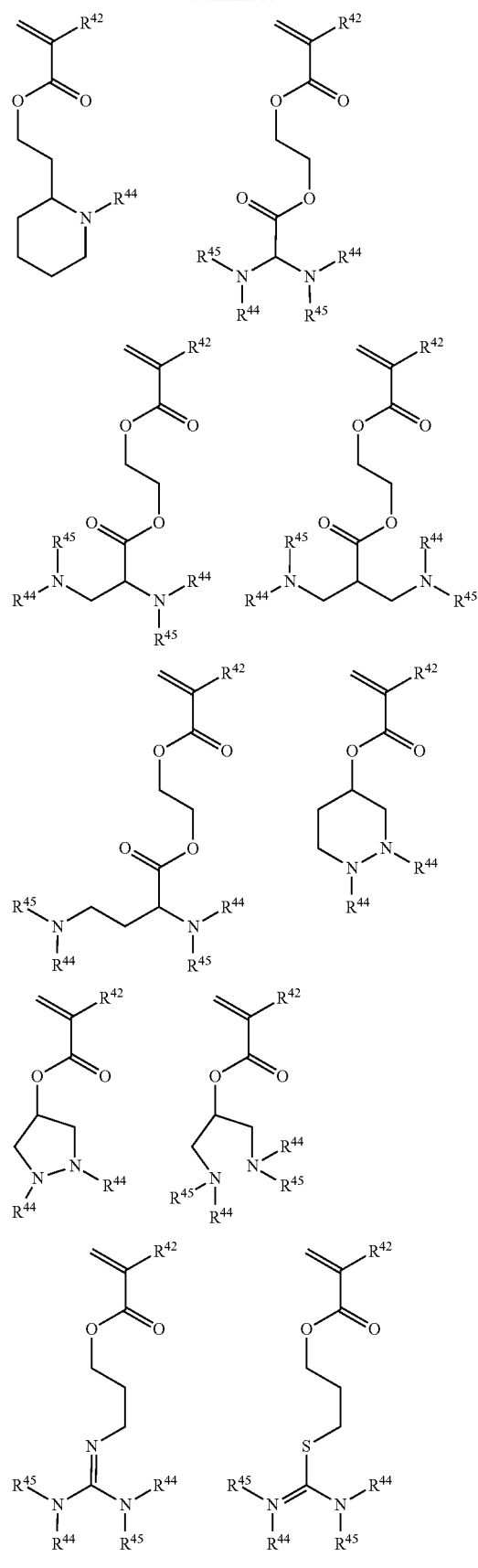

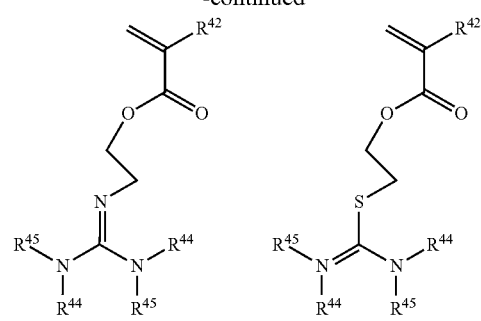
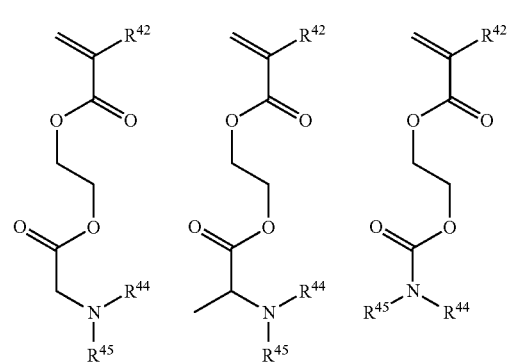
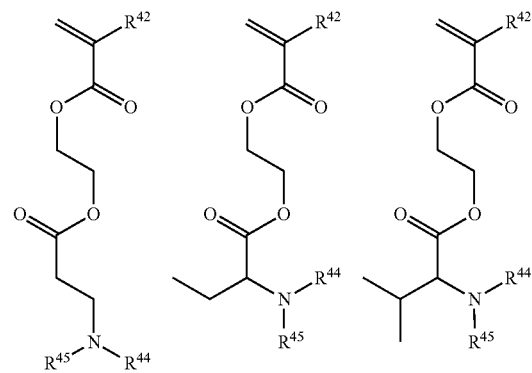
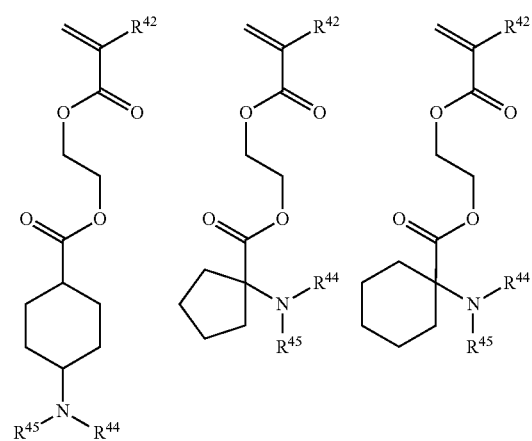
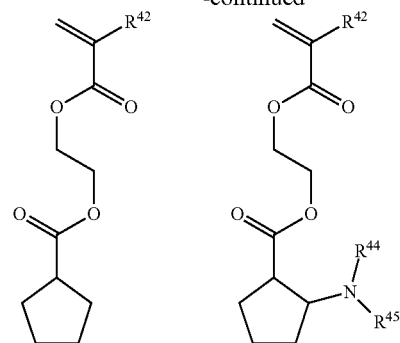
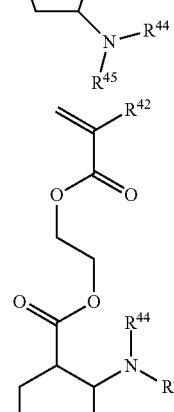
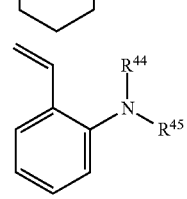
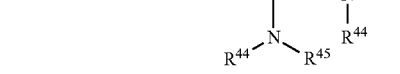
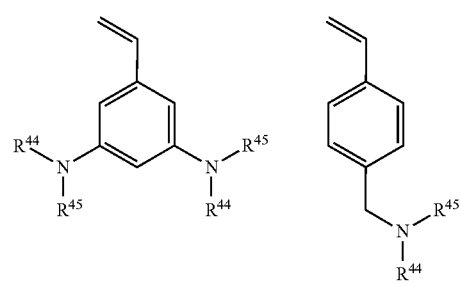
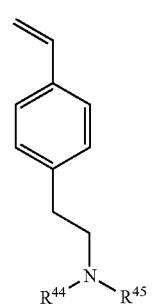

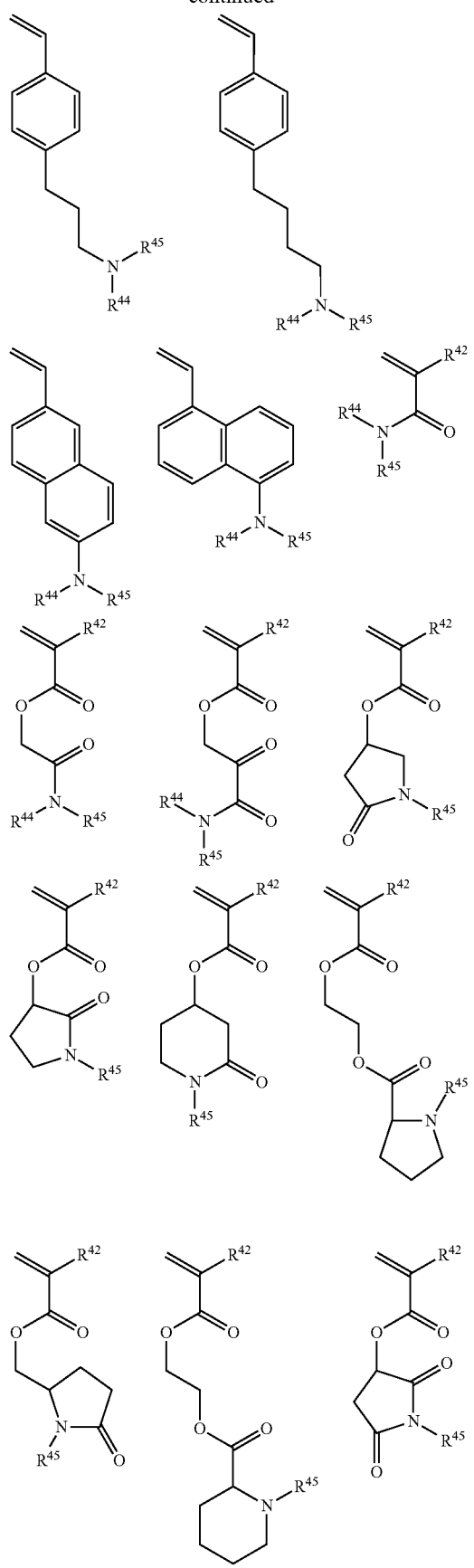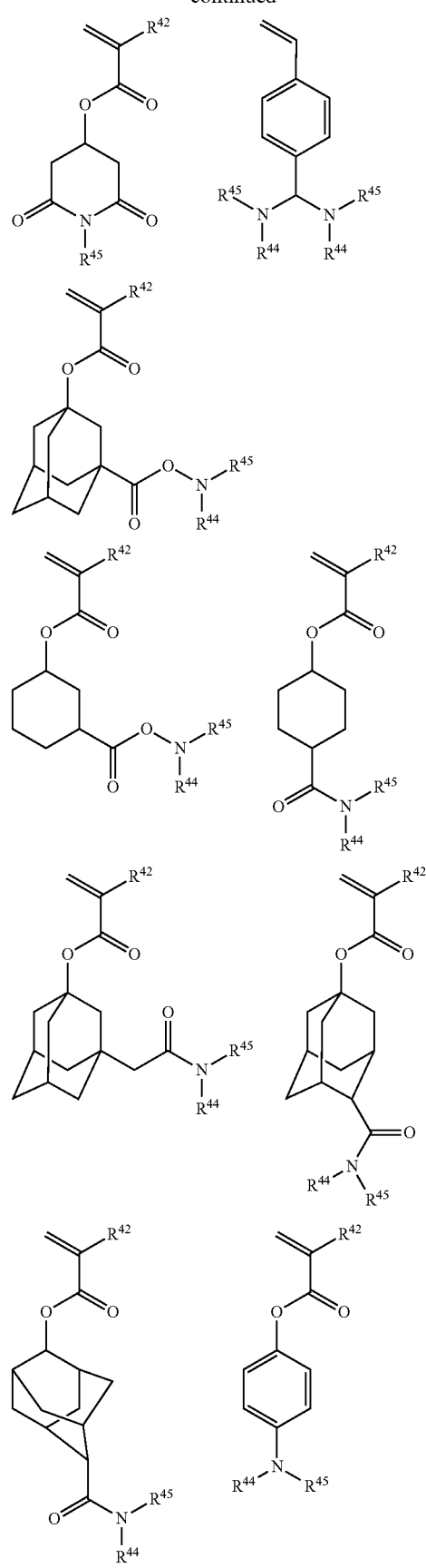

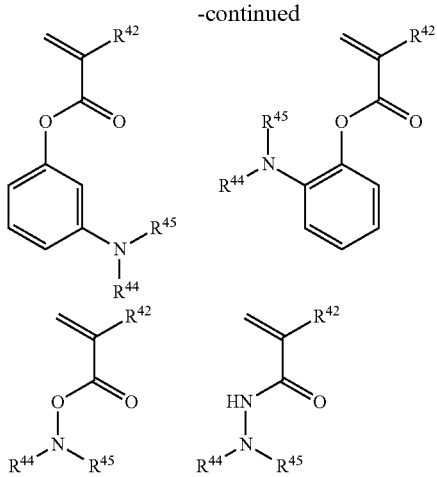

The acid labile group $R^{16}$ substituting on the carboxyl group and the acid labile groups $R^9$ and $R^{19}$ substituting on the hydroxyl group in the base polymer of formulae (1) and (4) for the shrink agent, and the acid labile group $R^{12}$ substituting on the carboxyl group in the base polymer of formula (2) for the photoresist (to be described later) may be selected from a variety of such groups while they may be the same or different. Preferred acid labile groups include groups of formula (AL-10), acetal groups of formula (AL-11), tertiary alkyl groups of formula (AL-12), and oxoalkyl groups of 4 to 20 carbon atoms.

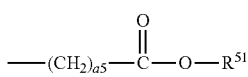 (AL-10)

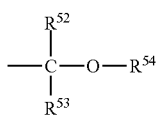 (AL-11)

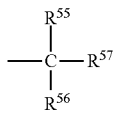 (AL-12)

In formulae (AL-10) and (AL-11), $R^{51}$ and $R^{54}$ each are a monovalent hydrocarbon group, typically a straight, branched or cyclic alkyl group of 1 to 40 carbon atoms, more specifically 1 to 20 carbon atoms, which may contain a heteroatom such as oxygen, sulfur, nitrogen or fluorine. The subscript "a5" is an integer of 0 to 10, preferably 1 to 5. $R^{52}$ and $R^{53}$ each are hydrogen or a monovalent hydrocarbon group, typically a straight, branched or cyclic $C_1$-$C_{20}$ alkyl group, which may contain a heteroatom such as oxygen, sulfur, nitrogen or fluorine. Alternatively, a pair of $R^{52}$ and $R^{53}$, $R^{52}$ and $R^{54}$, or $R^{53}$ and $R^{54}$, taken together, may form a ring, specifically aliphatic ring, with the carbon atom or the carbon and oxygen atoms to which they are attached, the ring having 3 to 20 carbon atoms, especially 4 to 16 carbon atoms.

In formula (AL-12), $R^{55}$, $R^{56}$ and $R^{57}$ each are a monovalent hydrocarbon group, typically a straight, branched or cyclic $C_1$-$C_{20}$ alkyl group, which may contain a heteroatom such as oxygen, sulfur, nitrogen or fluorine. Alternatively, a pair of $R^{55}$ and $R^{56}$, $R^{55}$ and $R^{57}$, or $R^{56}$ and $R^{57}$, taken together, may form a ring, specifically aliphatic ring, with the carbon atom to which they are attached, the ring having 3 to 20 carbon atoms, especially 4 to 16 carbon atoms.

Illustrative examples of the groups of formula (AL-10) include tert-butoxycarbonyl, tert-butoxycarbonylmethyl, tert-amyloxycarbonyl, tert-amyloxycarbonylmethyl, 1-ethoxyethoxycarbonylmethyl, 2-tetrahydropyranyloxy-carbonylmethyl and 2-tetrahydrofuranyloxycarbonylmethyl as well as substituent groups of the following formulae (AL-10)-1 to (AL-10)-10.

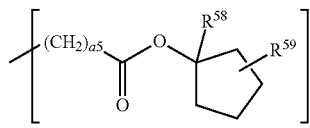 (AL-10)-1

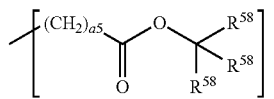 (AL-10)-2

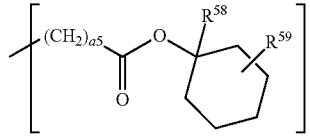 (AL-10)-3

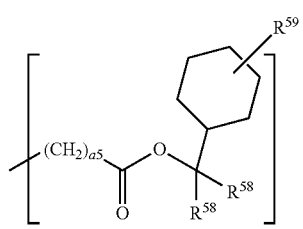 (AL-10)-4

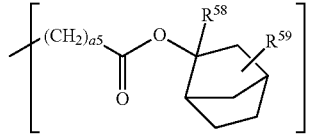 (AL-10)-5

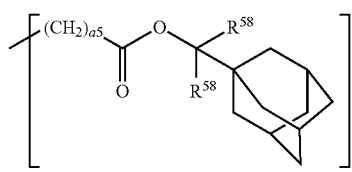 (AL-10)-6

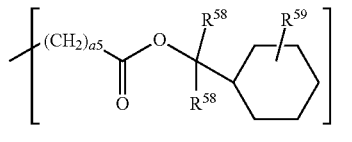 (AL-10)-7

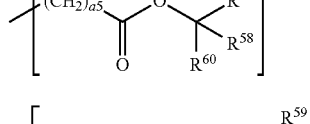 (AL-10)-8

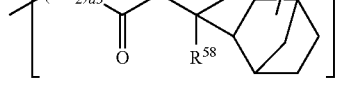 (AL-10)-9

(AL-10)-10

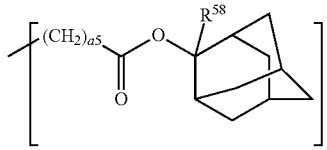

In formulae (AL-10)-1 to (AL-10)-10, $R^{58}$ is independently a straight, branched or cyclic $C_1$-$C_8$ alkyl group, $C_6$-$C_{20}$ aryl group or $C_7$-$C_{20}$ aralkyl group; $R^{59}$ is hydrogen or a straight, branched or cyclic $C_1$-$C_{20}$ alkyl group; $R^{60}$ is a $C_6$-$C_{20}$ aryl group or $C_7$-$C_{20}$ aralkyl group; and "a5" is an integer of 0 to 10 as defined above.

Illustrative examples of the acetal group of formula (AL-11) include those of the following formulae (AL-11)-1 to (AL-11)-112.

—CH$_2$—O—CH$_3$ (AL-11)-1

—CH$_2$—O—CH$_2$—CH$_3$ (AL-11)-2

—CH$_2$—O—(CH$_2$)$_2$—CH$_3$ (AL-11)-3

—CH$_2$—O—(CH$_2$)$_3$—CH$_3$ (AL-11)-4

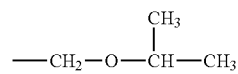 (AL-11)-5

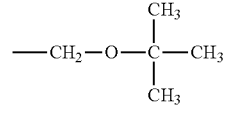 (AL-11)-6

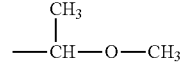 (AL-11)-7

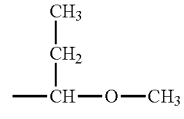 (AL-11)-8

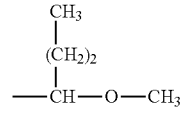 (AL-11)-9

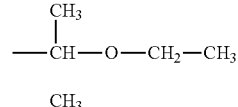 (AL-11)-10

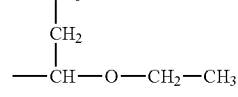 (AL-11)-11

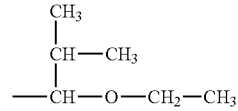 (AL-11)-12

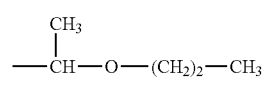 (AL-11)-13

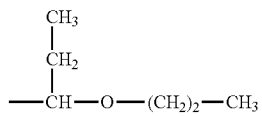 (AL-11)-14

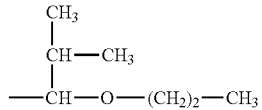 (AL-11)-15

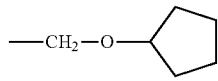 (AL-11)-16

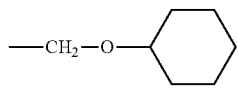 (AL-11)-17

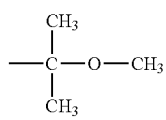 (AL-11)-18

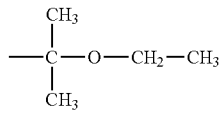 (AL-11)-19

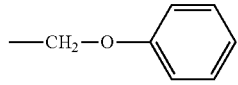 (AL-11)-20

 (AL-11)-21

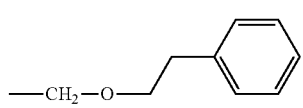 (AL-11)-22

 (AL-11)-23

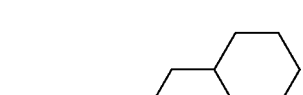 (AL-11)-24

 (AL-11)-25

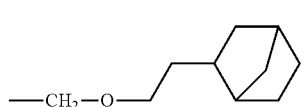 (AL-11)-26

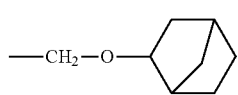 (AL-11)-27

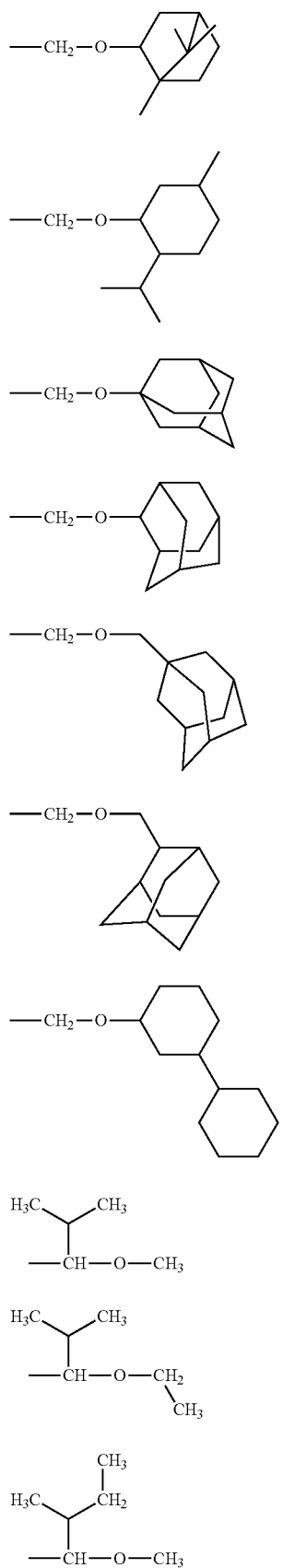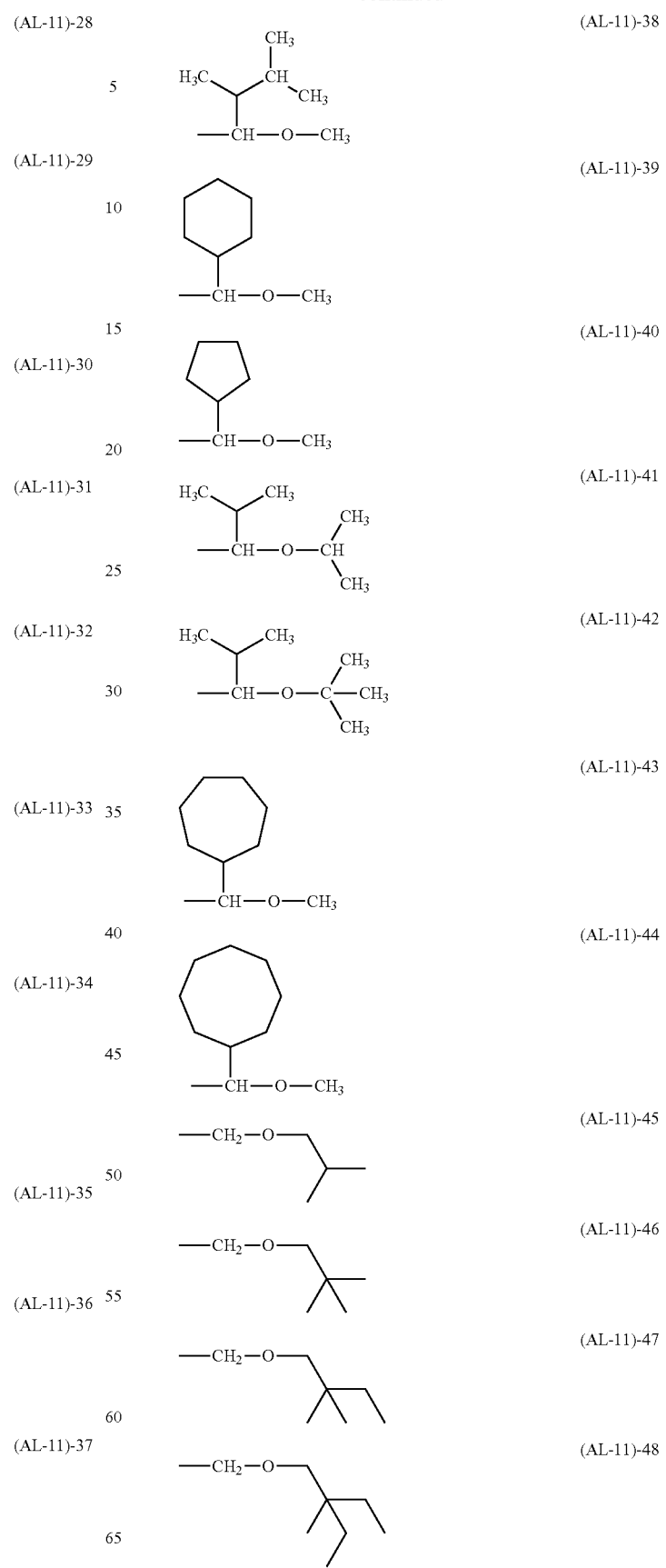

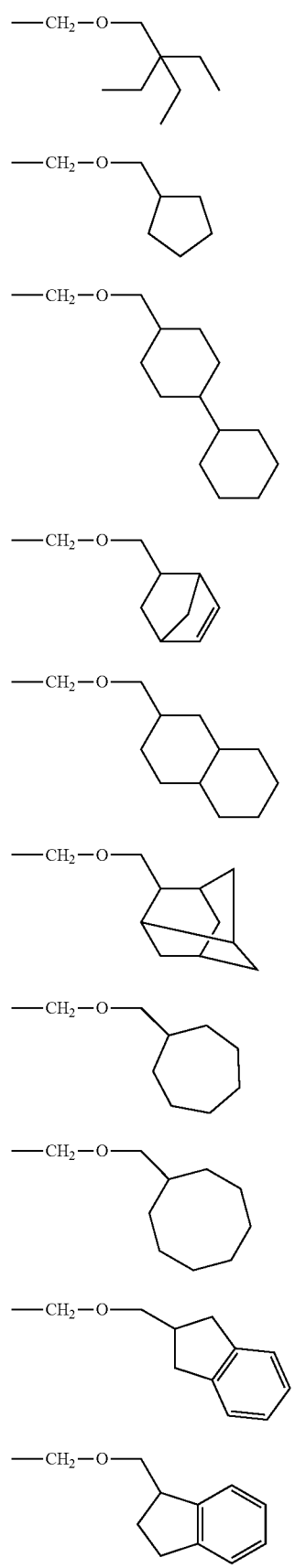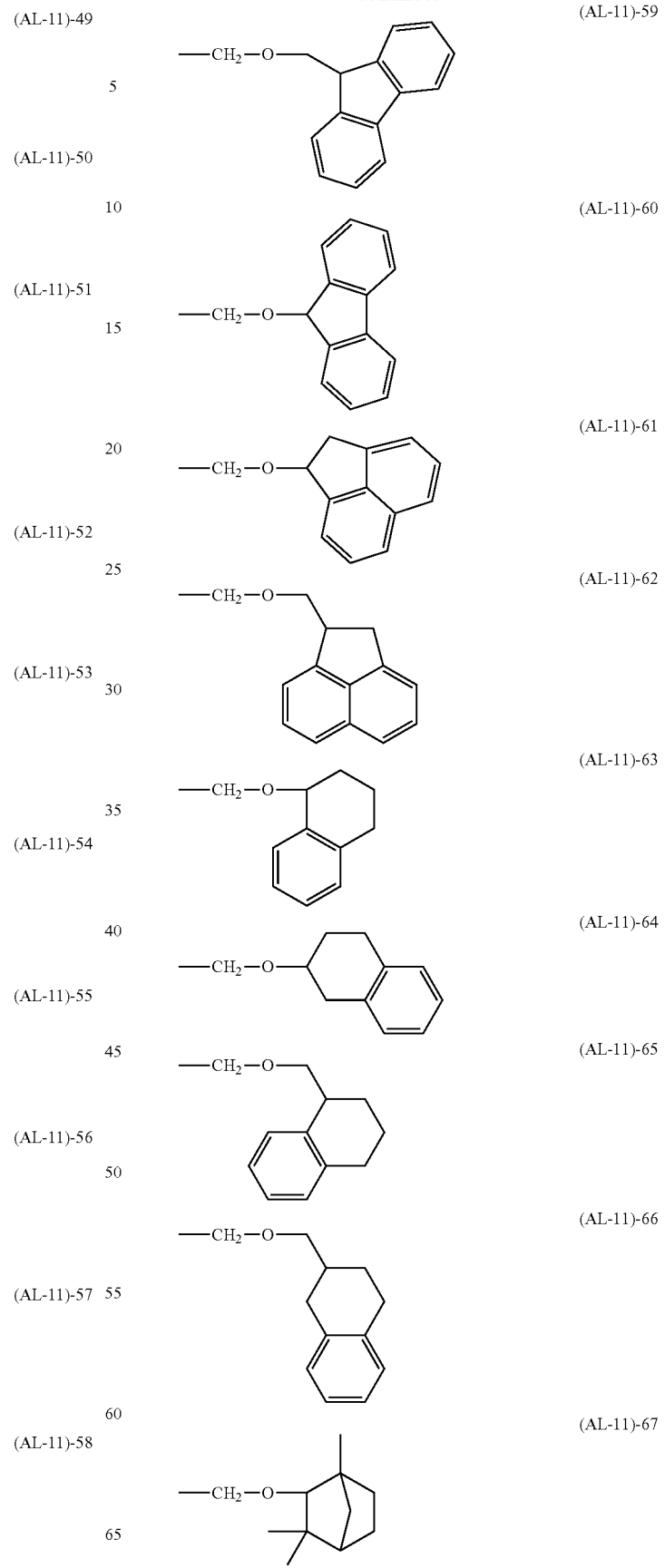

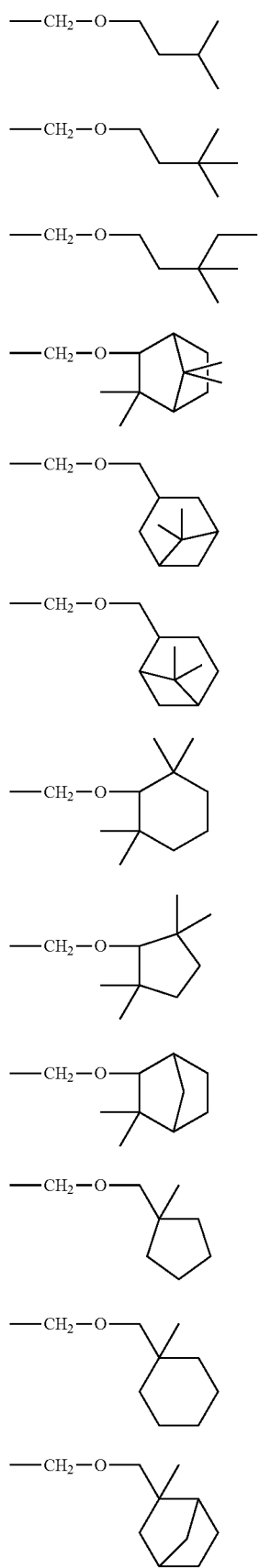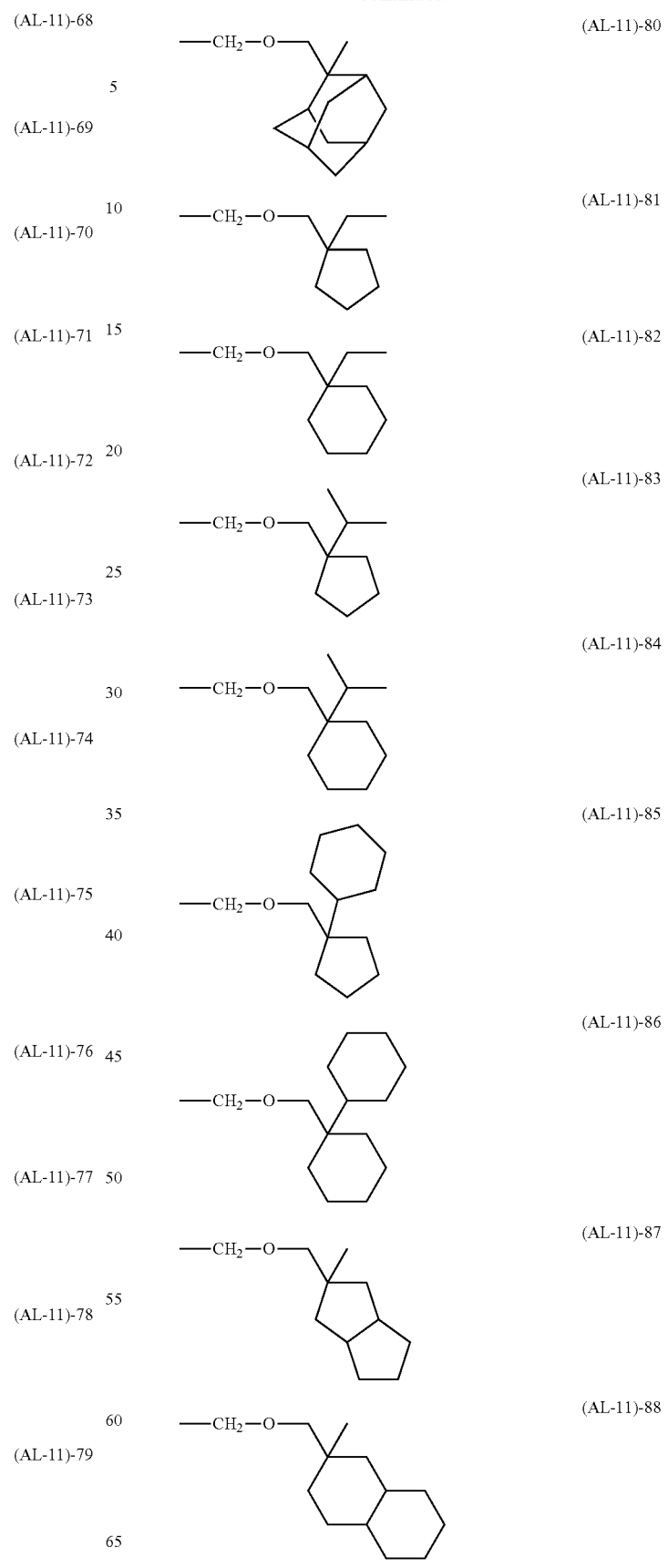

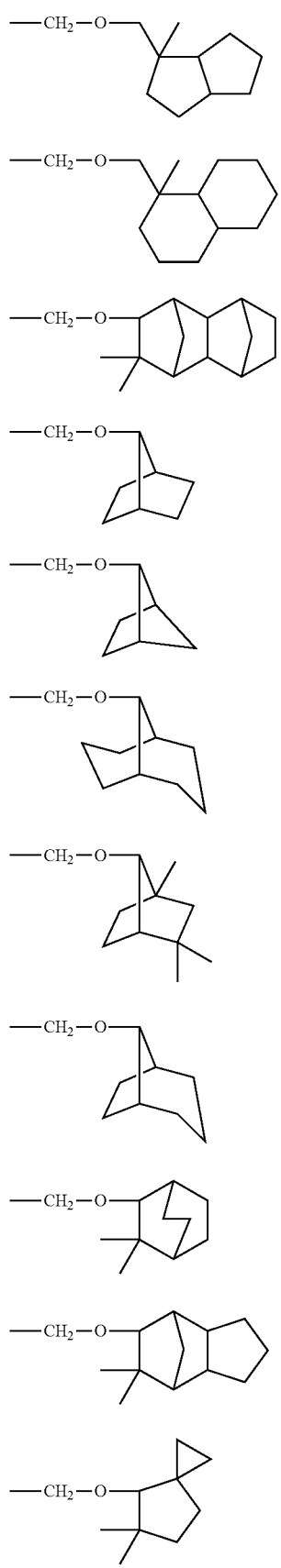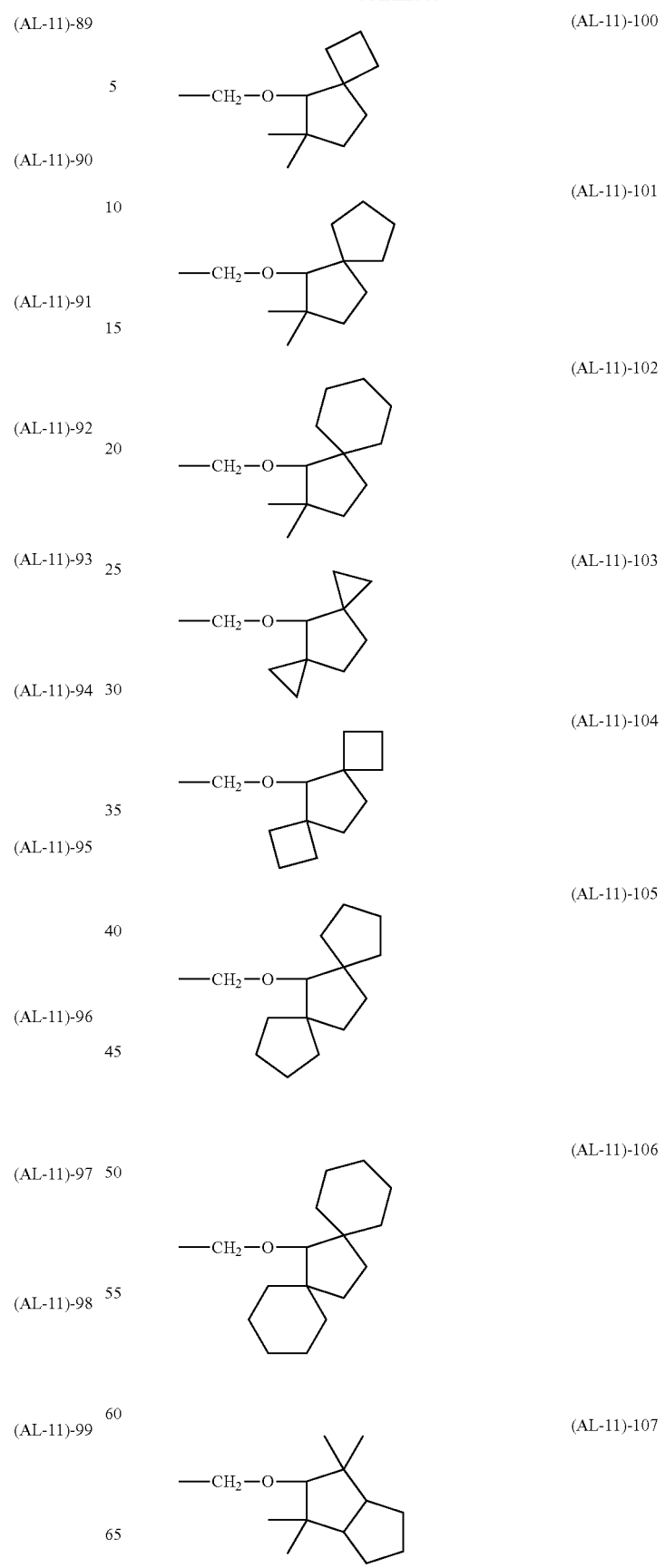

(AL-11)-108 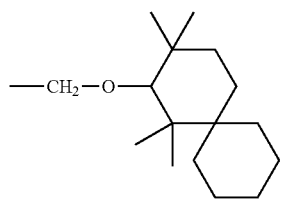

(AL-11)-109 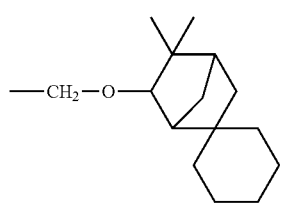

(AL-11)-110 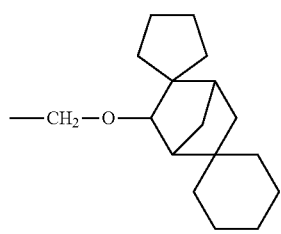

(AL-11)-111 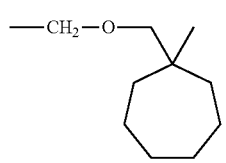

(AL-11)-112 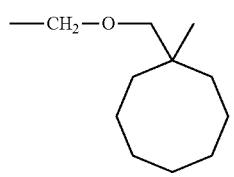

The polymer may be crosslinked within the molecule or between molecules with acid labile groups of formula (AL-11a) or (AL-11b).

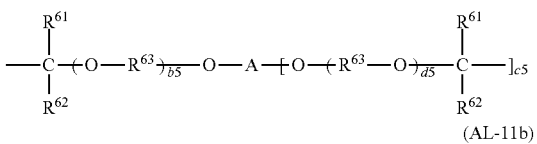

(AL-11a)

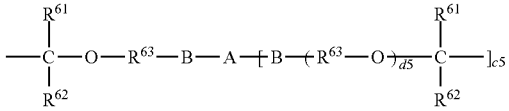

(AL-11b)

Herein $R^{61}$ and $R^{62}$ each are hydrogen or a straight, branched or cyclic $C_1$-$C_8$ alkyl group, or $R^{61}$ and $R^{62}$, taken together, may form a ring with the carbon atom to which they are attached, and $R^{61}$ and $R^{62}$ are straight or branched $C_1$-$C_8$ alkylene groups when they form a ring. $R^{63}$ is a straight, branched or cyclic $C_1$-$C_{10}$ alkylene group. Each of b5 and d5 is 0 or an integer of 1 to 10, preferably 0 or an integer of 1 to 5, and c5 is an integer of 1 to 7. "A" is a (c5+1)-valent aliphatic or alicyclic saturated hydrocarbon group, aromatic hydrocarbon group or heterocyclic group having 1 to 50 carbon atoms, which may be separated by a heteroatom such as oxygen, sulfur or nitrogen or in which some of the hydrogen atoms attached to carbon atoms may be substituted by hydroxyl, carboxyl, carbonyl radicals or fluorine atoms. "B" is —CO—O—, —NHCO—O— or —NHCONH—.

Preferably, "A" is selected from divalent to tetravalent, straight, branched or cyclic $C_1$-$C_{20}$ alkylene, alkanetriyl and alkanetetrayl groups, and $C_6$-$C_{30}$ arylene groups, which may be separated by a heteroatom such as oxygen, sulfur or nitrogen or in which some of the hydrogen atoms attached to carbon atoms may be substituted by hydroxyl, carboxyl, acyl radicals or halogen atoms. The subscript c5 is preferably an integer of 1 to 3.

The crosslinking acetal groups of formulae (AL-11a) and (AL-11b) are exemplified by the following formulae (AL-11)-113 through (AL-11)-120.

(AL-11)-113 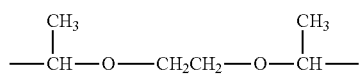

(AL-11)-114 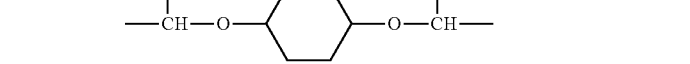

(AL-11)-115 

(AL-11)-116 

(AL-11)-117 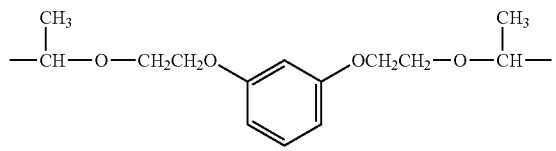

(AL-11)-118 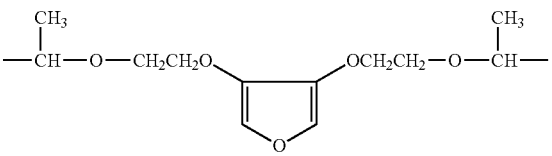

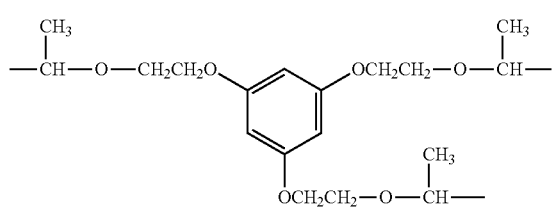
(AL-11)-119
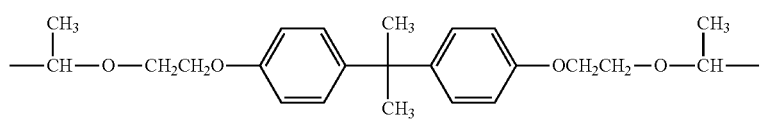
(AL-11)-120
Illustrative examples of the tertiary alkyl of formula (AL-12) include tert-butyl, triethylcarbyl, 1-ethylnorbornyl, 1-methylcyclohexyl, 1-ethylcyclopentyl, and tert-amyl groups as well as those of (AL-12)-1 to (AL-12)-16.
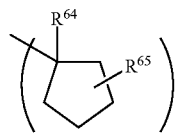
(AL-12)-1
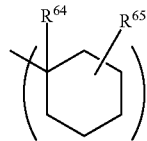
(AL-12)-2
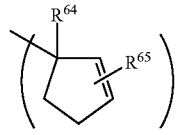
(AL-12)-3
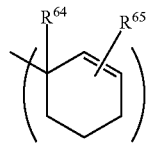
(AL-12)-4
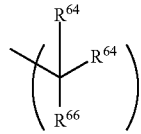
(AL-12)-5
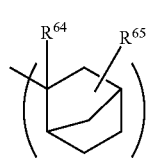
(AL-12)-6
-continued
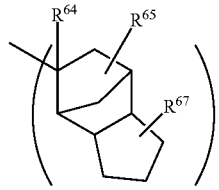
(AL-12)-7
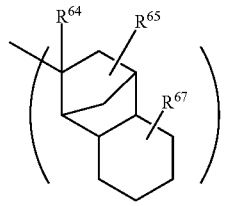
(AL-12)-8
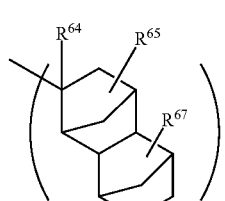
(AL-12)-9
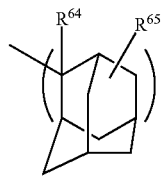
(AL-12)-10
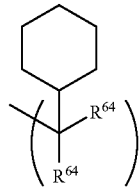
(AL-12)-11
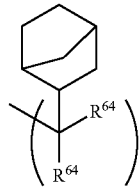
(AL-12)-12

(AL-12)-13
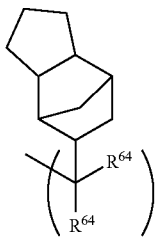

(AL-12)-14
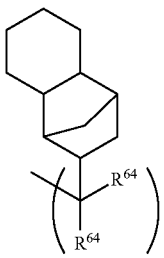

(AL-12)-15
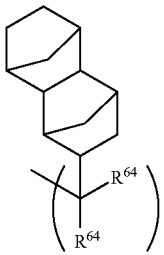

(AL-12)-16
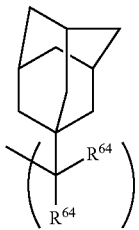

Herein $R^{64}$ is independently a straight, branched or cyclic $C_1$-$C_8$ alkyl, $C_6$-$C_{20}$ aryl or $C_7$-$C_{20}$ aralkyl group, or two $R^{64}$ may bond together to form a ring. $R^{65}$ and $R^{67}$ each are hydrogen, methyl or ethyl. $R^{66}$ is a $C_6$-$C_{20}$ aryl or $C_7$-$C_{20}$ aralkyl group.

Also included are acid labile groups of the formula (AL-12)-17.

(AL-12)-17
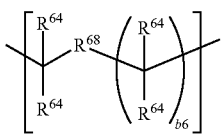

Herein $R^{64}$ is as defined above, $R^{68}$ is a single bond or a straight, branched or cyclic $C_1$-$C_{20}$ alkylene group or arylene group which may contain a heteroatom such as oxygen, sulfur or nitrogen, and b6 is an integer of 0 to 3. With acid labile groups of formula (AL-12)-17 containing $R^{68}$ representative of a di- or poly-valent alkylene or arylene group, the polymer may be crosslinked within the molecule or between molecules. It is noted that formula (AL-12)-17 is applicable to all the foregoing acid labile groups $R^9$, $R^{12}$, $R^{16}$ and $R^{19}$.

The groups represented by $R^{64}$, $R^{65}$, $R^{66}$ and $R^{67}$ may contain a heteroatom such as oxygen, nitrogen or sulfur. Such groups are exemplified by those of the following formulae (AL-13)-1 to (AL-13)-7.

(AL-13)-1
—$(CH_2)_4OH$ (AL-13)-2
—$(CH_2)_2O(CH_2)_3CH_3$ (AL-13)-3
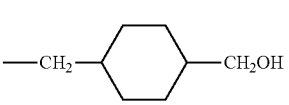

(AL-13)-4
—$(CH_2)_2O(CH_2)_2OH$ (AL-13)-5
—$(CH_2)_6OH$ (AL-13)-6
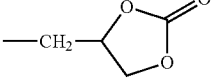

(AL-13)-7
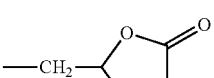

Of the acid labile groups of formula (AL-12), groups of exo-form structure having the following formula (AL-12)-19 are preferred.

(AL-12)-19
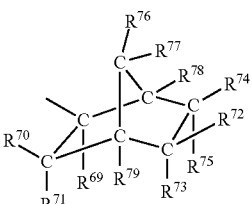

Herein $R^{69}$ is a straight, branched or cyclic $C_1$-$C_8$ alkyl group or optionally substituted $C_6$-$C_{20}$ aryl group. $R^{70}$ to $R^{75}$, $R^{78}$, and $R^{79}$ are each independently hydrogen or a monovalent $C_1$-$C_{15}$ hydrocarbon group, typically alkyl, which may contain a heteroatom, $R^{76}$ and $R^{77}$ are hydrogen; or a pair of $R^{70}$ and $R^{71}$, $R^{72}$ and $R^{74}$, $R^{72}$ and $R^{75}$, $R^{73}$ and $R^{75}$, $R^{73}$ and $R^{79}$, $R^{74}$ and $R^{78}$, $R^{76}$ and $R^{77}$, or $R^{77}$ and $R^{78}$ may bond together to form a ring, typically aliphatic ring, with the carbon atom to which they are attached, and in this case, the ring-forming participant is a divalent $C_1$-$C_{15}$ hydrocarbon group, typically alkylene, which may contain a heteroatom. Also, a pair of $R^{70}$ and $R^{79}$, $R^{76}$ and $R^{79}$, or $R^{72}$ and $R^{74}$ which are attached to vicinal carbon atoms may bond together directly to form a double bond. The formula also represents an enantiomer.

The ester form monomers from which recurring units having an exo-form structure represented by the formula (AL-12)-19 shown below are derived are described in U.S. Pat. No. 6,448,420 (JP-A 2000-327633).

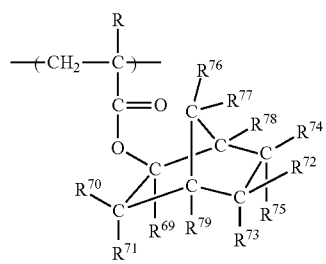
R is hydrogen or methyl. Illustrative non-limiting examples of suitable monomers are given below.
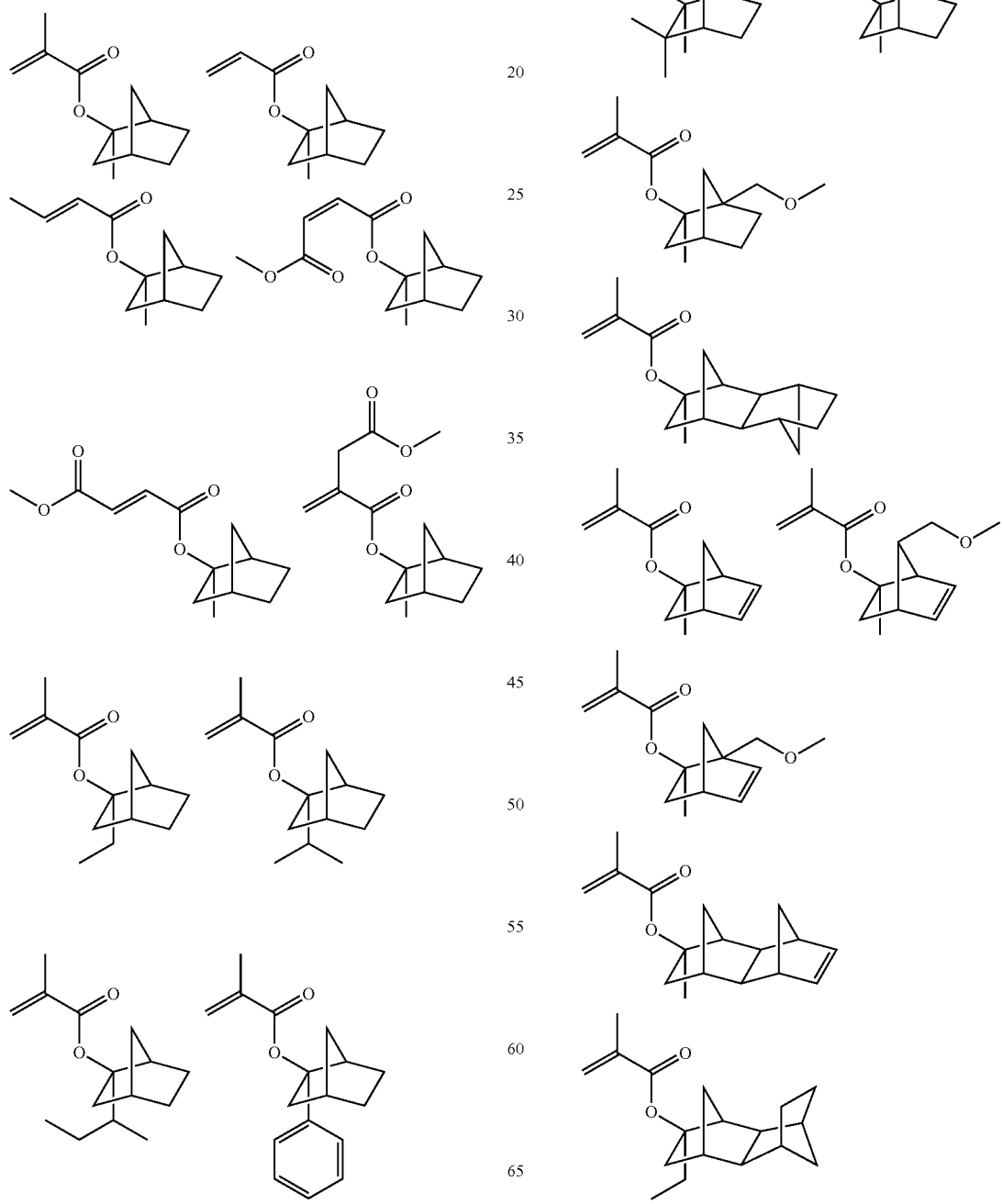

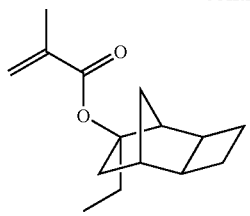

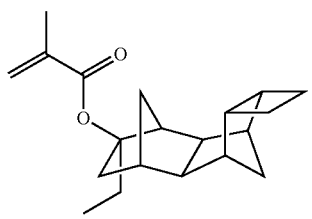

Also included in the acid labile groups of formula (AL-12) are acid labile groups having furandiyl, tetrahydrofurandiyl or oxanorbornanediyl as represented by the following formula (AL-12)-20.

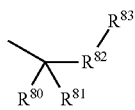 (AL-12)-20

Herein, $R^{80}$ and $R^{81}$ are each independently a monovalent hydrocarbon group, typically a straight, branched or cyclic $C_1$-$C_{10}$ alkyl group. $R^{80}$ and $R^{81}$, taken together, may form an aliphatic hydrocarbon ring of 3 to 20 carbon atoms with the carbon atom to which they are attached. $R^{82}$ is a divalent group selected from furandiyl, tetrahydrofurandiyl and oxanorbornanediyl. $R^{83}$ is hydrogen or a monovalent hydrocarbon group, typically a straight, branched or cyclic $C_1$-$C_{10}$ alkyl group, which may contain a heteroatom.

Recurring units substituted with an acid labile group having furandiyl, tetrahydrofurandiyl or oxanorbornanediyl as represented by the formula:

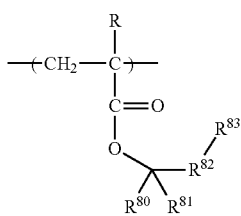

(wherein R, $R^{80}$ to $R^{83}$ are as defined above) are derived from monomers, examples of which are shown below. Note that Me is methyl and Ac is acetyl.

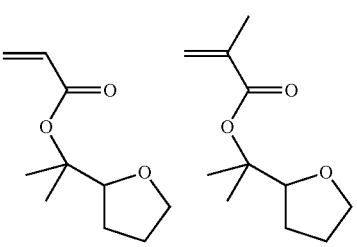

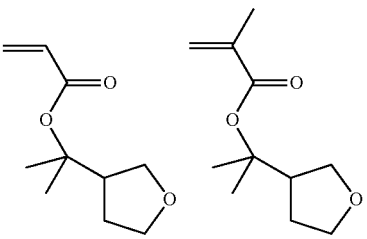

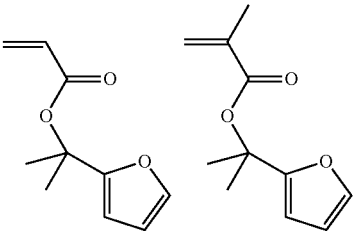

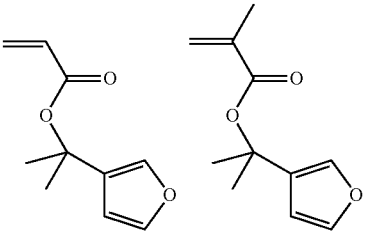

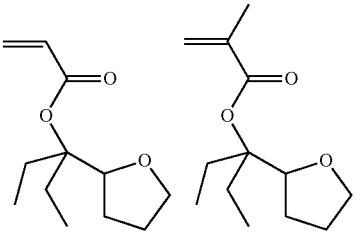

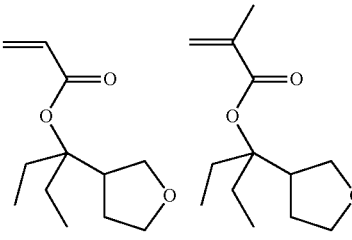

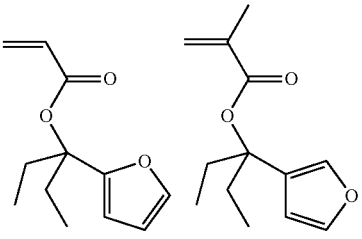

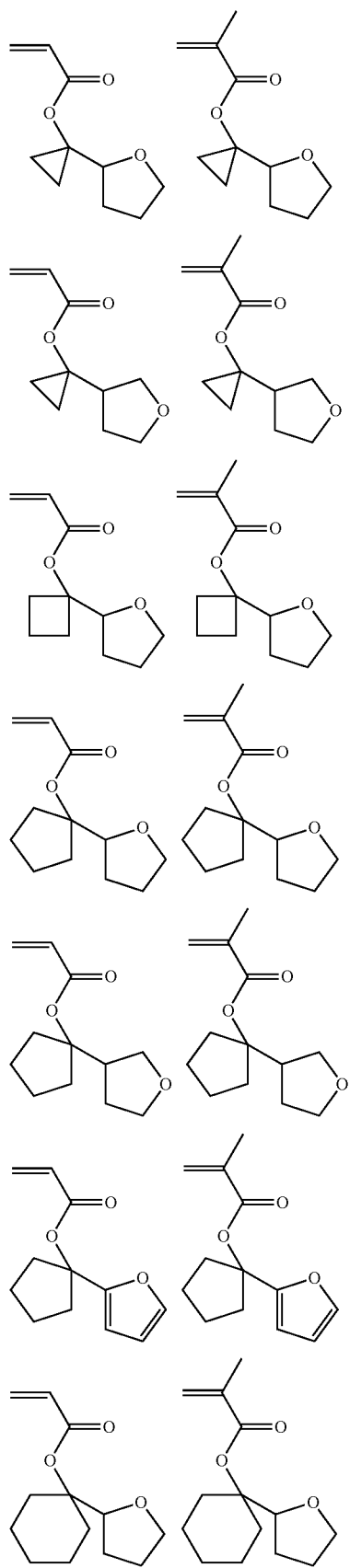
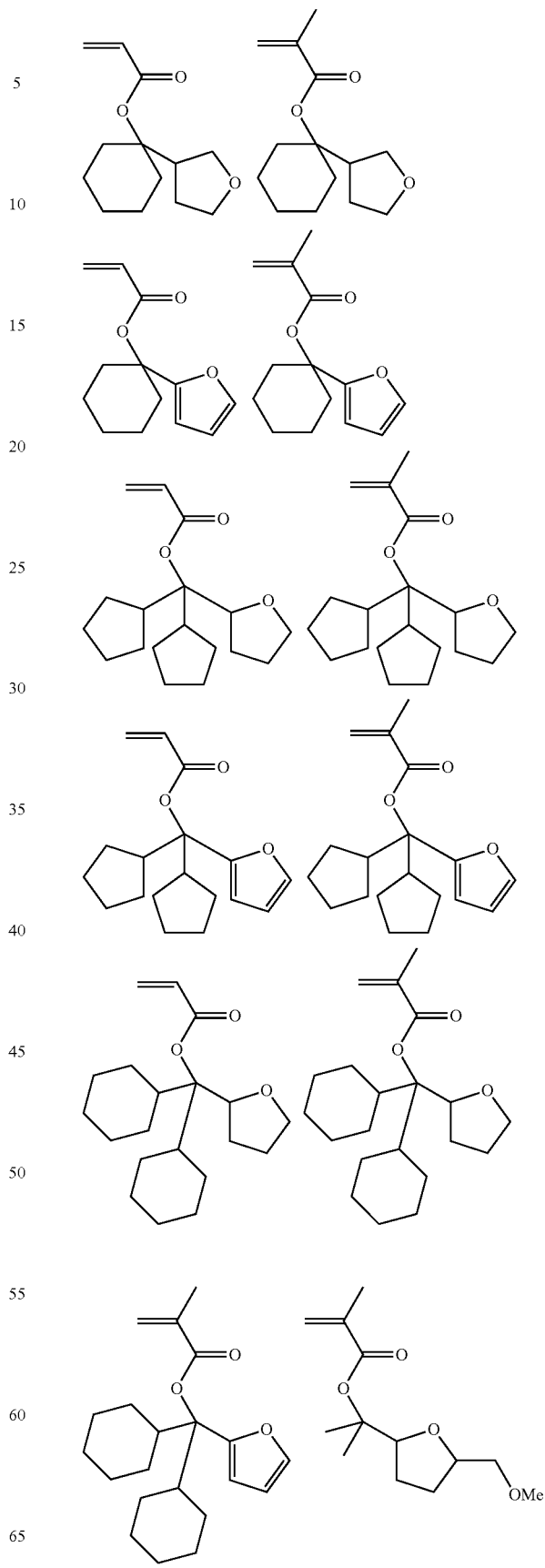

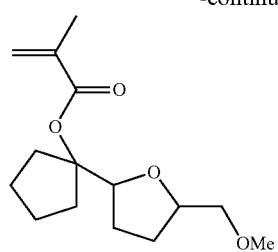
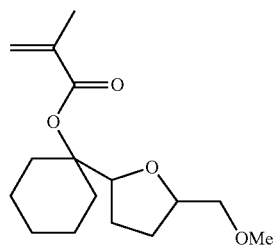
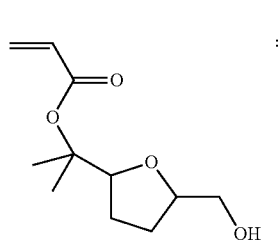
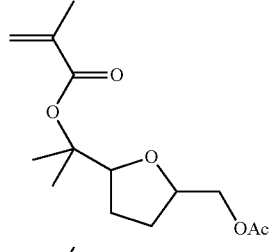
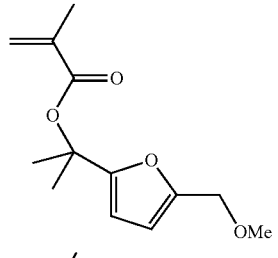
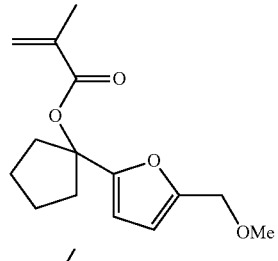
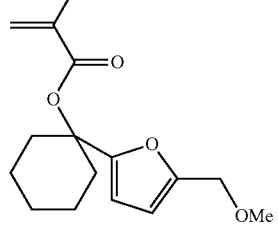
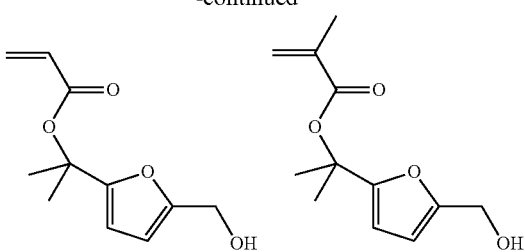
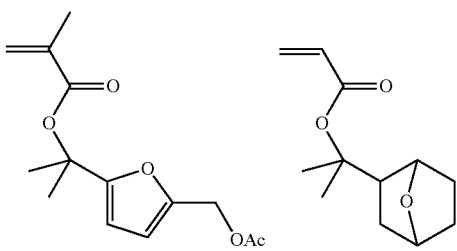
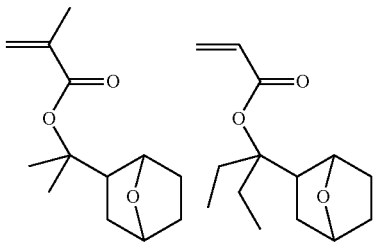
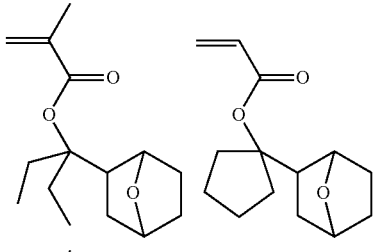
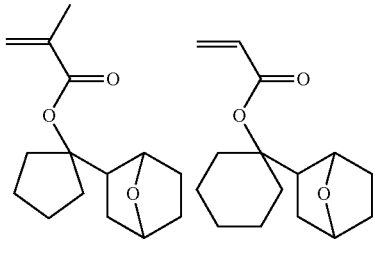
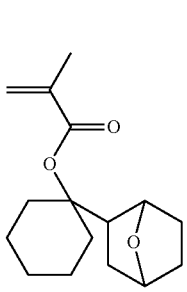
Of the acid labile groups of tertiary alkyl form having formula (AL-12), those acid labile groups having a branched alkyl directly attached to the ring offer high solubility in organic solvents. Such acid labile groups are exemplified below. In the following formula, the line segment protruding out of the bracket denotes a valence bond.

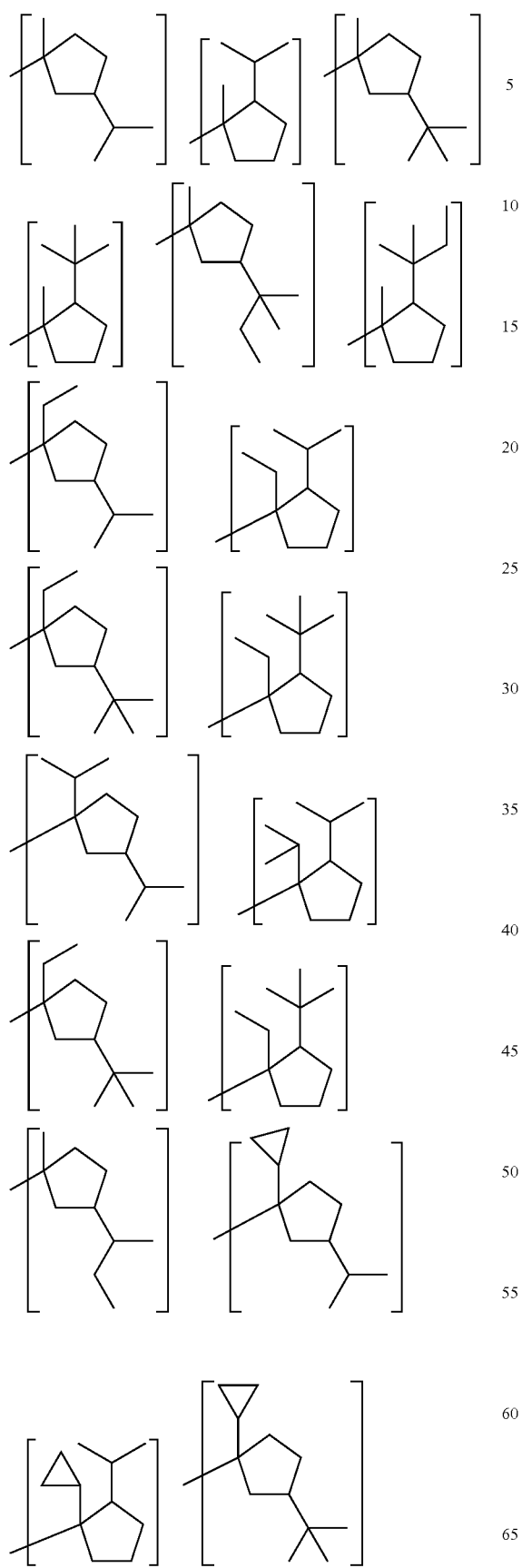
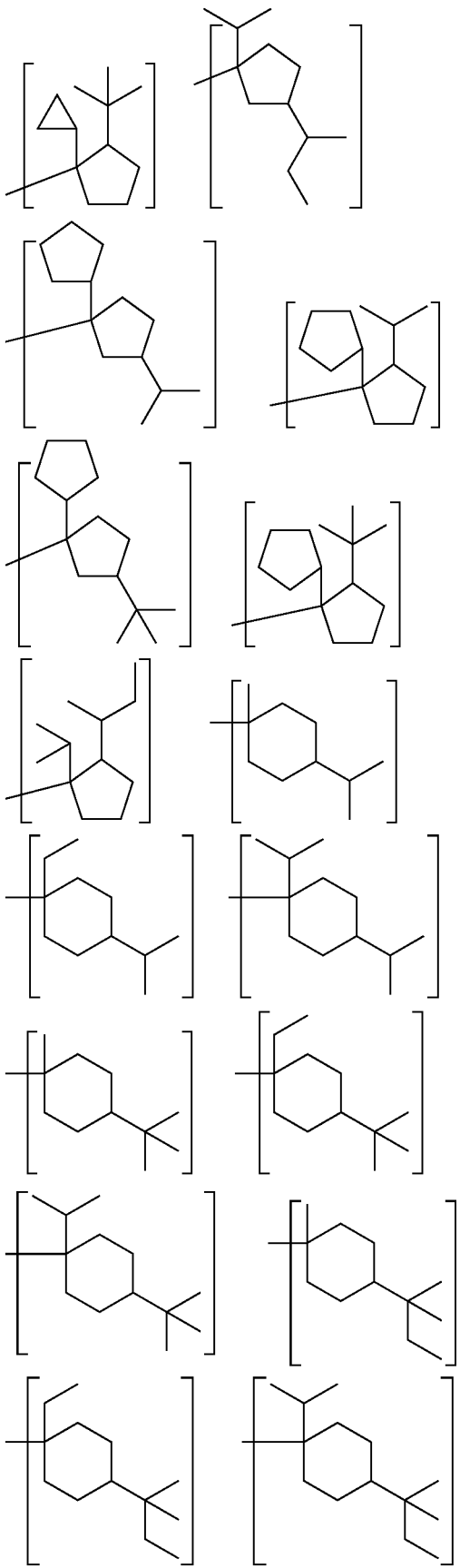
-continued

-continued

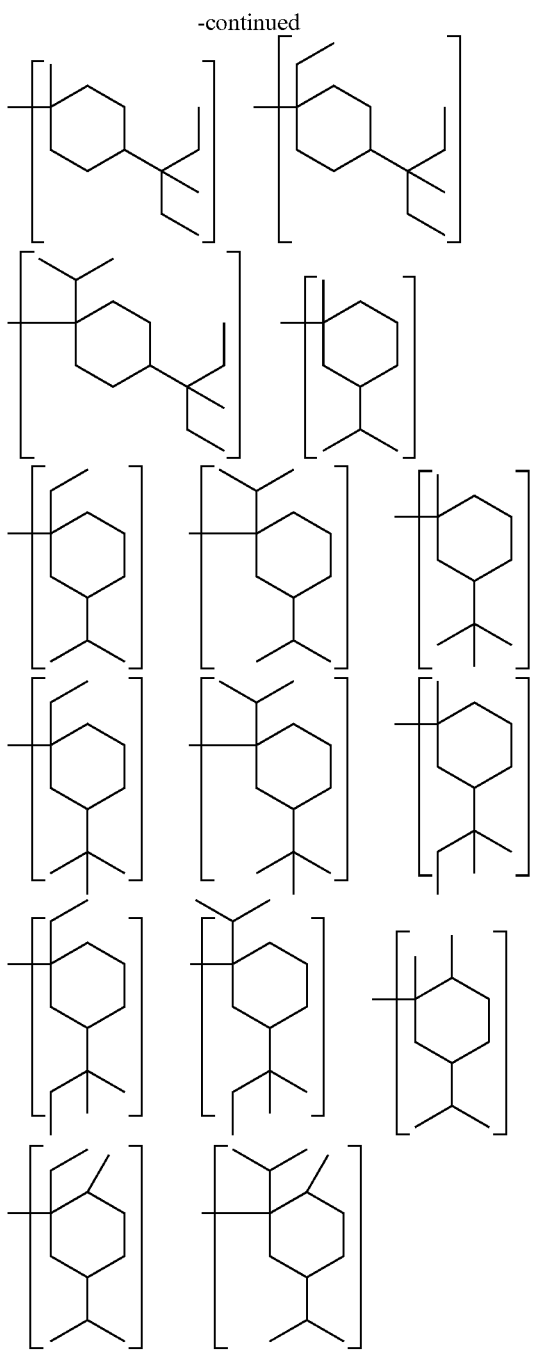

In the polymer for the shrink agent, the recurring units (a1), (a2), (a4), (a5), (b), (c), (d) and (e) are present in proportions a1, a2, a4, a5, b, c, d, and e, respectively, which satisfy the range: $0≤a1≤1.0$, $0≤a2≤1.0$, $0<a1+a2≤1.0$, $0≤a4≤0.8$, $0≤a5≤0.8$, $0≤b≤0.9$, $0≤c≤0.8$, $0≤d≤0.8$, and $0≤e≤0.8$;

preferably $0≤a1≤0.9$, $0≤a2≤0.9$, $0.1≤a1+a2≤0.9$, $0≤a4≤0.7$, $0≤a5≤0.7$, $0.1≤b≤0.9$, $0≤c≤0.7$, $0≤d≤0.7$, and $0≤e≤0.7$; and more preferably $0≤a1≤0.85$, $0≤a2≤0.85$, $0.2≤a1+a2≤0.85$, $0≤a4≤0.7$, $0≤a5≤0.7$, $0.15≤b≤0.8$, $0≤c≤0.6$, $0≤d≤0.6$, and $0≤e≤0.6$; provided that a1+a2+a4+a5+b+c+d+e=1.

On the other hand, the base resin in the resist composition used to form a resist pattern is a polymer comprising recurring units (a3) having an acid labile group-substituted carboxyl group, preferably represented by the general formula (2).

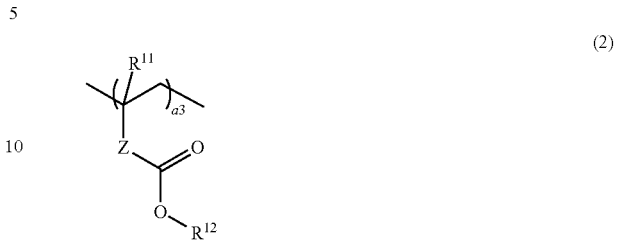

Herein $R^{11}$ is hydrogen or methyl. $R^{12}$ is an acid labile group. Z is a single bond or —C(=O)—O—$R^{13}$— wherein $R^{13}$ is a straight, branched or cyclic $C_1$-$C_{10}$ alkylene group which may contain an ether or ester moiety, or naphthylene group, and a3 is a number in the range: $0<a3<1.0$.

In the polymer comprising recurring units (a3) for use in the resist composition, recurring units (b) as described above may be copolymerized for improving the insolubility of the exposed region in organic solvent developer, improving adhesion to the substrate, and preventing pattern collapse. Further, there may be copolymerized recurring units having an adhesive group selected from among hydroxyl, lactone ring, ether, ester, carbonyl and cyano groups as described in JP-A 2012-37867, paragraphs [0076]-[0084], an indene, acenaphthylene, chromone, coumarin, and norbornadiene as described in paragraph [0085], a styrene, vinylnaphthalene, vinylanthracene, vinylpyrene, and methyleneindane as described in paragraph [0088], and an acid generator in the form of an onium salt having polymerizable olefin as described in paragraphs [0089]-[0091].

The following discussion applies to both the polymer serving as the shrink agent and the polymer serving as the base resin in the resist composition, both used in the patterning process. The polymer should preferably have a weight average molecular weight (Mw) in the range of 1,000 to 500,000, and more preferably 2,000 to 100,000, as measured by GPC versus polystyrene standards. If Mw is too low, in the case of shrink agent, the amount of shrinkage may become excessive or even uncontrollable due to an extended acid diffusion distance, and in the case of resist composition, the diffusion distance of acid generated by PAG may be extended to invite a drop of resolution. If Mw is too high, in the case of shrink agent, the solubility of the polymer in stripper solvent may be reduced, leaving scum in spaces at the end of removal step, and in the case of resist composition, a footing phenomenon is likely to occur after pattern formation.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the multi-component copolymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, molecular weight or dispersity is acceptable.

The polymers used herein may be synthesized by any desired method, for example, by dissolving one or more monomers in an organic solvent, adding a radical initiator thereto, and effecting heat polymerization. The monomers used herein include monomers corresponding to recurring units (a1), (a2), (a4), (a5), (b), (c), (d) and (e) in the case of shrink agent polymer, and monomers corresponding to acid labile group-bearing recurring units (a3), adhesive group-bearing recurring units (b) and the like in the case of resist polymer, and other unsaturated bond-bearing monomers. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours. The acid labile group that has been incorporated in the monomer may be kept as such, or the acid labile group may be once removed with an acid catalyst and the resulting polymer be protected or partially protected. In the polymer serving as the shrink agent, recurring units (a1), (a2), (a4), (a5), and (b) may be arranged randomly or blockwise.

The shrink agent used in the pattern forming process further contains an organic solvent and optionally a salt, basic compound and surfactant.

It is essential that the organic solvent do not dissolve the resist film after development. The organic solvent is selected from ester solvents of 7 to 16 carbon atoms and ketone solvents of 8 to 16 carbon atoms. Suitable ester solvents include amyl acetate, isoamyl acetate, 2-methylbutyl acetate, hexyl acetate, 2-ethylhexyl acetate, cyclohexyl acetate, methylcyclohexyl acetate, hexyl formate, ethyl valerate, propyl valerate, isopropyl valerate, butyl valerate, isobutyl valerate, tert-butyl valerate, amyl valerate, isoamyl valerate, ethyl isovalerate, propyl isovalerate, isopropyl isovalerate, butyl isovalerate, isobutyl isovalerate, tert-butyl isovalerate, isoamyl isovalerate, ethyl 2-methylvalerate, butyl 2-methylvalerate, ethyl pivalate, propyl pivalate, isopropyl pivalate, butyl pivalate, tert-butyl pivalate, ethyl pentenoate, propyl pentenoate, isopropyl pentenoate, butyl pentenoate, tert-butyl pentenoate, propyl crotonate, isopropyl crotonate, butyl crotonate, tert-butyl crotonate, butyl propionate, isobutyl propionate, tert-butyl propionate, benzyl propionate, ethyl hexanoate, allyl hexanoate, propyl butyrate, butyl butyrate, isobutyl butyrate, 3-methylbutyl butyrate, tert-butyl butyrate, ethyl 2-methylbutyrate, isopropyl 2-methylbutyrate, methyl benzoate, ethyl benzoate, propyl benzoate, butyl benzoate, phenyl acetate, benzyl acetate, methyl phenylacetate, benzyl formate, phenylethyl formate, methyl 3-phenylpropionate, ethyl phenylacetate, and 2-phenylethyl acetate. Suitable ketone solvents include 2-octanone, 3-octanone, 4-octanone, 2-nonanone, 3-nonanone, 4-nonanone, 5-nonanone, ethylcyclohexanone, ethylacetophenone, ethyl n-butyl ketone, di-n-butyl ketone, and diisobutyl ketone. These solvents may be used alone or in admixture of two or more.

For the purpose of preventing intermixing of the shrink agent and the resist pattern, any of $C_3$-$C_{10}$ alcohol, $C_8$-$C_{12}$ ether, $C_6$-$C_{12}$ alkane, alkene, alkyne and aromatic solvents may be blended with the above solvent. Specifically, suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-amyl ether, and di-n-hexyl ether. Suitable aromatic solvents include toluene, xylene, ethylbenzene, isopropylbenzene, tert-butylbenzene, mesitylene, and anisole. The solvents may be used alone or in admixture.

In the shrink agent solution, the solvent is preferably used in an amount of 100 to 100,000 parts, more preferably 200 to 50,000 parts by weight per 100 parts by weight of the polymer.

To the shrink agent, a salt and basic compound may be added if desired. The salt that can be added is typically selected from sulfonium salts and iodonium salts which are typically added to resist compositions, and ammonium salts. The basic compound that can be added may be selected from those basic compounds which are typically added to resist compositions, for example, primary, secondary and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, and imide derivatives. The addition of the salt or basic compound is effective for suppressing excessive diffusion of acid from within the resist film and for controlling the amount of shrinkage. The surfactant that can be added may be selected from those surfactants which are typically added to resist compositions.

As the salt, a salt compound having the general formula (3)-1 or (3)-2 is preferred.

$$R^{14}-CO_2^- M^+ \quad (3)\text{-}1$$

$$R^{14}-SO_3^- M^+ \quad (3)\text{-}2$$

Herein R" is a straight, branched or cyclic $C_1$-$C_{20}$ alkyl group, $C_2$-$C_{20}$ alkenyl group or $C_6$-$C_{20}$ aryl group which may contain fluorine, ether moiety, ester moiety, lactone ring, lactam ring, carbonyl moiety or hydroxyl moiety, and M is sulfonium, iodonium or ammonium.

Examples of the anion: $R^{14}-CO_2^-$ are shown below.

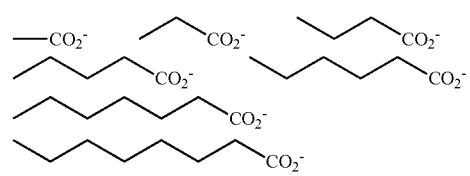

-continued
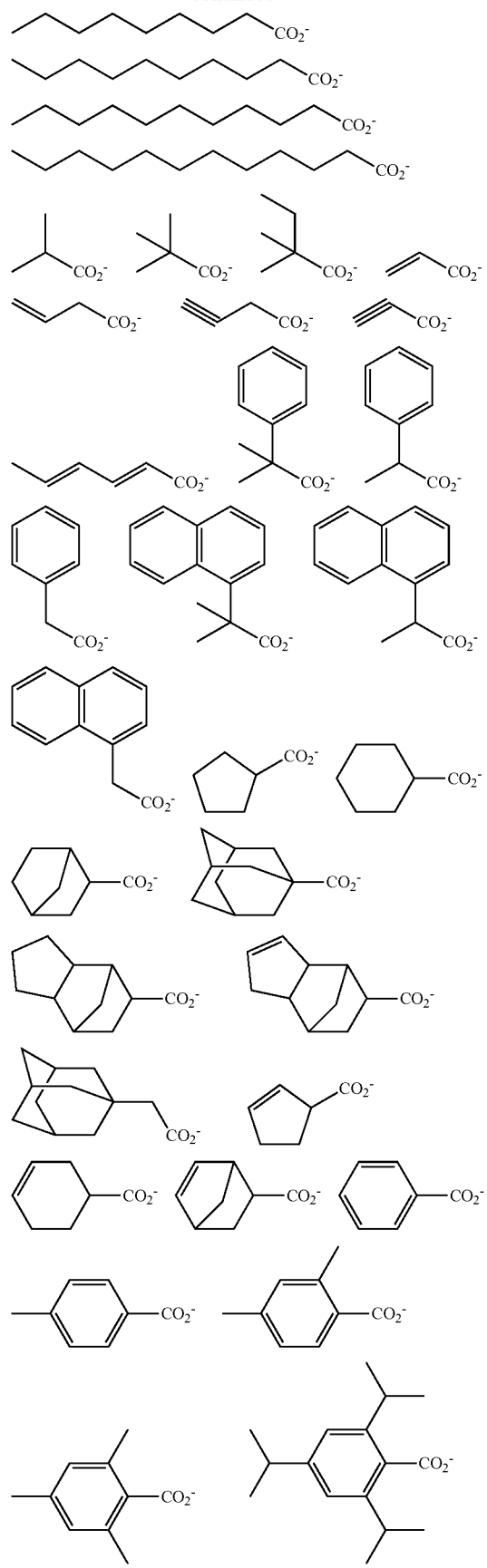
-continued
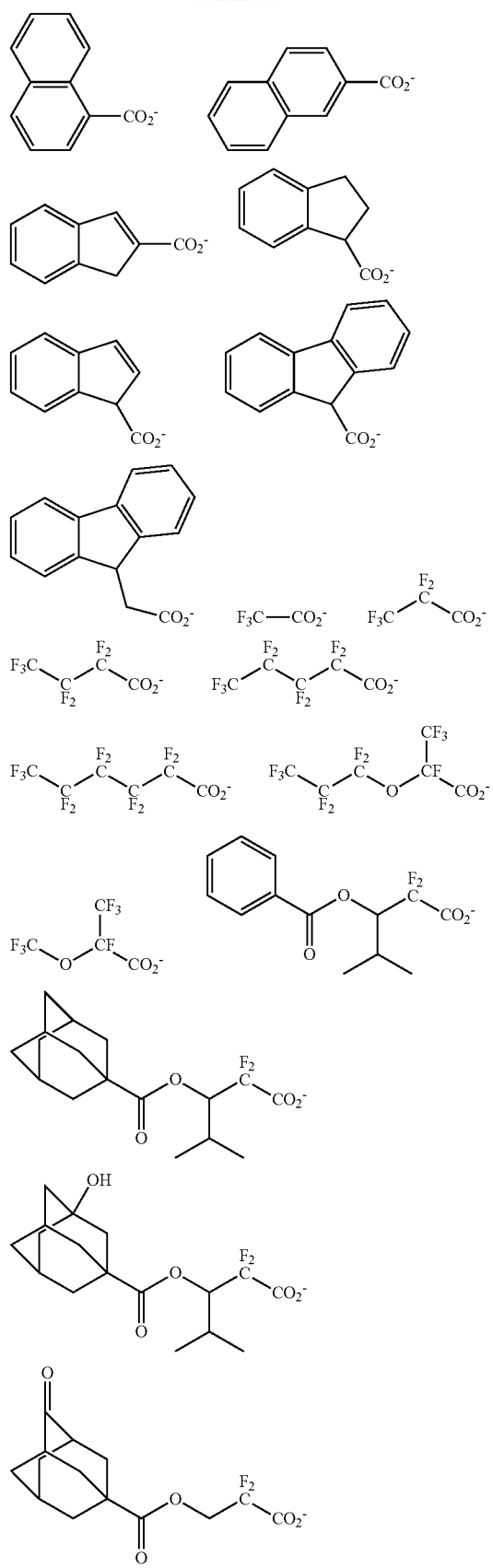

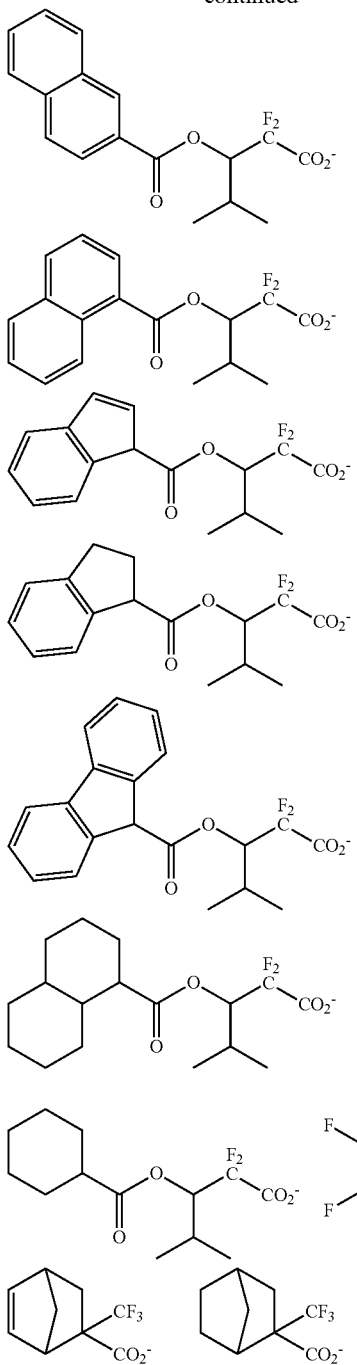

Examples of the anion: $R^{14}-SO_3^-$ are shown below.

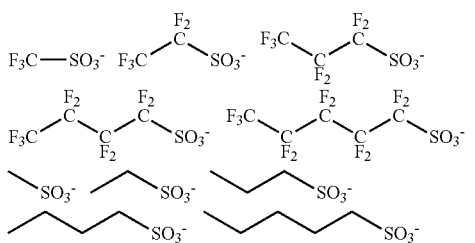

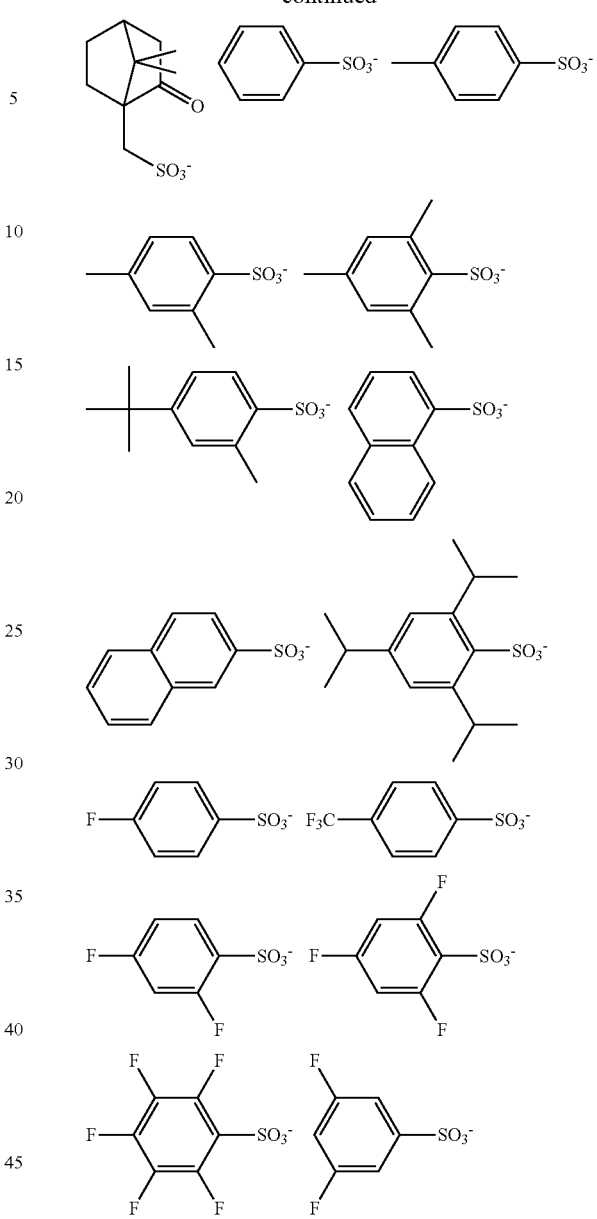

Of the salt compounds of formula (3)-1, sulfonium, iodonium and ammonium salts of carboxylic acid represented by formulae (P1a-1) to (P1a-3) are preferred. Of the salt compounds of formula (3)-2, sulfonium, iodonium and ammonium salts of sulfonic acid represented by formulae (P1b-1) to (P1b-3) are preferred. Acid diffusion may be effectively controlled by adding these salts.

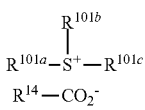 (P1a-1)

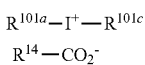 (P1a-2)

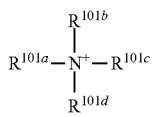 (Pla-3)

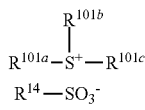 (Plb-1)

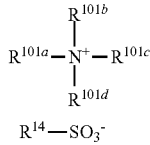 (Plb-3)

Herein $R^{101a}$, $R^{101b}$, $R^{101c}$ and $R^{101d}$ are each independently a straight, branched or cyclic $C_1$-$C_{12}$ alkyl, alkenyl, oxoalkyl or oxoalkenyl, $C_6$-$C_{20}$ aryl, or $C_7$-$C_{12}$ aralkyl or aryloxoalkyl group, in which some or all hydrogen atoms may be replaced by alkoxy or other groups, $R^{101b}$ and $R^{101c}$ may bond together to form a ring which may contain an ether, ester, sultone or amino moiety, each of $R^{101b}$ and $R^{101c}$ is $C_1$-$C_{10}$ alkylene or arylene when they form a ring. $R^{14}$ is as defined above.

In the shrink agent, preferably the salt is used in an amount of 0 to 50 parts by weight, the basic compound is used in an amount of 0 to 30 parts by weight, and the surfactant is used in an amount of 0 to 10 parts, more preferably 0 to 5 parts by weight, all per 100 parts by weight of the polymer. When added, each additive is preferably used in an amount of at least 0.1 part by weight.

The resist composition comprises the polymer as base resin, an organic solvent, and an acid generator (i.e., compound capable of generating an acid in response to high-energy radiation), and optionally, a dissolution regulator, basic compound, surfactant, acetylene alcohol, and other components.

Specifically, the resist composition contains an acid generator such that it may function as a chemically amplified resist composition. The acid generator is typically a compound capable of generating an acid in response to actinic light or radiation, known as photoacid generator (PAG). An appropriate amount of the PAG used is 0.5 to 30 parts, more preferably 1 to 20 parts by weight per 100 parts by weight of the base resin. The PAG is any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. The acid generators may be used alone or in admixture of two or more. Exemplary of the acid generated by PAG are sulfonic acids, imidic acids and methide acids. Of these, sulfonic acids which are fluorinated at α-position are most commonly used. Where the acid labile group is an acetal group susceptible to deprotection, fluorination at α-position is not always necessary. Where the base polymer has recurring units of acid generator copolymerized therein, the acid generator need not be separately added.

Examples of the organic solvent used herein are described in JP-A 2008-111103, paragraphs [0144] to [0145] (U.S. Pat. No. 7,537,880). Specifically, exemplary solvents include ketones such as cyclohexanone and methyl-2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal.

Exemplary basic compounds include primary, secondary and tertiary amine compounds, specifically amine compounds having a hydroxyl, ether, ester, lactone, cyano or sulfonate group, as described in JP-A 2008-111103, paragraphs [0146] to [0164], and compounds having a carbamate group, as described in JP 3790649. Also, onium salts such as sulfonium salts, iodonium salts and ammonium salts of sulfonic acids which are not fluorinated at α-position as described in US 2008153030 (JP-A 2008-158339) and similar onium salts of carboxylic acid as described in JP 3991462 and JP 426803 may be used as the quencher. They may also be added to the shrink agent.

Where the acid labile group is an acetal group which is very sensitive to acid, the acid for eliminating the protective group need not necessarily be a sulfonic acid which is fluorinated at α-position, imidic acid or methide acid. Even with a sulfonic acid which is not fluorinated at α-position, deprotection reaction may take place in some cases. Since an onium salt of sulfonic acid cannot be used as the quencher in this event, an onium salt of imidic acid is preferably used alone.

Exemplary surfactants are described in JP-A 2008-111103, paragraphs [0165]-[0166]. Exemplary dissolution regulators are described in JP-A 2008-122932 (US 2008090172), paragraphs [0155]-[0178], and exemplary acetylene alcohols in paragraphs [0179]-[0182].

Also a polymeric additive may be added for improving the water repellency on surface of a resist film as spin coated. This additive may be used in the topcoatless immersion lithography. These additives have a specific structure with a 1,1,1,3,3,3-hexafluoro-2-propanol residue and are described in JP-A 2007-297590 and JP-A 2008-111103. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB and avoiding any hole pattern opening failure after development. An appropriate amount of the water repellency improver is 0.1 to 20 parts, preferably 0.5 to 10 parts by weight per 100 parts by weight of the base resin.

Notably, an appropriate amount of the organic solvent is 100 to 10,000 parts, preferably 300 to 8,000 parts by weight, and an appropriate amount of the basic compound is 0.0001 to 30 parts, preferably 0.001 to 20 parts by weight, per 100 parts by weight of the base resin. The dissolution regulator, surfactant and acetylene alcohol may be used in any suitable amounts, depending on their purpose of addition.

Figure 2E:
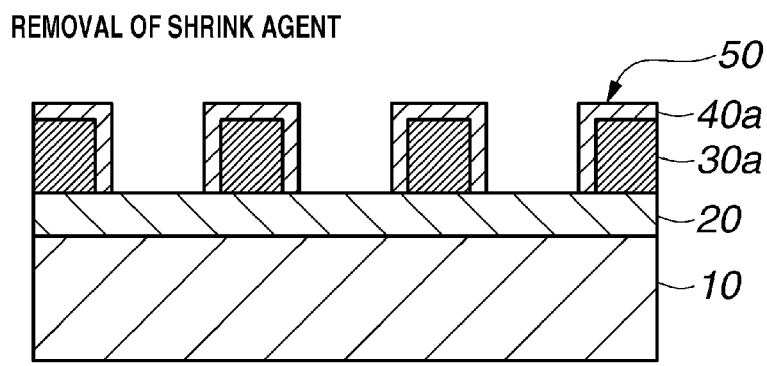
Figure 2F:
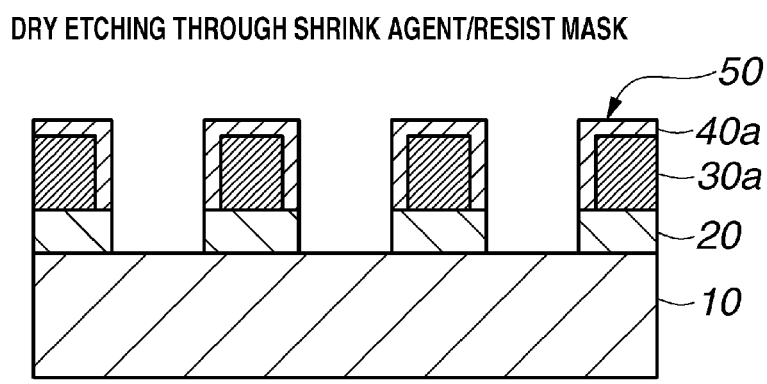

Referring to FIGS. 1 and 2, the pattern shrinking process of the invention is described. First, as shown in FIG. 1(A), a chemically amplified resist composition is applied onto a processable substrate 20 on a substrate 10 to form a photoresist film 30 thereon. If necessary, a hard mask layer (not shown) may intervene between the resist film 30 and the processable substrate 20. By standard techniques, the resist film 30 is subjected to exposure (FIG. 1(B)), PEB, and organic solvent development to form a negative resist pattern 30a (FIG. 1(C)). A shrink agent 40 is applied onto the negative resist pattern 30a to cover the pattern as shown in FIG. 2(D). The shrink agent coating is baked, during which the heat functions to evaporate off the solvent and to cause the acid to diffuse from the resist pattern 30 into the shrink agent coating 40. With the acid, the polymer in the shrink agent coating undergoes deprotection reaction. Thereafter, a solvent is applied to remove the excessive shrink agent 40, leaving a shrink agent film 40a over the resist pattern 30a. This means that the resist pattern 30a is thickened at 50, that is, the width of spaces in the resist pattern is shrunk as shown in FIG. 2(E). Using the shrunk pattern 50 as a mask, the processable substrate 20 is dry etched as shown in FIG. 2(F).

The substrate 10 used herein is generally a silicon substrate. The processable substrate (or target film) 20 used herein includes $SiO_2$, SiN, SiON, SiOC, p-Si, $\alpha$-Si, TiN, WSi, BPSG, SOG, Cr, CrO, CrON, MoSi, low dielectric film, and etch stopper film. The hard mask may be of $SiO_2$, SiN, SiON or p-Si. Sometimes, an undercoat in the form of carbon film or a silicon-containing intermediate film may be laid instead of the hard mask, and an organic antireflective coating may be interposed between the hard mask and the resist film.

While a resist film (30) of a chemically amplified resist composition is formed on a processable substrate (20) on a substrate (10) directly or via an intermediate intervening layer as mentioned above, the resist film preferably has a thickness of 10 to 1,000 nm and more preferably 20 to 500 nm. Prior to exposure, the resist film is heated or prebaked, preferably at a temperature of 50 to 180° C., especially 60 to 150° C. for a time of 10 to 300 seconds, especially 15 to 200 seconds.

Next the resist film is exposed. For the exposure, preference is given to high-energy radiation, which is typically i-line of wavelength 364 nm, KrF excimer laser of wavelength 248 nm, ArF excimer laser of wavelength 193 nm, EUV of wavelength 13.5 nm, or electron beam (EB). The exposure may be done either in a dry atmosphere such as air or nitrogen stream or by immersion lithography in water. The ArF immersion lithography uses deionized water or liquids having a refractive index of at least 1 and highly transparent to the exposure wavelength such as alkanes as the immersion solvent. In the immersion lithography, the prebaked resist film is exposed to light through a projection lens, with pure water or another liquid introduced between the resist film and the projection lens. Since this allows lenses to be designed to a NA of 1.0 or higher, formation of finer feature size patterns is possible. The immersion lithography is important for the ArF lithography to survive to the 45-nm node. In the case of immersion lithography, deionized water rinsing (or post-soaking) may be carried out after exposure for removing water droplets left on the resist film, or a protective film may be applied onto the resist film after pre-baking for preventing any leach-out from the resist film and improving water slip on the film surface. The resist protective film used in the immersion lithography is preferably formed from a solution of a polymer having 1,1,1,3,3,3-hexafluoro-2-propanol residues which is insoluble in water, but soluble in an alkaline developer liquid, in a solvent selected from alcohols of 4 to 10 carbon atoms, ethers of 8 to 12 carbon atoms, and mixtures thereof. After formation of the photoresist film, deionized water rinsing (or post-soaking) may be carried out for extracting the acid generator and the like from the film surface or washing away particles, or after exposure, rinsing (or post-soaking) may be carried out for removing water droplets left on the resist film.

Exposure is preferably performed in an exposure dose of about 1 to 200 mJ/cm$^2$, more preferably about 10 to 100 mJ/cm$^2$. This is followed by baking (PEB) on a hot plate at 50 to 150° C. for 1 to 5 minutes, preferably at 60 to 120° C. for 1 to 3 minutes.

Thereafter the exposed resist film is developed with a developer consisting of an organic solvent for 0.1 to 3 minutes, preferably 0.5 to 2 minutes by any conventional techniques such as dip, puddle and spray techniques. In this way, a negative resist pattern is formed on the substrate. The organic solvent used as developer is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film may be rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-amyl ether, and di-n-hexyl ether. Suitable aromatic solvents include toluene, xylene, ethylbenzene, isopropylbenzene, t-butylbenzene, and mesitylene. The solvents may be used alone or in admixture. After the rinse liquid is applied, the substrate may be dried by spin drying and bake. However, rinsing is not essential. As long as the step of spin drying the substrate after the developer is applied thereto is included, the rinsing step may be omitted.

Following the development, the shrink agent of the invention is applied onto the resist pattern to form a shrink agent coating, preferably having a thickness of 1 to 100 nm, more preferably 1.5 to 50 nm. The shrink agent coating is baked at a temperature of 40 to 150° C. for 5 to 300 seconds. Bake functions to evaporate off the solvent, and acid diffusion from the resist film to the shrink agent and the finally-produced lactone ring would cause a polarity change, thereby rendering the shrink agent coating insoluble in the organic solvent developer.

Finally, the excessive shrink agent is removed, preferably using the organic solvent developer. This means that development of the resist film and removal of the shrink agent can be performed with an identical organic solvent. The nozzle needed is only one.

EXAMPLE

Examples of the invention are given below by way of illustration and not by way of limitation. The abbreviation "pbw" is parts by weight, and PGMEA is propylene glycol monomethyl ether acetate. For all polymers, Mw and Mn are determined by GPC versus polystyrene standards.

Synthesis Example

Polymers (for use in shrink agent and resist composition) were synthesized by combining suitable monomers in tetrahydrofuran solvent, effecting copolymerization reaction, crystallizing from methanol, repeatedly washing with hexane, isolation and drying. There were obtained random copolymers, designated Polymers 1 to 14, Comparative Polymers 1, 2, Resist Polymer 1, and Water-repellent Polymer 1. The polymers were analyzed for composition by $^1$H-NMR spectroscopy and for Mw and Mw/Mn by GPC. The polymers are identified below with their analytical data.

Polymer 1

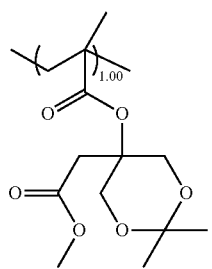

Mw = 9,100
Mw/Mn = 1.67

Polymer 1

Polymer 2

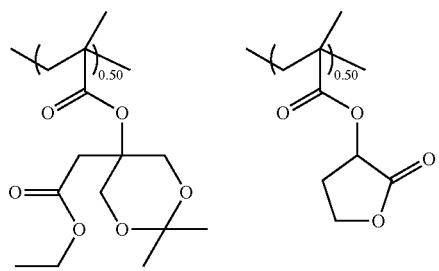

Mw = 9,100
Mw/Mn = 1.78

Polymer 2

-continued
Polymer 3
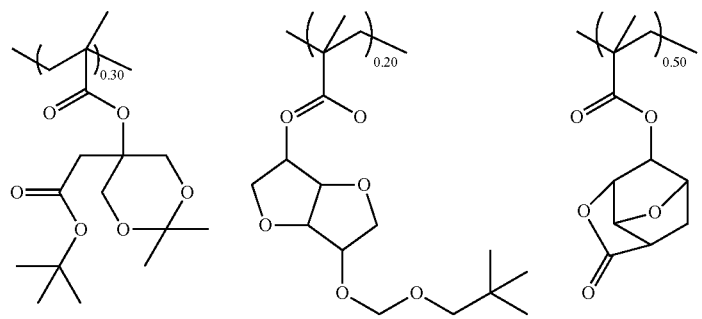
Mw = 7,100
Mw/Mn = 1.82
Polymer 4
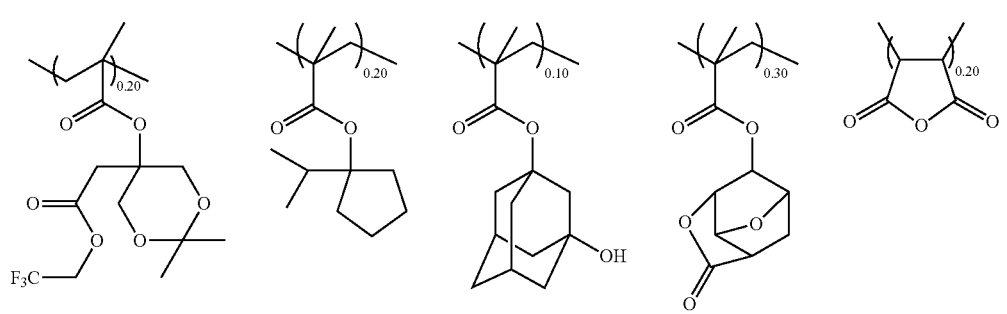
Mw = 7,200
Mw/Mn = 1.77
Polymer 5
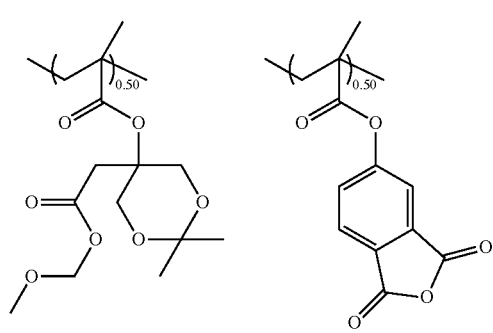
Mw = 9,700
Mw/Mn = 1.9

-continued
Polymer 6
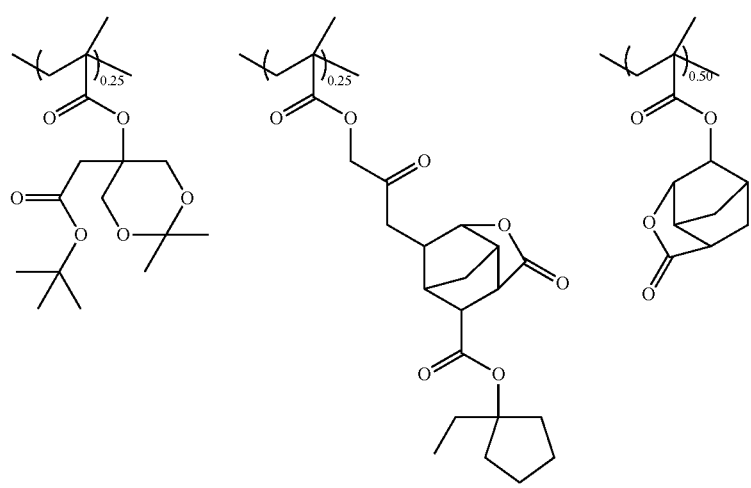
Mw = 7,700
Mw/Mn = 1.77
Polymer 7
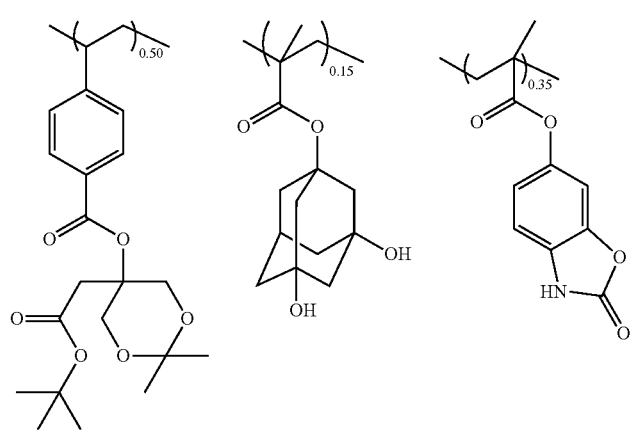
Mw = 10,500
Mw/Mn = 1.87
Polymer 8
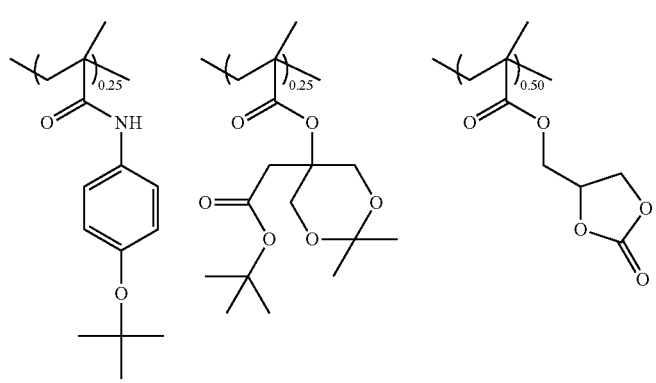
Mw = 12,100
Mw/Mn = 1.69

Polymer 9
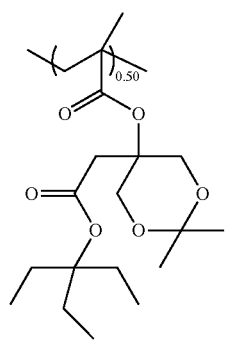 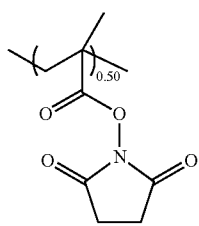
Mw = 13,100
Mw/Mn = 1.68
Polymer 10
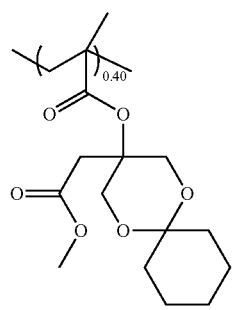 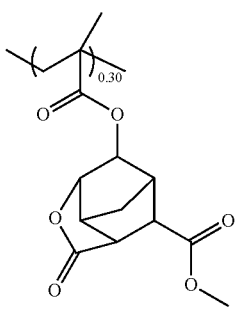 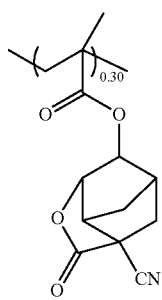
Mw = 8,200
Mw/Mn = 1.84
Polymer 11
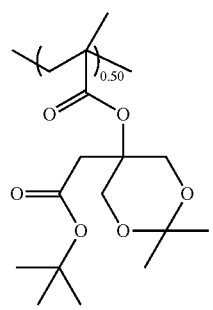 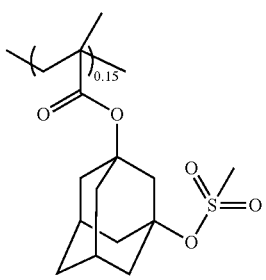 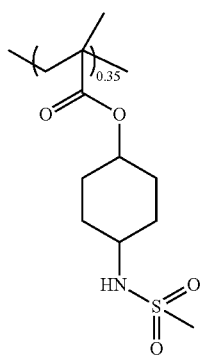
Mw = 8,300
Mw/Mn = 1.88

Polymer 12
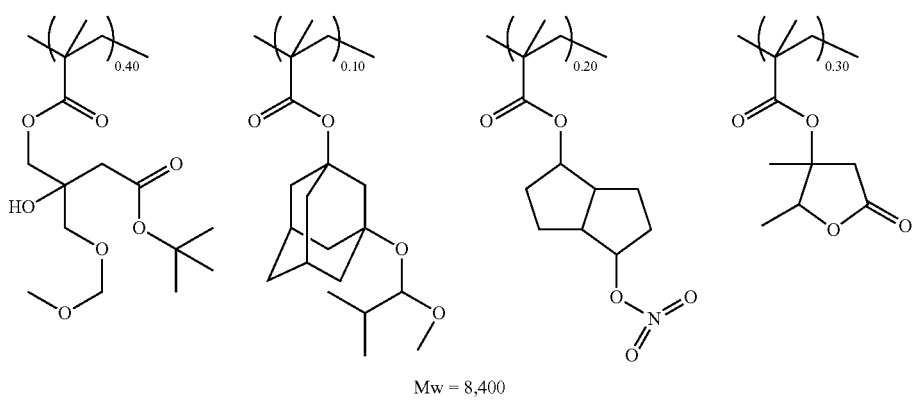
Mw = 8,400
Mw/Mn = 1.68
Polymer 13
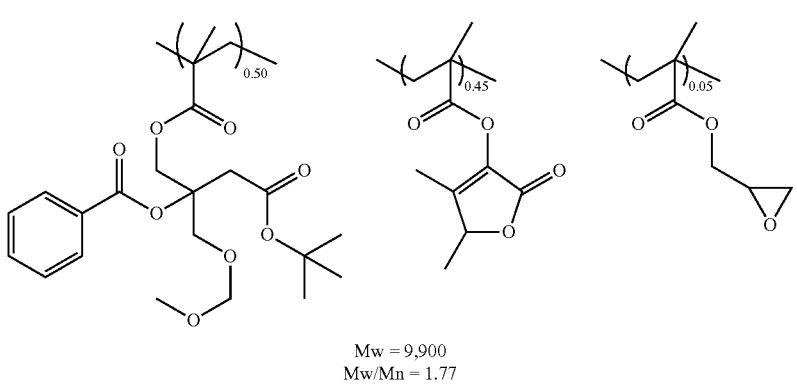
Mw = 9,900
Mw/Mn = 1.77
Polymer 14
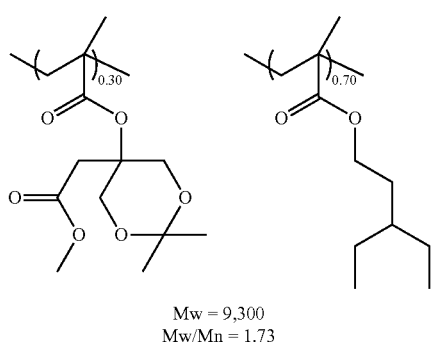
Mw = 9,300
Mw/Mn = 1.73
Comparative Polymer 1
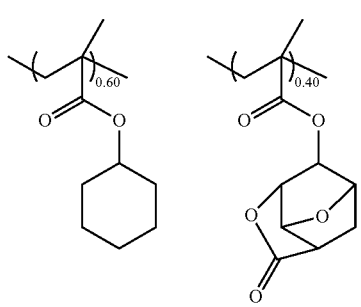
Mw = 8,700
Mw/Mn = 1.73

-continued
Comparative Polymer 2
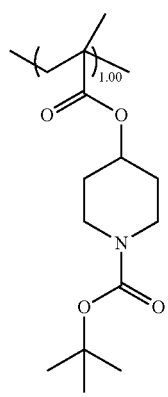
Resist Polymer 1
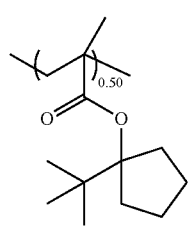 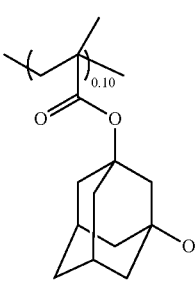 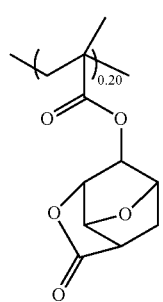 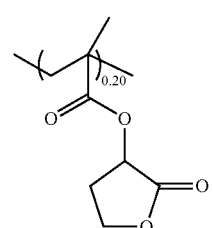
Mw = 7,500
Mw/Mn = 1.61
Water-repellent Polymer 1
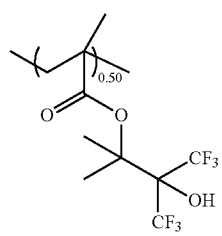 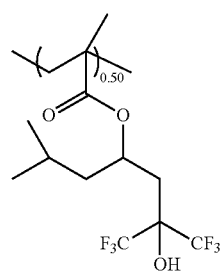
Mw = 7,800
Mw/Mn = 1.55

Examples 1 to 36 and Comparative Examples 1 to 4

A shrink agent solution was prepared by mixing the polymer synthesized above (Polymers 1 to 14 or Comparative Polymers 1, 2), additive (e.g., sulfonium salt), and solvent in accordance with the formulation of Tables 1 and 2, and filtering through a Teflon® filter having a pore size of 0.2 μm. Components shown in Tables 1 and 2 are identified below.

Acid generator: PAG1 of the following structural formula

PAG 1

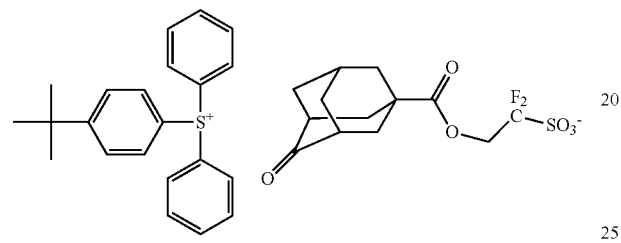

Sulfonium salts 1 to 12, Iodonium salt 1, Ammonium salts 1, 2 and Amine quenchers 1, 2 of the following structural formulae Sulfonium salt 1

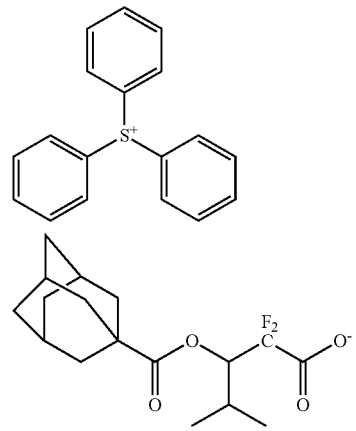

Sulfonium salt 2

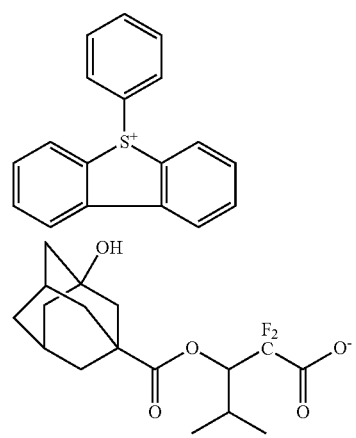

Sulfonium salt 3

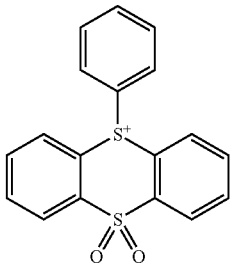

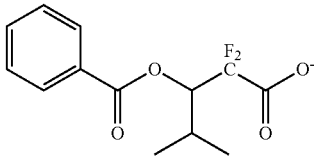

Sulfonium salt 4

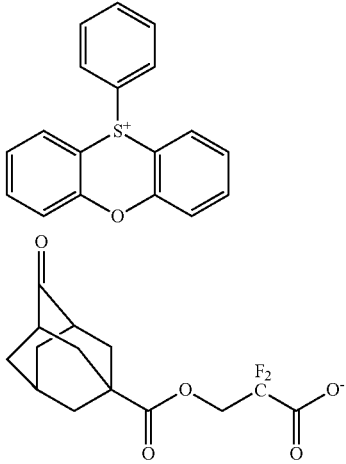

Sulfonium salt 5

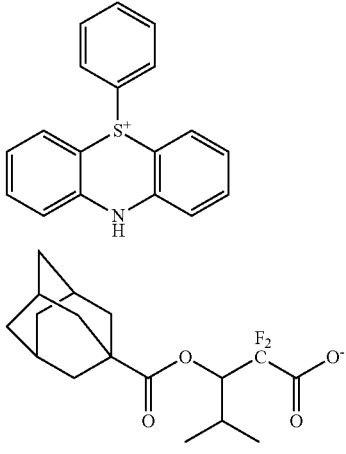

Sulfonium salt 6

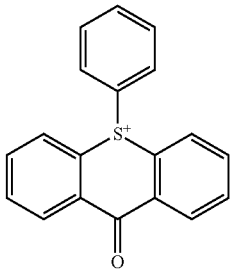

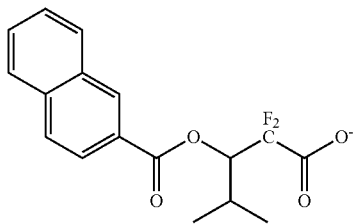
Sulfonium salt 7
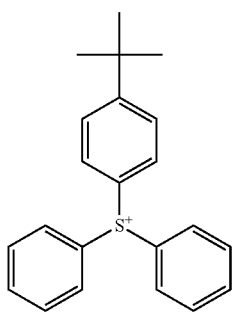 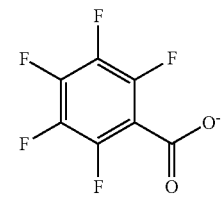
Sulfonium salt 8
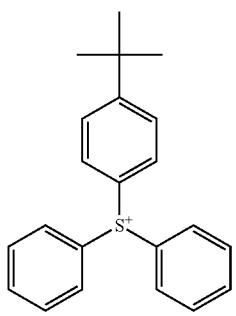 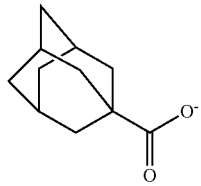
Sulfonium salt 9
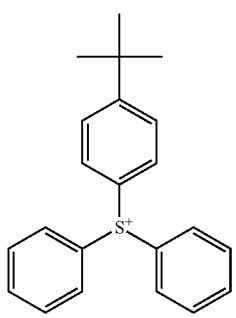 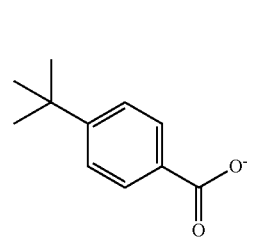
Sulfonium salt 10
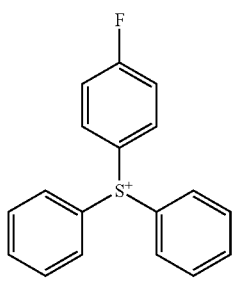 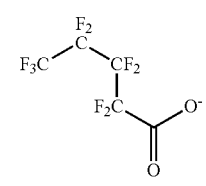
Sulfonium salt 11
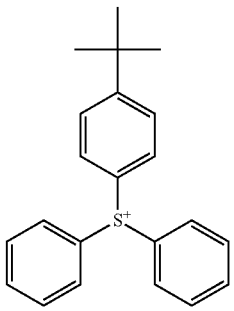 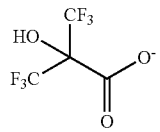
Sulfonium salt 12
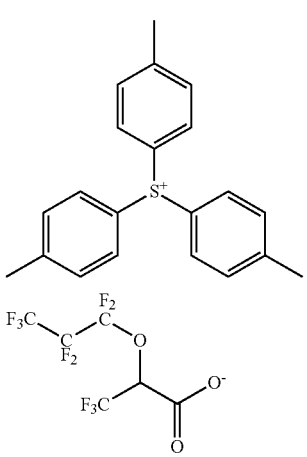
Iodonium salt 1
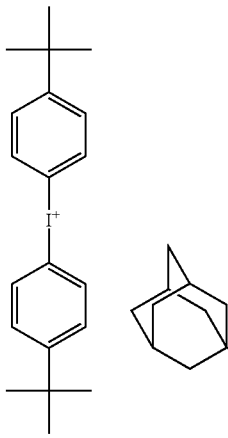
Ammonium salt 1
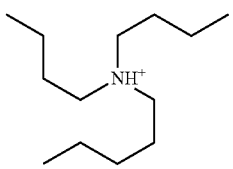 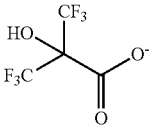
Ammonium salt 2
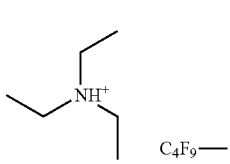
C$_4$F$_9$—SO$_3^-$

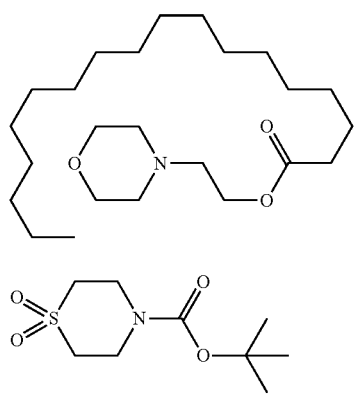

Amine quencher 1

Amine quencher 2

TABLE 1

| Shrink agent | Polymer (pbw) | Additive (pbw) | Organic solvent (pbw) |
|---|---|---|---|
| Shrink agent 1 | Polymer 1 (100) | — | isoamyl acetate (6,000) |
| Shrink agent 2 | Polymer 2 (100) | Sulfonium salt 1 (2.0) | isoamyl acetate (6,000) |
| Shrink agent 3 | Polymer 3 (100) | Sulfonium salt 1 (2.0) | isoamyl acetate (6,000) |
| Shrink agent 4 | Polymer 4 (100) | Sulfonium salt 1 (2.0) | isoamyl acetate (6,000) |
| Shrink agent 5 | Polymer 5 (100) | Sulfonium salt 1 (2.0) | isoamyl acetate (6,000) |
| Shrink agent 6 | Polymer 6 (100) | Sulfonium salt 1 (2.0) | isoamyl acetate (6,000) |
| Shrink agent 7 | Polymer 7 (100) | Sulfonium salt 1 (2.0) | isoamyl acetate (6,000) |
| Shrink agent 8 | Polymer 8 (100) | Sulfonium salt 1 (2.0) | isoamyl acetate (6,000) |
| Shrink agent 9 | Polymer 9 (100) | Sulfonium salt 1 (2.0) | isoamyl acetate (6,000) |
| Shrink agent 10 | Polymer 10 (100) | Sulfonium salt 1 (2.0) | isoamyl acetate (6,000) |
| Shrink agent 11 | Polymer 11 (100) | Sulfonium salt 1 (2.0) | isoamyl acetate (6,000) |
| Shrink agent 12 | Polymer 12 (100) | Sulfonium salt 1 (2.0) | isoamyl acetate (6,000) |
| Shrink agent 13 | Polymer 13 (100) | Sulfonium salt 1 (2.0) | isoamyl acetate (6,000) |
| Shrink agent 14 | Polymer 2 (100) | Sulfonium salt 2 (2.0) | isoamyl acetate (6,000) |
| Shrink agent 15 | Polymer 2 (100) | Sulfonium salt 3 (2.0) | isoamyl acetate (6,000) |
| Shrink agent 16 | Polymer 2 (100) | Sulfonium salt 4 (2.0) | isoamyl acetate (6,000) |
| Shrink agent 17 | Polymer 2 (100) | Sulfonium salt 5 (2.0) | isoamyl acetate (6,000) |
| Shrink agent 18 | Polymer 2 (100) | Sulfonium salt 6 (2.0) | isoamyl acetate (6,000) |
| Shrink agent 19 | Polymer 2 (100) | Sulfonium salt 7 (2.0) | isoamyl acetate (6,000) |
| Shrink agent 20 | Polymer 2 (100) | Sulfonium salt 8 (2.0) | isoamyl acetate (6,000) |
| Shrink agent 21 | Polymer 2 (100) | Amine quencher 1 (0.5) | isoamyl acetate (6,000) |

TABLE 2

| Shrink agent | Polymer (pbw) | Additive (pbw) | Organic solvent (pbw) |
|---|---|---|---|
| Shrink agent 22 | Polymer 2 (100) | Sulfonium salt 9 (2.0) | isoamyl acetate (600) |
| Shrink agent 23 | Polymer 2 (100) | Sulfonium salt 10 (2.0) | isoamyl acetate (600) |
| Shrink agent 24 | Polymer 2 (100) | Sulfonium salt 11 (2.0) | isoamyl acetate (600) |
| Shrink agent 25 | Polymer 2 (100) | Sulfonium salt 12 (2.0) | isoamyl acetate (600) |
| Shrink agent 26 | Polymer 2 (100) | Iodonium salt 1 (2.0) | isoamyl acetate (600) |
| Shrink agent 27 | Polymer 2 (100) | Ammonium salt 1 (1.5) | isoamyl acetate (600) |
| Shrink agent 28 | Polymer 2 (100) | Sulfonium salt 1 (2.0) | ethyl 2-methylvalerate (600) |
| Shrink agent 29 | Polymer 2 (100) | Sulfonium salt 1 (2.0) | 2-methylbutyl acetate (600) |
| Shrink agent 30 | Polymer 2 (100) | Ammonium salt 2 (2.0) | n-amyl acetate (600) |
| Shrink agent 31 | Polymer 2 (100) | Sulfonium salt 1 (2.0) | n-hexyl acetate (400) 2-nonane (200) |
| Shrink agent 32 | Polymer 2 (100) | Sulfonium salt 1 (2.0) | 3-methylbutyl butyrate (500) anisole (100) |
| Shrink agent 33 | Polymer 2 (100) | Sulfonium salt 1 (2.0) | ethyl hexanoate (500) diisoamyl ether (100) |
| Shrink agent 34 | Polymer 2 (100) | Sulfonium salt 1 (2.0) | ethyl 2-methylbutyrate (400) isoamyl isobutyrate (200) |
| Shrink agent 35 | Polymer 2 (100) | Amine quencher 1 (0.5) | allyl hexanoate (300) ethyl 2-methylbutyrate (300) |
| Shrink agent 36 | Polymer 2 (100) | Amine quencher 2 (0.5) | allyl hexanoate (300) ethyl 2-methylbutyrate (300) |
| Comparative shrink agent 1 | Comparative Polymer 1 (100) | Sulfonium salt 1 (2.0) | isoamyl acetate (600) |
| Comparative shrink agent 2 | Comparative Polymer 2 (100) | Sulfonium salt 1 (2.0) | isoamyl acetate (600) |
| Comparative shrink agent 3 | Polymer 1 (100) | Sulfonium salt 1 (2.0) | PGMEA (3,000) |
| Comparative shrink agent 4 | Polymer 1 (100) | Sulfonium salt 1 (2.0) | butyl acetate (3,000) |

Preparation of Resist Composition

A resist composition in solution form was prepared by dissolving a polymer (Resist Polymer 1), acid generator, quencher, and water-repellent polymer in a solvent in accordance with the formulation of Table 3, and filtering through a filter with a pore size of 0.2 μm. The solvent contained 100 ppm of surfactant FC-4430 (3M-Sumitomo Co., Ltd.).

TABLE 3

| Resist | Polymer (pbw) | Acid generator (pbw) | Quencher (pbw) | Water repellent (pbw) | Organic solvent (pbw) |
|---|---|---|---|---|---|
| Resist 1 | Resist Polymer 1 (100) | PAG1 (10.0) | Amine quencher 1 (2.0) | Water-repellent Polymer 1 (3.0) | PGMEA (2500) γ-butyrolactone (200) |

ArF Lithography Patterning Test

On a silicon wafer, a spin-on carbon film ODL-102 (Shin-Etsu Chemical Co., Ltd.) was deposited to a thickness of 200 nm and a silicon-containing spin-on hard mask SHB-A940 was deposited thereon to a thickness of 35 nm. On this substrate for trilayer process, the resist composition in Table 3 was spin coated, then baked on a hot plate at 100° C. for 60 seconds to form a resist film of 100 nm thick. Using an ArF excimer laser immersion lithography scanner NSR-610C (Nikon Corp., NA 1.30, σ 0.98/0.78, dipole opening 20 deg., azimuthally polarized illumination), the resist film was exposed through a 6% halftone phase shift mask while varying the exposure dose. After the exposure, the resist film was baked (PEB) at 90° C. for 60 seconds and puddle developed in n-butyl acetate for 30 seconds to form a trench pattern having a space width of 45 nm and a pitch of 100 nm.

The shrink agent shown in Tables 1 and 2 was applied onto the resist pattern after development to cover the pattern. The shrink agent coating was baked at the temperature shown in Tables 4 and 5 for 60 seconds. This was followed by puddle development in n-butyl acetate for 20 seconds to remove the shrink agent. Both after development and after shrink treatment, the pattern was observed under a CD-SEM (CG-4000 by Hitachi, Ltd.) to measure the size of trenches at a pitch of 100 nm and edge roughness. The results are shown in Tables 4 and 5.

TABLE 4

| Example | Resist | Pattern size after development (nm) | LER after development (3σ, nm) | Shrink agent | Bake temp. (° C.) | Pattern size after removal of shrink agent (nm) | LER after removal of shrink agent (3σ, nm) |
|---|---|---|---|---|---|---|---|
| 1 | Resist 1 (100) | 45 | 2.7 | Shrink agent 1 | 130 | 23 | 3.3 |
| 2 | Resist 1 (100) | 46 | 2.6 | Shrink agent 2 | 130 | 28 | 2.5 |
| 3 | Resist 1 (100) | 45 | 2.7 | Shrink agent 3 | 135 | 25 | 2.5 |
| 4 | Resist 1 (100) | 45 | 2.7 | Shrink agent 4 | 135 | 27 | 2.7 |
| 5 | Resist 1 (100) | 45 | 2.7 | Shrink agent 5 | 135 | 28 | 2.5 |
| 6 | Resist 1 (100) | 45 | 2.7 | Shrink agent 6 | 140 | 33 | 2.4 |
| 7 | Resist 1 (100) | 45 | 2.7 | Shrink agent 7 | 140 | 28 | 2.6 |
| 8 | Resist 1 (100) | 45 | 2.7 | Shrink agent 8 | 125 | 31 | 2.6 |
| 9 | Resist 1 (100) | 45 | 2.7 | Shrink agent 9 | 135 | 27 | 2.7 |
| 10 | Resist 1 (100) | 45 | 2.5 | Shrink agent 10 | 130 | 28 | 2.8 |
| 11 | Resist 1 (100) | 45 | 2.7 | Shrink agent 11 | 130 | 27 | 2.9 |
| 12 | Resist 1 (100) | 45 | 2.7 | Shrink agent 12 | 120 | 22 | 2.9 |
| 13 | Resist 1 (100) | 45 | 2.7 | Shrink agent 13 | 125 | 23 | 2.6 |
| 14 | Resist 1 (100) | 45 | 2.7 | Shrink agent 14 | 125 | 27 | 2.8 |
| 15 | Resist 1 (100) | 45 | 2.7 | Shrink agent 15 | 125 | 27 | 2.6 |
| 16 | Resist 1 (100) | 45 | 2.7 | Shrink agent 16 | 125 | 26 | 2.8 |
| 17 | Resist 1 (100) | 45 | 2.7 | Shrink agent 17 | 130 | 22 | 2.7 |
| 18 | Resist 1 (100) | 45 | 2.7 | Shrink agent 18 | 130 | 21 | 3.0 |
| 19 | Resist 1 (100) | 45 | 2.7 | Shrink agent 19 | 130 | 30 | 2.4 |
| 20 | Resist 1 (100) | 45 | 2.7 | Shrink agent 20 | 130 | 29 | 2.6 |
| 21 | Resist 1 (100) | 45 | 2.7 | Shrink agent 21 | 130 | 28 | 2.8 |

TABLE 5

| | Resist | Pattern size after development (nm) | LER after development (3σ, nm) | Shrink agent | Bake temp. (° C.) | Pattern size after removal of shrink agent (nm) | LER after removal of shrink agent (3σ, nm) |
|---|---|---|---|---|---|---|---|
| Example | | | | | | | |
| 22 | Resist 1 (100) | 45 | 2.7 | Shrink agent 22 | 130 | 22 | 2.8 |
| 23 | Resist 1 (100) | 46 | 3.3 | Shrink agent 23 | 130 | 22 | 2.9 |
| 24 | Resist 1 (100) | 45 | 2.7 | Shrink agent 24 | 130 | 22 | 2.8 |
| 25 | Resist 1 (100) | 45 | 2.7 | Shrink agent 25 | 130 | 26 | 2.7 |
| 26 | Resist 1 (100) | 45 | 2.7 | Shrink agent 26 | 130 | 28 | 2.8 |
| 27 | Resist 1 (100) | 45 | 2.7 | Shrink agent 27 | 130 | 26 | 2.9 |
| 28 | Resist 1 (100) | 45 | 2.7 | Shrink agent 28 | 130 | 28 | 2.5 |
| 29 | Resist 1 (100) | 45 | 2.7 | Shrink agent 29 | 130 | 26 | 2.6 |
| 30 | Resist 1 (100) | 45 | 2.7 | Shrink agent 30 | 130 | 28 | 2.5 |
| 31 | Resist 1 (100) | 45 | 2.7 | Shrink agent 31 | 130 | 27 | 2.6 |
| 32 | Resist 1 (100) | 45 | 2.7 | Shrink agent 32 | 130 | 22 | 2.7 |
| 33 | Resist 1 (100) | 45 | 2.7 | Shrink agent 33 | 130 | 21 | 2.9 |
| 34 | Resist 1 (100) | 45 | 2.7 | Shrink agent 34 | 130 | 21 | 2.8 |
| 35 | Resist 1 (100) | 45 | 2.7 | Shrink agent 35 | 130 | 28 | 2.7 |
| 36 | Resist 1 (100) | 45 | 2.7 | Shrink agent 36 | 130 | 26 | 2.8 |
| Comparative Example | | | | | | | |
| 1 | Resist 1 (100) | 45 | 2.7 | Comparative shrink agent 1 | 130 | 47 | 3.1 |
| 2 | Resist 1 (100) | 45 | 2.7 | Comparative shrink agent 2 | 140 | 49 | 3.1 |
| 3 | Resist 1 (100) | 45 | 2.7 | Comparative shrink agent 3 | 140 | pattern vanished | — |
| 4 | Resist 1 (100) | 45 | 2.7 | Comparative shrink agent 4 | 140 | 42 | 4.5 |

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

Japanese Patent Application No. 2014-221399 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A pattern forming process comprising the steps of:
    applying a resist composition onto a substrate, said resist composition comprising a polymer comprising recurring units having an acid labile group-substituted carboxyl group, an acid generator and an organic solvent, prebaking to form a resist film, exposing the resist film to high-energy radiation, baking the film, developing the exposed resist film in an organic solvent-based developer to form a negative pattern, applying a shrink agent onto the negative pattern, said shrink agent being a solution of a polymer comprising recurring units (a1) and/or (a2) having the general formula (1) in a solvent selected from the group consisting of ester solvents of 7 to 16 carbon atoms and ketone solvents of 8 to 16 carbon atoms, baking, and removing the excessive shrink agent with the organic solvent-based developer for thereby shrinking the size of spaces in the pattern,

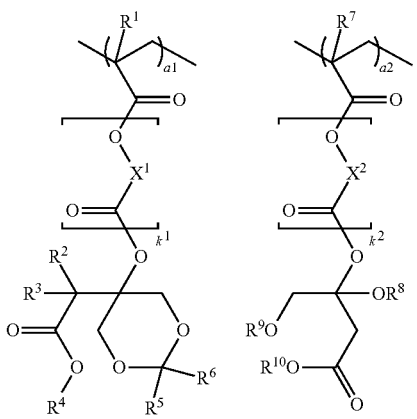

(1)

wherein $R^1$ and $R^7$ each are hydrogen or methyl, $R^2$ and $R^3$ are each independently hydrogen, fluorine, or a straight, branched or cyclic, $C_1$-$C_8$ monovalent hydrocarbon group, $R^4$, $R^8$ and $R^{10}$ are each independently hydrogen or a straight, branched or cyclic, $C_1$-$C_{20}$ monovalent hydrocarbon group in which any constituent —$CH_2$— moiety may be replaced by —O— or —C(=O)—, or which may be substituted with halogen, $R^5$ and $R^6$ are each independently hydrogen or a straight, branched or cyclic, $C_1$-$C_8$ monovalent hydrocarbon group, or $R^5$ and $R^6$ may bond together to form a $C_3$-$C_{17}$ non-aromatic ring with the carbon atom to which they are attached, $R^9$ is an acid labile group, $X^1$ and $X^2$ are each independently a straight, branched or cyclic, $C_1$-$C_{20}$ divalent hydrocarbon group in which any constituent —$CH_2$— moiety may be replaced by —O— or —C(=O)—, $k^1$ and $k^2$ each are 0 or 1, $0 \leq a1 \leq 1.0$, $0 \leq a2 \leq 1.0$, and $0 < a1+a2 \leq 1.0$.

2. The pattern forming process of claim 1 wherein the polymer comprising recurring units (a1) and/or (a2) in the shrink agent further comprises recurring units (a4) and/or (a5) having the general formula (4):

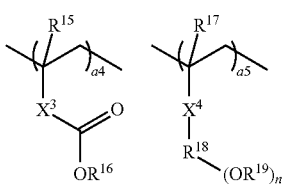

(4)

wherein $R^{15}$ and $R^{17}$ each are hydrogen or methyl, $R^{16}$ and $R^{19}$ each are an acid labile group, $X^3$ is a single bond, a phenylene or naphthylene group, or —C(=O)—O—$R^{20}$—, $R^{20}$ is a straight, branched or cyclic $C_1$-$C_{10}$ alkylene group which may contain ether, ester, lactone ring or hydroxyl, or a phenylene or naphthylene group, $X^4$ is a single bond, a phenylene or naphthylene group which may contain nitro, cyano or halogen, or —C(=O)—O—$R^{21}$—, —C(=O)—NH—$R^{21}$—, —O—$R^{21}$—, or —S—$R^{21}$—, $R^{21}$ is a straight, branched or cyclic $C_1$-$C_{10}$ alkylene group which may contain ether, ester, lactone ring or hydroxyl, or a phenylene or naphthylene group which may contain a straight, branched or cyclic $C_1$-$C_6$ alkyl, alkoxy, acyl, acyloxy, $C_2$-$C_6$ alkenyl, alkoxycarbonyl, $C_6$-$C_{10}$ aryl, nitro, cyano, or halogen, $R^{18}$ is a single bond, a di to penta-valent, straight, branched or cyclic $C_1$-$C_{16}$ aliphatic hydrocarbon group, or phenylene group, which may contain ether or ester, $0 \leq a4 < 1.0$, $0 \leq a5 < 1.0$, $0 \leq a4+a5 < 1.0$, and n is 1 to 4.

3. The pattern forming process of claim 1 wherein the polymer comprising recurring units (a1) and/or (a2) in the shrink agent further comprises recurring units (b) having a hydroxyl, carboxyl, lactone ring, lactam ring, sultone ring, sulfone, sulfonic acid ester, sulfonamide, carboxylic acid amide, nitro, cyano, thienyl, furyl, pyrrole, acid anhydride, imide, —NH—(C=O)—O—, —S—(C=O)—O—, or —ON(=O_2)—, recurring units (d) having an oxirane or oxetane ring, and/or recurring units (e) having an amino group.

4. The pattern forming process of claim 1 wherein the solvent in the shrink agent is at least one solvent selected from the group consisting of ester solvents of 7 to 16 carbon atoms including amyl acetate, isoamyl acetate, 2-methylbutyl acetate, hexyl acetate, 2-ethylhexyl acetate, cyclohexyl acetate, methylcyclohexyl acetate, hexyl formate, ethyl valerate, propyl valerate, isopropyl valerate, butyl valerate, isobutyl valerate, tert-butyl valerate, amyl valerate, isoamyl valerate, ethyl isovalerate, propyl isovalerate, isopropyl isovalerate, butyl isovalerate, isobutyl isovalerate, tert-butyl isovalerate, isoamyl isovalerate, ethyl 2-methylvalerate, butyl 2-methylvalerate, ethyl pivalate, propyl pivalate, isopropyl pivalate, butyl pivalate, tert-butyl pivalate, ethyl pentenoate, propyl pentenoate, isopropyl pentenoate, butyl pentenoate, tert-butyl pentenoate, propyl crotonate, isopropyl crotonate, butyl crotonate, tert-butyl crotonate, butyl propionate, isobutyl propionate, tert-butyl propionate, benzyl propionate, ethyl hexanoate, allyl hexanoate, propyl butyrate, butyl butyrate, isobutyl butyrate, 3-methylbutyl butyrate, tert-butyl butyrate, ethyl 2-methylbutyrate, isopropyl 2-methylbutyrate, methyl benzoate, ethyl benzoate, propyl benzoate, butyl benzoate, phenyl acetate, benzyl acetate, methyl phenylacetate, benzyl formate, phenylethyl formate, methyl 3-phenylpropionate, ethyl phenylacetate, and 2-phenylethyl acetate, and ketone solvents of 8 to 16 carbon atoms including 2-octanone, 3-octanone, 4-octanone, 2-nonanone, 3-nonanone, 4-nonanone, 5-nonanone, ethylcyclohexanone, ethylacetophenone, ethyl n-butyl ketone, di-n-butyl ketone, and diisobutyl ketone.

5. The pattern forming process of claim 1 wherein the shrink agent further comprises a salt compound having the general formula (3)-1 or (3)-2:

 (3)-1

 (3)-2 wherein $R^{14}$ is a straight, branched or cyclic $C_1$-$C_{20}$ alkyl group, $C_2$-$C_{20}$ alkenyl group or $C_6$-$C_{20}$ aryl group which may contain fluorine, ether, ester, lactone ring, lactam ring, carbonyl or hydroxyl, and M is sulfonium, iodonium or ammonium.

6. The pattern forming process of claim 1 wherein the polymer in the resist composition comprises recurring units (a3) having the general formula (2):

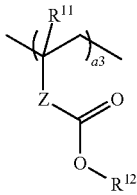

wherein $R^{11}$ is hydrogen or methyl, $R^{12}$ is an acid labile group, Z is a single bond or —C(=O)—O—$R^{13}$—, $R^{13}$ is a straight, branched or cyclic $C_1$-$C_{10}$ alkylene group which may contain ether or ester, or naphthylene group, and $0<a3<1.0$.

7. The pattern forming process of claim 1 wherein the developer comprises at least one organic solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

8. The pattern forming process of claim 1 wherein the high-energy radiation in the exposure step is i-line of wavelength 364 nm, KrF excimer laser of wavelength 248 nm, ArF excimer laser of wavelength 193 nm, EUV of wavelength 13.5 nm, or EB.

9. A shrink agent comprising a polymer and at least one solvent selected from ester solvents of 7 to 16 carbon atoms and ketone solvents of 8 to 16 carbon atoms, said polymer comprising recurring units (a1) and/or (a2) having the general formula (1):

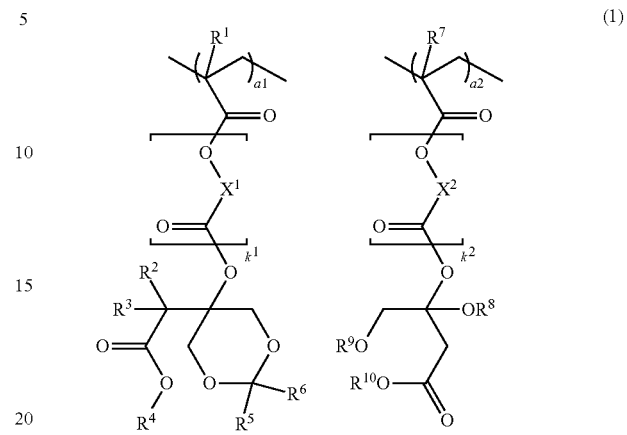

wherein $R^1$ and $R^7$ each are hydrogen or methyl,
$R^2$ and $R^3$ are each independently hydrogen, fluorine, or a straight, branched or cyclic, $C_1$-$C_8$ monovalent hydrocarbon group,
$R^4$, $R^8$ and $R^{10}$ are each independently hydrogen or a straight, branched or cyclic, $C_1$-$C_{20}$ monovalent hydrocarbon group in which any constituent —$CH_2$— moiety may be replaced by —O— or —C(=O)—, or which may be substituted with halogen,
$R^5$ and $R^6$ are each independently hydrogen or a straight, branched or cyclic, $C_1$-$C_8$ monovalent hydrocarbon group, or $R^5$ and $R^6$ may bond together to form a $C_3$-$C_{17}$ non-aromatic ring with the carbon atom to which they are attached,
$R^9$ is an acid labile group,
$X^1$ and $X^2$ are each independently a straight, branched or cyclic, $C_1$-$C_{20}$ divalent hydrocarbon group in which any constituent —$CH_2$— moiety may be replaced by —O— or —C(=O)—,
$k^1$ and $k^2$ each are 0 or 1, $0 \le a1 \le 1.0$, $0 \le a2 \le 1.0$, and $0<a1+a2 \le 1.0$.

10. The shrink agent of claim 9, further comprising a salt compound having the general formula (3)-1 or (3)-2:

$$R^{14}\text{—}CO_2^-M^+ \quad (3)\text{-}1$$

$$R^{14}\text{—}SO_3^-M^+ \quad (3)\text{-}2$$

wherein $R^{14}$ is a straight, branched or cyclic $C_1$-$C_{20}$ alkyl group, $C_2$-$C_{20}$ alkenyl group or $C_6$-$C_{20}$ aryl group which may contain fluorine, ether, ester, lactone ring, lactam ring, carbonyl or hydroxyl, and M is sulfonium, iodonium or ammonium.

* * * * *